(12) United States Patent
Reyes et al.

(10) Patent No.: US 6,379,891 B1
(45) Date of Patent: Apr. 30, 2002

(54) METHOD OF DETECTING HEV INFECTION

(75) Inventors: Gregory R. Reyes, Palo Alto; Patrice O. Yarbough, Redwood Shores, both of CA (US); Daniel W. Bradley, Lawrenceville; Krzysztof Z. Krawczynski, Tucker, both of GA (US); Albert Tam, San Francisco; Kirk E. Fry, Palo Alto, both of CA (US)

(73) Assignees: The United States of America as represented by the Department of Health and Human Services, Washington, DC (US); Genelabs Technologies, Inc., Redwood City ( * ) Notice: Subject to any disclaimer, the term of this patent is extended or adjusted under 35 U.S.C. 154(b) by 0 days.

(21) Appl. No.: 09/553,427

(22) Filed: Apr. 19, 2000

Related U.S. Application Data

(60) Division of application No. 08/478,507, filed on Jun. 7, 1995, which is a division of application No. 08/279,823, filed on Jul. 25, 1994, now Pat. No. 5,789,559, which is a continuation of application No. 07/681,078, filed on Apr. 15, 1991, now abandoned, which is a continuation-in-part of application No. 07/505,888, filed on Apr. 5, 1990, now abandoned, which is a continuation-in-part of application No. 07/420,921, filed on Oct. 13, 1989, now abandoned, which is a continuation-in-part of application No. 07/367,486, filed on Jun. 16, 1989, now abandoned, which is a continuation-in-part of application No. 07/336,672, filed on Apr. 11, 1989, now abandoned, which is a continuation-in-part of application No. 07/208,997, filed on Jun. 17, 1988, now abandoned.

(51) Int. Cl.$^7$ ............................ C12Q 1/68; C07H 21/04
(52) U.S. Cl. ........................................ 435/6; 536/22.1
(58) Field of Search ........................ 435/6, 91.1, 91.2; 536/22.1, 23.1

(56) References Cited

U.S. PATENT DOCUMENTS 5,789,559 A  *  8/1998  Reyes et al. .............. 536/23.72

* cited by examiner

*Primary Examiner*—Eggerton A. Campbell
(74) *Attorney, Agent, or Firm*—Joanne R. Petithory; Peter J. Dehlinger; Larry W. Thrower

(57) ABSTRACT

Viral proteins derived from an enterically transmitted non-A/non-B viral hepatitis agent (HEV) are disclosed. In one embodiment, the protein is immunologically reactive with antibodies present in individuals infected with the viral hepatitis agent. This protein is useful in a diagnostic method for detecting infection by the enterically transmitted agent. Specific epitopes have been identified that are reactive with sera of individual infected with different strains of HEV. Also disclosed are DNA probes derived from a cloned sequence of the viral agent. These probes are useful for identifying and sequencing the entire viral agent and for assaying the presence of the viral agent in an infected sample, by using probe-specific amplification of virus-derived DNA fragments.

5 Claims, 2 Drawing Sheets

METHOD OF DETECTING HEV INFECTION

CROSS-REFERENCE TO RELATED APPLICATIONS

This application is a division of U.S. application Ser. No. 08/478,507, filed Jun. 7, 1995, which is a division of Ser. No. 08/279,823 filed Jul. 25, 1994 now U.S. Pat. No. 5,789,559 which is a continuation of Ser. No. 07/681,078 filed Apr. 5, 1991, abandoned, which is a continuation-in-part of U.S. application Ser. No. 07/505,888, filed Apr. 5, 1990, now abandoned, which is a continuation-in-part of U.S. application Ser. No. 09/420,921, filed Oct. 13, 1989, now abandoned, which is a continuation-in-part of U.S. application Ser. No. 09/367,486, filed Jun. 16, 1989, now abandoned, which is a continuation-in-part of U.S. application Ser. No. 09/336,672, filed Apr. 11, 1989, now abandoned, which is a continuation-in-part of U.S. application Ser. No. 07/208,997, filed Jun. 17, 1988, now abandoned, all of which are herein incorporated by reference.

INTRODUCTION

1. Field of Invention

This invention relates to recombinant proteins, genes, and gene probes and more specifically to such proteins and probes derived from an enterically transmitted nonA/nonB hepatitis viral agent, to diagnostic methods and vaccine applications which employ the proteins and probes, and to gene segments that encode specific epitopes (and proteins artificially produced to contain those epitopes) that are particularly useful in diagnosis and prophylaxis.

2. Background

Enterically transmitted non-A/non-B hepatitis viral agent (ET-NANB; also referred to herein as HEV) is the reported cause of hepatitis in several epidemics and sporadic cases in Asia, Africa, Europe, Mexico, and the Indian subcontinent. Infection is usually by water contaminated with feces, although the virus may also spread by close physical contact. The virus does not seem to cause chronic infection. The viral etiology in ET-NANB has been demonstrated by infection of volunteers with pooled fecal isolates; immune electron microscopy (IEM) studies have shown virus particles with 27–34 nm diameters in stools from infected individuals. The virus particles reacted with antibodies in serum from infected individuals from geographically distinct regions, suggesting that a single viral agent or class is responsible for the majority of ET-NANB hepatitis seen worldwide. No antibody reaction was seen in serum from individuals infected with parenterally transmitted NANB virus (also known as hepatitis C virus or HCV), indicating a different specificity between the two NANB types.

In addition to serological differences, the two types of NANB infection show distinct clinical differences. ET-NANB is characteristically an acute infection, often associated with fever and arthralgia, and with portal inflammation and associated bile stasis in liver biopsy specimens (Arankalle). Symptoms are usually resolved within six weeks. Parenterally transmitted NANB, by contrast, produces a chronic infection in about 50% of the cases. Fever and arthralgia are rarely seen, and inflammation has a predominantly parenchymal distribution (Khuroo, 1980). The course of ET-NANBH is generally uneventful in healthy individuals, and the vast majority of those infected recover without the chronic sequelae seen with HCV. One peculiar epidemiologic feature of this disease, however, is the markedly high mortality observed in pregnant women; this is reported in numerous studies to be on the order of 10–20%. This finding has been seen in a number of epidemiologic studies but at present remains unexplained. Whether this reflects viral pathogenicity, the lethal consequence of the interaction of virus and immune suppressed (pregnant) host, or a reflection of the debilitated prenatal health of a susceptible malnourished population remains to be clarified.

The two viral agents can also be distinguished on the basis of primate host susceptibility. ET-NANB, but not the parenterally transmitted agent, can be transmitted to cynomolgus monkeys. The parenterally transmitted agent is more readily transmitted to chimpanzees than is ET-NANB (Bradley, 1987).

There have been major efforts worldwide to identify and clone viral genomic sequences associated with ET-NANB hepatitis. One goal of this effort, requiring virus-specific genomic sequences, is to identify and characterize the nature of the virus and its protein products. Another goal is to produce recombinant viral proteins which can be used in antibody-based diagnostic procedures and for a vaccine. Despite these efforts, viral sequences associated with ET-NANB hepatitis have not been successfully identified or cloned heretofore, nor have any virus-specific proteins been identified or produced.

RELEVANT LITERATURE

Arankalle, V. A., et al., The Lancet, 550 (Mar. 12, 1988).
Bradley, D. W., et al., J Gen. Virol., 69:1 (1988).
Bradley, D. W. et al., Proc. Nat. Acad. Sci., USA, 84:6277 (1987).
Gravelle, C. R. et al., J. Infect. Diseases, 131:167 (1975).
Kane, M. A., et al., JAMA, 252:3140 (1984).
Khuroo, M. S., *Am. J. Med.,* 48:818 (1980).
Khuroo, M. S., et al., Am. J. Med., 68:818 (1983).
Maniatis, T., et al. *Molecular Cloning: A Laboratory Manual*, Cold Spring Harbor Laboratory (1982).
Seto, B., et al., Lancet, 11:941 (1984).
Sreenivasan, M. A., et al., J. Gen. Virol., 65:1005 (1984).
Tabor, E., et al., J. Infect. Dis., 140:789 (1979).

SUMMARY OF THE INVENTION

Novel compositions, as well as methods of preparation and use of the compositions are provided, where the compositions comprise viral proteins and fragments thereof derived from the viral agent for ET-NANB. A number of specific fragments of viral proteins (and the corresponding genetic sequences) that are particularly useful in diagnosis and vaccine production are also disclosed. Methods for preparation of ET-NANB viral proteins include isolating ET-NANB genomic sequences which are then cloned and expressed in a host cell. The resultant recombinant viral proteins find use as diagnostic agents and as vaccines. The genomic sequences and fragments thereof find use in preparing ET-NANB viral proteins and as probes for virus detection.

DESCRIPTION OF SPECIFIC EMBODIMENTS

Figure 1:
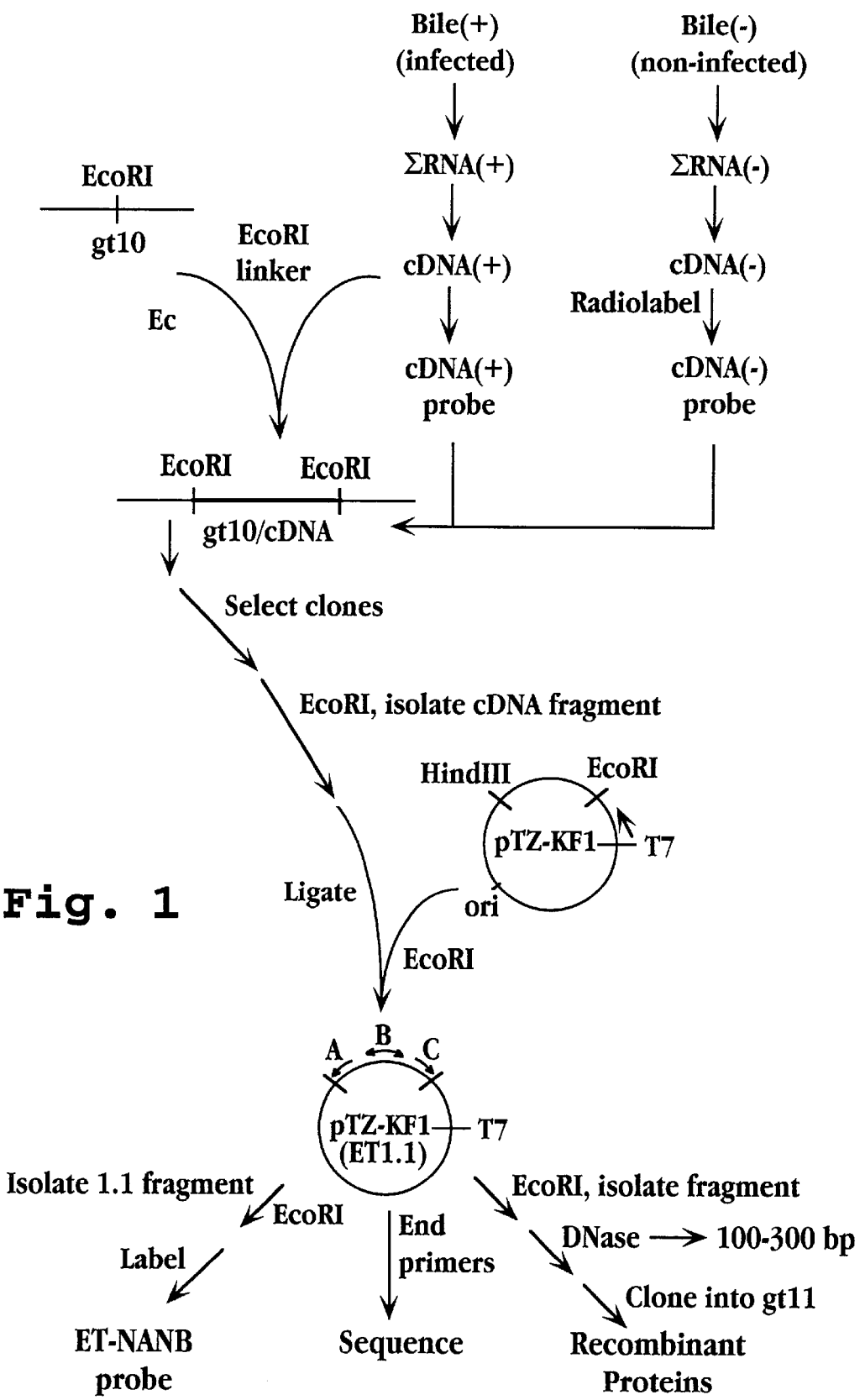
FIG. 1 shows vector constructions and manipulations used in obtaining and sequencing cloned ET-NANB fragment.
Figure 2:
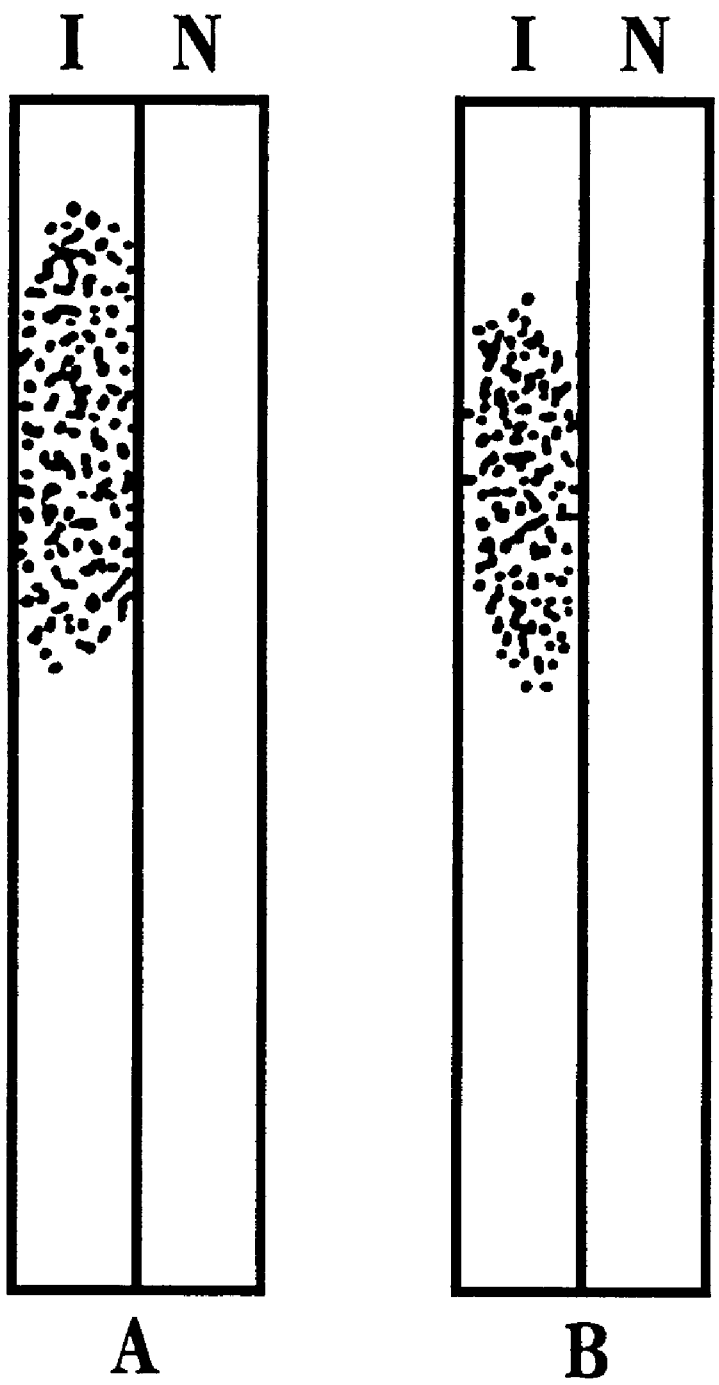
FIGS. 2A–2B are representations of Southern blots in which a radiolabeled ET-NANB probe was hybridized with amplified cDNA fragments prepared from RNA isolated from infected (I) and non-infected (N) bile sources (2A), and from infected (I) and non-infected (N) stool-sample sources (2B).

Novel compositions comprising generic sequences and fragments thereof derived from the viral agent for ET-NANB are provided, together with recombinant viral proteins produced using the genomic sequences and methods of using these compositions. Epitopes on the viral protein have been identified that are particularly useful in diagnosis and vaccine production. Small peptides containing the epitopes are recognized by multiple sera of patients infected with ET-NANB.

The molecular cloning of HEV was accomplished by two very different approaches. The first successful identification of a molecular clone was based on the differential hybridization of putative HEV cDNA clones to heterogeneous cDNA from infected and uninfected cyno bile. cDNAs from both sources were labeled to high specific activity with $^{32}P$ to identify a clone that hybridized specifically to the infected source probe. A cyno monkey infected with the Burma isolate of HEV was used in these first experiments. The sensitivity of this procedure is directly related to the relative abundance of the specific sequence against the overall background. In control experiments, it was found that specific identification of a target sequence may be obtained with as little as 1 specific part per 1000 background sequences. A number of clones were identified by this procedure using libraries and probes made from infected (Burma isolate) and control uninfected cyno bile. The first extensively characterized clone of the 16 plaques purified by this protocol was given the designation ET1.1.

ET1.1 was first characterized as both derived from and unique to the infected source cDNA. Heterogeneous cDNA was amplified from both infected and uninfected sources using a sequence independent single premier amplification technique (SISPA). This technique is described in copending application Ser. No. 208,512, filed Jun. 17, 1988. The limited pool of cDNA made from Burma infected cyno bile could then be amplified enzymatically prior to cloning or hybridization using putative HEV clones as probes. ET1.1 hybridized specifically to the original bile cDNA from the infected source. Further validation of this clone as derived from the genome of HEV was demonstrated by the similarity of the ET1.1 sequence and those present in SISPA cDNA prepared from five different human stool samples collected from different ET-NANBH epidemics including Somalia, Tashkent, Borneo, Mexico and Pakistan. These molecular epidemiologic studies established the isolated sequence as derived from the virus that represented the major cause of ET-NANBH worldwide.

The viral specificity of ET1.1 was further established by the finding that the clone hybridized specifically to RNA extracted from infected cyno liver. Hybridization analysis of polyadenylated RNA demonstrated a unique 7.5 Kb polyadenylated transcript not present in uninfected liver. The size of this transcript suggested that it represented the full length viral genome. Strand specific oligonucleotides were also used to probe viral genomic RNA extracted directly from semi-purified virions prepared from human stool. The strand specificity was based on the RNA-directed RNA polymerase (RDRP) open reading frame (ORF) identified in ET1.1 (see below). Only the probe detecting the sense strand hybridized to the nucleic acid. These studies characterized HEV as a plus sense, single stranded genome. Strand specific hybridization to RNA extracted from the liver also established that the vast majority of intracellular transcript was positive sense. Barring any novel mechanism for virus expression, the negative strand, although not detectable, would be present at a ratio of less than 1:100 when compared with the sense strand.

ET1.1 was documented as exogenous when tested by both Southern blot hybridization and PCR using genomic DNAs derived from uninfected humans, infected and uninfected cynos and also the genomic DNAs from *E. coli* and various bacteriophage sources. The latter were tested in order to rule out trivial contamination with an exogenous sequence introduced during the numerous enzymatic manipulations performed during cDNA construction and amplification. It was also found that the nucleotide sequence of the ET1.1 clone was not homologous to any entries in the Genebank database. The translated open reading frame of the ET1.1 clone did, however, demonstrate limited homology with consensus amino acid residues consistent with an RNA-directed RNA polymerase. This consensus amino acid motif is shared among all positive strand RNA viruses and, as noted above, is present at the 3' end of the HCV genome. The 1.3 Kb clone was therefore presumed to be derived, at least in part, from the nonstructural portion of the viral genome.

Because of the relationship of different strains of ET-NANB to each other that has been demonstrated by the present invention, the genome of the ET-NANB viral agent is defined in this specification as containing a region which is homologous to the 1.33 kb DNA EcoRI insert present in plasmid pTZKF1 (ET1.1) carried in *E. coli* strain BB4 and having ATCC deposit no. 67717. The entire sequence, in both directions, has now been identified as set forth below. The sequences of both strands are provided, since both strands can encode proteins. However, the sequence in one direction has been designated as the "forward" sequence because of statistical similarities to known proteins and because the forward sequence is known to be predominately protein-encoding. This sequence is set forth below along with the three possible transportation sequences. There is one long open reading frame that starts at nucleotide 145 with an isoleucine and extends to the end of the sequence. The two other reading frames have many termination codons. Standard abbreviations for nucleotides and amino acids are used here and elsewhere in this specification.

The gene sequence given below is substantially identical to one given in the parent application. The present sequence differs in the omission of the first 37 nucleotides at the 5' end and last 13 nucleotides at the 3' end, which are derived from the linker used for cloning rather than from the virus. In addition, a G was omitted at position 227 of the sequence given in the parent application.

The following gene sequence has SEQ ID NO.1; the first amino acid sequence in reading frame beginning with nucleotide 1 has SEQ ID NO.2; the second amino acid sequence in reading frame beginning with nuclectide 2 has SEQ ID NO.3; and the third amino acid sequence in reading frame beginning with nucleotide 3 has SEQ ID NO.4.

Forward Sequence

```
                                                       SEQ ID NO. 1:
AGACCTGTCC CTGTTGCAGC TGTTCTACCA CCCTGCCCCG AGCTCGAACA GGGCCTTCTC    60

TACCTGCCCC AGGAGCTCAC CACCTGTGAT AGTGTCGTAA CATTTGAATT AACAGACATT   120

GTGCACTGCC GCATGGCCGC CCCGAGCCAG CGCAAGGCCG TGCTGTCCAC ACTCGTGGGC   180

CGCTACGGCG TCGCACAAA GCTCTACAAT GCTTCCCACT CTGATGTTCG CGACTCTCTC   240

GCCCGTTTTA TCCCGGCCAT TGGCCCCGTA CAGGTTACAA CTTGTGAATT GTACGAGCTA   300

GTGGAGGCCA TGGTCGAGAA GGGCCAGGAT GGCTCCGCCG TCCTTGAGCT TGATCTTTGC   360

AACCGTGACG TGTCCAGGAT CACCTTCTTC CAGAAAGATT GTAACAAGTT CACCACAGGT   420

GAGACCATTG CCCATGGTAA AGTGGGCCAG GGCATCTCGG CCTGGAGCAA GACCTTCTGC   480

GCCCTCTTTG GCCCTTGGTT CCGCGCTATT GAGAAGGCTA TTCTGGCCCT GCTCCCTCAG   540

GGTGTGTTTT ACGGTGATGC CTTTGATGAC ACCGTCTTCT CGGCGGCTGT GGCCGCAGCA   600

AAGGCATCCA TGGTGTTTGA GAATGACTTT TCTGAGTTTG ACTCCACCCA GAATAACTTT   660

TCTCTGGGTC TAGAGTGTGC TATTATGGAG GAGTGTGGGA TGCCGCAGTG GCTCATCCGC   720

CTGTATCACC TTATAAGGTC TGCGTGGATC TTGCAGGCCC CGAAGGAGTC TCTGCGAGGG   780

TTTTGGAAGA AACACTCCGG TGAGCCCGGC ACTCTTCTAT GGAATACTGT CTGGAATATG   840

GCCGTTATTA CCCACTGTTA TGACTTCCGC GATTTTCAGG TGGCTGCCTT TAAAGGTGAT   900

GATTCGATAG TGCTTTGCAG TGAGTATCGT CAGAGTCCAG GAGCTGCTGT CCTGATCGCC   960

GGCTGTGGCT TGAAGTTGAA GGTAGATTTC CGCCCGATCG GTTTGTATGC AGGTGTTGTG  1020

GTGGCCCCCG GCCTTGGCGC GCTCCCTGAT GTTGTGCGCT TCGCCGGCCG GCTTACCGAG  1080

AAGAATTGGG GCCCTGGCCC TGAGCGGGCG GAGCAGCTCC GCCTCGCTGT TAGTGATTTC  1140

CTCCGCAAGC TCACGAATGT AGCTCAGATG TGTGTGGATG TTGTTTCCCG TGTTTATGGG  1200

GTTTCCCCTG GACTCGTTCA TAACCTGATT GGCATGCTAC AGGCTGTTGC TGATGGCAAG  1260

GCACATTTCA CTGAGTCAGT AAAACCAGTG CTCGA                             1295
```

```
                                                       SEQ ID NO. 2
Arg Pro Val Pro Val Ala Ala Val Leu Pro Cys Pro Glu Leu Glu
  1               5                  10                  15

Gln Gly Leu Leu Tyr Leu Pro Gln Glu Leu Thr Thr Cys Asp Ser Val
                 20                  25                  30

Val Thr Phe Glu Leu Thr Asp Ile Val His Cys Arg Met Ala Ala Pro
             35                  40                  45

Ser Gln Arg Lys Ala Val Leu Ser Thr Leu Val Gly Arg Tyr Gly Gly
         50                  55                  60

Arg Thr Lys Leu Tyr Asn Ala Ser His Ser Asp Val Arg Asp Ser Leu
 65                  70                  75                  80

Ala Arg Phe Ile Pro Ala Ile Gly Pro Val Gln Val Thr Thr Cys Glu
                 85                  90                  95

Leu Tyr Glu Leu Val Glu Ala Met Val Glu Lys Gly Gln Asp Gly Ser
            100                 105                 110

Ala Val Leu Glu Leu Asp Leu Cys Asn Arg Asp Val Ser Arg Ile Thr
        115                 120                 125

Phe Phe Gln Lys Asp Cys Asn Lys Phe Thr Thr Gly Glu Thr Ile Ala
    130                 135                 140

His Gly Lys Val Gly Gln Gly Ile Ser Ala Trp Ser Lys Thr Phe Cys
145                 150                 155                 160

Ala Leu Phe Gly Pro Trp Phe Arg Ala Ile Glu Lys Ala Ile Leu Ala
                165                 170                 175
```

-continued

```
Leu Leu Pro Gln Gly Val Phe Tyr Gly Asp Ala Phe Asp Asp Thr Val
            180                 185                 190

Phe Ser Ala Ala Val Ala Ala Lys Ala Ser Met Val Phe Glu Asn
        195                 200                 205

Asp Phe Ser Glu Phe Asp Ser Thr Gln Asn Asn Phe Ser Leu Gly Leu
            210                 215                 220

Glu Cys Ala Ile Met Glu Glu Cys Gly Met Pro Gln Trp Leu Ile Arg
225                 230                 235                 240

Leu Tyr His Leu Ile Arg Ser Ala Trp Ile Leu Gln Ala Pro Lys Glu
                245                 250                 255

Ser Leu Arg Gly Phe Trp Lys Lys His Ser Gly Glu Pro Gly Thr Leu
                260                 265                 270

Leu Trp Asn Thr Val Trp Asn Met Ala Val Ile Thr His Cys Tyr Asp
        275                 280                 285

Phe Arg Asp Phe Gln Val Ala Ala Phe Lys Gly Asp Asp Ser Ile Val
        290                 295                 300

Leu Cys Ser Glu Tyr Arg Gln Ser Pro Gly Ala Ala Val Leu Ile Ala
305                 310                 315                 320

Gly Cys Gly Leu Lys Leu Lys Val Aso Phe Arg Pro Ile Gly Leu Tyr
                325                 330                 335

Ala Gly Val Val Val Ala Pro Gly Leu Gly Ala Leu Pro Asp Val Val
                340                 345                 350

Arg Phe Ala Gly Arg Leu Thr Glu Lys Asn Trp Gly Pro Gly Pro Glu
        355                 360                 365

Arg Ala Glu Gln Leu Arg Leu Ala Val Ser Asp Phe Leu Arg Lys Leu
        370                 375                 380

Thr Asn Val Ala Gln Met Cys Val Asp Val Val Ser Arg Val Tyr Gly
385                 390                 395                 400

Val Ser Pro Gly Leu Val His Asn Leu Ile Gly Met Leu Gln Ala Val
                405                 410                 415

Ala Asp Gly Lys Ala His Phe Thr Glu Ser Val Lys Pro Val Leu
            420                 425                 430

SEQ ID NO. 3
Asp Leu Ser Leu Leu Gln Leu Phe Tyr His Pro Ala Pro Ser Ser Asn
1               5                   10                  15

Arg Ala Phe Ser Thr Cys Pro Arg Ser Ser Pro Val Ile Val Ser
            20                  25                  30

.   His Leu Asn .   Gln Thr Leu Cys Thr Ala Ala Trp Pro Pro Arg
        35                  40                  45

Ala Ser Ala Arg Pro Cys Cys Pro His Ser Trp Ala Ala Thr Ala Val
        50                  55                  60

Ala Gln Ser Ser Thr Met Leu Pro Thr Leu Met Phe Ala Thr Leu Ser
65                  70                  75                  80

Pro Val Leu Ser Arg Pro Leu Ala Pro Tyr Arg Leu Gln Leu Val Asn
                85                  90                  95

Cys Thr Ser .   Trp Arg Pro Trp Ser Arg Arg Ala Arg Met Ala Pro
            100                 105                 110

Pro Ser Leu Ser Leu Ile Phe Ala Thr Val Thr Cys Pro Gly Ser Pro
        115                 120                 125

Ser Ser Arg Lys Ile Val Thr Ser Ser Pro Gln Val Arg Pro Leu Pro
        130                 135                 140

Met Val Lys Trp Ala Arg Ala Ser Arg Pro Gly Ala Arg Pro Ser Ala
145                 150                 155                 160
```

-continued

```
Pro Ser Leu Ala Leu Gly Ser Ala Leu Leu Arg Arg Leu Phe Trp Pro
            165                 170                 175

Cys Ser Leu Arg Val Cys Phe Thr Val Met Pro Leu Met Thr Pro Ser
            180                 185                 190

Ser Arg Arg Leu Trp Pro Gln Gln Arg His Pro Trp Cys Leu Arg Met
            195                 200                 205

Thr Phe Leu Ser Leu Thr Pro Pro Arg Ile Thr Phe Leu Trp Val  .
            210                 215                 220

Ser Val Leu Leu Trp Arg Ser Val Gly Cys Arg Ser Gly Ser Ser Ala
225                 230                 235                 240

Cys Ile Thr Leu  .  Gly Leu Arg Gly Ser Cys Arg Pro Arg Arg Ser
                245                 250                 255

Leu Cys Glu Gly Phe Gly Arg Asn Thr Pro Val Ser Pro Ala Leu Phe
            260                 265                 270

Tyr Gly Ile Leu Ser Gly Ile Trp Pro Leu Leu Pro Thr Val Met Thr
            275                 280                 285

Ser Ala Ile Phe Arg Trp Leu Pro Leu Lys Val Met Ile Arg  .  Cys
            290                 295                 300

Phe Ala Val Ser Ile Val Arg Val Gln Glu Leu Leu Ser  .  Ser Pro
305                 310                 315                 320

Ala Val Ala  .  Ser  .  Arg  .  Ile Ser Ala Arg Ser Val Cys Met
                325                 330                 335

Gln Val Leu Trp Trp Pro Pro Ala Leu Ala Arg Ser Leu Met Leu Cys
            340                 345                 350

Ala Ser Pro Ala Gly Leu Pro Arg Arg Ile Gly Ala Leu Ala Leu Ser
            355                 360                 365

Gly Arg Ser Ser Ser Ala Ser Leu Leu Val Ile Ser Ser Ala Ser Ser
            370                 375                 380

Arg Met  .  Leu Arg Cys Val Trp Met Leu Phe Pro Val Phe Met Gly
385                 390                 395                 400

Phe Pro Leu Asp Ser Phe Ile Thr  .  Leu Ala Cys Tyr Arg Leu Leu
            405                 410                 415

Leu Met Ala Arg His Ile Ser Leu Ser Gln  .  Asn Gln Cys Ser
            420                 425                 430
                                                          SEQ ID NO. 4
Thr Cys Pro Cys Ser Cys Ser Thr Thr Leu Pro Arg Ala Arg Thr
  1           5                  10                  15

Gly Pro Ser Leu Pro Ala Pro Gly Ala His His Leu  .   .  Cys Arg
            20                  25                  30

Asn Ile  .  Ile Asn Arg His Cys Ala Leu Pro His Gly Arg Pro Glu
            35                  40                  45

Pro Ala Gln Gly Arg Ala Val His Thr Arg Gly Pro Leu Arg Arg Ser
       50                  55                  60

His Lys Ala Leu Gln Cys Phe Pro Leu  .  Cys Ser Arg Leu Ser Arg
65                  70                  75                  80

Pro Phe Tyr Pro Gly His Trp Pro Arg Thr Gly Tyr Asn Leu  .  Ile
            85                  90                  95

Val Arg Ala Ser Gly Gly His Gly Arg Glu Gly Pro Gly Trp Leu Arg
            100                 105                 110

Arg Pro  .  Ala  .  Ser Leu Gln Pro  .  Arg Val Gln Asp His Leu
            115                 120                 125

Leu Pro Glu Arg Leu  .  Gln Val His His Arg  .  Asp His Cys Pro
        130                 135                 140

Trp  .  Ser Gly Pro Gly His Leu Gly Leu Glu Gln Asp Leu Leu Arg
```

-continued

```
145                 150                 155                 150

Pro Leu Trp Pro Leu Val Pro Arg Tyr  .  Glu Gly Tyr Ser Gly Pro
                165                 170                 175

Ala Pro Ser Gly Cys Val Leu Arg  .  Cys Leu  .   .  His Arg Leu
                180                 185                 190

Leu Gly Gly Cys Gly Arg Ser Lys Gly Ile His Gly Val  .  Glu  .
                195                 200                 205

Leu Phe  .  Val  .  Leu His Pro Glu  .  Leu Phe Ser Gly Ser Arg
    210                 215                 220

Val Cys Tyr Tyr Gly Gly Val Trp Asp Ala Ala Val Ala His Pro Pro
225                 230                 235                 240

Val Ser Pro Tyr Lys Val Cys Val Asp Leu Ala Gly Pro Glu Gly Val
                245                 250                 255

Ser Ala Arg Val Leu Glu Glu Thr Leu Arg  .  Ala Arg His Ser Ser
                250                 265                 270

Met Glu Tyr Cys Leu Glu Tyr Gly Arg Tyr Tyr Pro Leu Leu  .  Leu
                275                 280                 285

Pro Arg Phe Ser Gly Gly Cys Leu  .  Arg  .   .  Phe Asp Ser Ala
    290                 295                 300

Leu Gln  .  Val Ser Ser Glu Ser Arg Ser Cys Cys Pro Asp Arg Arg
305                 310                 315                 320

Leu Trp Leu Glu Val Glu Gly Arg Phe Pro Pro Asp Arg Phe Val Cys
                325                 330                 335

Arg Cys Cys Gly Gly Pro Arg Pro Trp Arg Ala Pro  .  Cys Cys Ala
                340                 345                 350

Leu Arg Arg Pro Ala Tyr Arg Glu Glu Leu Gly Pro Trp Pro  .  Ala
                355                 360                 365

Gly Gly Ala Ala Pro Pro Arg Cys  .   .  Phe Pro Pro Gln Ala His
                370                 375                 380

Glu Cys Ser Ser Asp Val Cys Gly Cys Cys Phe Pro Cys Leu Trp Gly
385                 390                 395                 400

Phe Pro Trp Thr Arg Ser  .  Pro Asp Trp His Ala Thr Gly Cys Cys
                405                 410                 415

.  Trp Gln Gly Thr Phe His  .  Val Ser Lys Thr Ser Ala Arg
                420                 425                 430
```

The complementary strand, referred to here as the "reverse sequence," is set forth below in the same manner as the forward sequence set forth above. Several open reading frames, shorter than the long open reading frame found in the forward sequence, can be seen this reverse sequence. Because of the relative brevity of the open reading frames in the reverse direction, they are probably not expressed.

The following gene sequence has SEQ ID NO.5.

Reverse Sequence

```
TCGAGCACTG GTTTTACTGA CTCAGTGAAA TGTGCCTTGC CATCAGCAAC AGCCTGTAGC    60    SEQ ID NO. 5:
ATGCCAATCA GGTTATGAAC GAGTCCAGGG GAAACCCCAT AAACACGGGA AACAACATCC   120
ACACACATCT GAGCTACATT CGTGAGCTTG CGGAGGAAAT CACTAACAGC GAGGCGGAGC   180
TGCTCCGCCC GCTCAGGGCC AGGGCCCCAA TTCTTCTCGG TAAGCCGGCC GGCGAAGCGC   240
ACAACATCAG GGAGCGCGCC AAGGCCGGGG GCCACCACAA CACCTGCATA CAAACCGATC   300
GGGCGGAAAT CTACCTTCAA CTTCAAGCCA CAGCCGGCGA TCAGGACAGC AGCTCCTGGA   360
CTCTGACGAT ACTCACTGCA AAGCACTATC GAATCATCAC CTTTAAAGGC AGCCACCTGA   420
AAATCGCGGA AGTCATAACA GTGGGTAATA ACGGCCATAT TCCAGACAGT ATTCCATAGA   480
```

```
                                           -continued
AGAGTGCCGG GCTCACCGGA GTGTTTCTTC CAAAACCCTC GCAGAGACTC CTTCGGGGCC      540

TGCAAGATCC ACGCAGACCT TATAAGGTGA TACAGGCGGA TGAGCCACTG CGGCATCCCA      600

CACTCCTCCA TAATAGCACA CTCTAGACCC AGAGAAAAGT TATTCTGGGT GGAGTCAAAC      660

TCAGAAAAGT CATTCTCAAA CACCATGGAT GCCTTTGCTG CGGCCACAGC CGCCGAGAAG      720

ACGGTGTCAT CAAAGGCATC ACCGTAAAAC ACACCCTGAG GGAGCAGGGC CAGAATAGCC      780

TTCTCAATAG CGCGGAACCA AGGGCCAAAG AGGGCGCAGA AGGTCTTGCT CCAGGCCGAG      840

ATGCCCTGGC CCACTTTACC ATGGGCAATG GTCTCACCTG TGGTGAACTT GTTACAATCT      900

TTCTGGAAGA AGGTGATCCT GGACACGTCA CGGTTGCAAA GATCAAGCTC AAGGACGGCG      960

GAGCCATCCT GGCCCTTCTC GACCATGGCC TCCACTAGCT CGTACAATTC ACAAGTTGTA     1020

ACCTGTACGG GGCCAATGGC CGGGATAAAA CGGGCGAGAG AGTCGCGAAC ATCAGAGTGG     1080

GAAGCATTGT AGAGCTTTGT GCGACCGCCG TAGCGGCCCA CGAGTGTGGA CAGCACGGCC     1140

TTGCGCTGGC TCGGGCGGC CATGCGGCAG TGCACAATGT CTGTTAATTC AAATGTTACG     1200

ACACTATCAC AGGTGGTGAG CTCCTGGGGC AGGTAGAGAA GGCCCTGTTC GAGCTCGGGG     1260

CAGGGTGGTA GAACAGCTGC AACAGGGACA GGTCT                                1295
```

Identity of this sequence with sequences in etiologic agents has been confirmed by locating a corresponding sequence in a viral strain isolated in Burma. The Burmese isolate contains the following sequence of nucleotides (one strand and open reading frames shown). The following gene sequence has SEQ ID NO.6; the protein sequence corresponding to ORF1 has SEQ ID NO.7; ORF2 has SEQ ID NO.8; and ORF3 has SEQ ID NO.9.

```
                    SEQUENCE OF HEV (BURMA STRAIN)

|-ORF1-->
              M  E  A  H  Q  F  I  K  A  P  G
     AGGCAGACCACATATGTGGTCGATGCCATGGAGGCCCATCAGTTTATTAAGGCTCCTGGC

I  T  T  A  I  E  Q  A  A  L  A  A  A  N  S  A  L  A  N  A
     ATCACTACTGCTATTGAGCAGGCTGCTCTAGCAGCGGCCAACTCTGCCCTGGCGAATGCT        120

V  V  V  R  P  F  L  S  H  Q  Q  I  E  I  L  I  N  L  M  Q
     GTGGTAGTTAGGCCTTTTCTCTCTCACCAGCAGATTGAGATCCTCATTAACCTAATGCAA

P  R  Q  L  V  F  R  P  E  V  F  W  N  H  P  I  Q  R  V  I
     CCTCGCCAGCTTGTTTTCCGCCCCGAGGTTTTCTGGAATCATCCCATCCAGCGTGTCATC        240

H  N  E  L  E  L  Y  C  R  A  R  S  G  R  C  L  E  I  G  A
     CATAACGAGCTGGAGCTTTACTGCCGCGCCCGCTCCGGCCGCTGTCTTGAAATTGGCGCC

H  P  R  S  I  N  D  N  P  N  V  V  H  R  C  F  L  R  P  V
     CATCCCCGCTCAATAAATGATAATCCTAATGTGGTCCACCGCTGCTTCCTCCGCCCTGTT        360

G  R  D  V  Q  R  W  Y  T  A  P  T  R  G  P  A  A  N  C  R
     GGGCGTGATGTTCAGCGCTGGTATACTGCTCCCACTCGCGGGCCGGCTGCTAATTGCCGG

R  S  A  L  R  G  L  P  A  A  D  R  T  Y  C  L  D  G  F  S
     CGTTCCGCGCTGCGCGGGCTTCCCGCTGCTGACCGCACTTACTGCCTGACGGGTTTTCT        480

G  C  N  F  P  A  E  T  G  I  A  L  Y  S  L  H  D  M  S  P
     GGCTGTAACTTTCCCGCCGAGACTGGCATCGCCCTCTACTCCCTTCATGATATGTCACCA

S  D  V  A  E  A  M  F  R  H  G  M  T  R  L  Y  A  A  L  H
     TCTGATGTCGCCGAGGCCATGTTCCGCCATGGTATGACGCGGCTCTATGCCGCCCTCCAT       600

L  P  P  E  V  L  L  P  P  G  T  Y  R  T  A  S  Y  L  L  I
     CTTCCGCCTGAGGTCCTGCTGCCCCCTGGCACATATCGCACCGCATCGTATTTGCTAATT

H  D  G  R  R  V  V  V  T  Y  E  G  D  T  S  A  G  Y  N  H
     CATGACGGTAGGCGCGTTGTGGTGACGTATGAGGGTGATACTAGTGCTGGTTACAACCAC       720

D  V  S  N  L  R  S  W  I  R  T  T  K  V  T  G  D  H  P  L
     GATGTCTCCAACTTGCGCTCCTGGATTAGAACCACCAAGGTTACCGGAGACCATCCCCTC
```

SEQUENCE OF HEV (BURMA STRAIN)

```
 V   I   E   R   V   R   A   I   G   C   H   F   V   L   L   L   T   A   A   P
GTTATCGAGCGGGTTAGGGCCATTGGCTGCCACTTTGTTCTCTTGCTCACGGCAGCCCCG              840

E   P   S   P   M   P   Y   V   P   Y   P   R   S   T   E   V   Y   V   R   S
GAGCCATCACCTATGCCTTATGTTCCTTACCCCCGGTCTACCGAGGTCTATGTCCGATCG

I   F   G   P   G   G   T   P   S   L   F   P   T   S   C   S   T   K   S   T
ATCTTCGGCCCGGGTGGCACCCCTTCCTTATTCCCAACCTCATGCTCCACTAAGTCGACC              960

F   H   A   V   P   A   H   I   W   D   R   L   M   L   F   G   A   T   L   D
TTCCATGCTGTCCCTGCCCATATTTGGGACCGTCTTATGCTGTTCGGGGCCACCTTGGAT

D   Q   A   F   C   C   S   R   L   M   T   Y   L   R   G   I   S   Y   K   V
GACCAAGCCTTTTGCTGCTCCCGTTTAATGACCTACCTTCGCGGCATTAGCTACAAGGTC             1080

T   V   G   T   L   V   A   N   E   G   W   N   A   S   E   D   A   L   T   A
ACTGTTGGTACCCTTGTGGCTAATGAAGGCTGGAATGCCTCTGAGGACGCCCTCACAGCT

V   I   T   A   A   Y   L   T   I   C   H   Q   R   Y   L   R   T   Q   A   I
GTTATCACTGCCGCCTACCTTACCATTTGCCACCAGCGGTATCTCCGCACCCAGGCTATA             1200

S   K   G   M   R   R   L   E   R   E   H   A   Q   K   F   I   T   R   L   Y
TCCAAGGGGATGCGTCGTCTGGAACGGGAGCATGCCCAGAAGTTTATAACACGCCTCTAC

S   W   L   F   E   K   S   G   R   D   Y   I   P   G   R   Q   L   E   F   Y
AGCTGGCTCTTCGAGAAGTCCGGCCGTGATTACATCCCTGGCCGTCAGTTGGAGTTCTAC             1320

A   Q   C   R   R   W   L   S   A   G   F   H   L   D   P   R   V   L   V   F
GCCCAGTGCAGGCGCTGGCTCTCCGCCGGCTTTCATCTTGATCCACGGGTGTTGGTTTTT

D   E   S   A   P   C   H   C   R   T   A   I   R   K   A   L   S   K   F   C
GACGAGTCGGCCCCCTGCCATTGTAGGACCGCGATCCGTAAGGCGCTCTCAAAGTTTTGC             1440

C   F   M   K   W   L   G   Q   E   C   T   C   F   L   Q   P   A   E   G   A
TGCTTCATGAAGTGGCTTGGTCAGGAGTGCACCTGCTTCCTTCAGCCTGCAGAAGGCGCC

V   G   D   Q   G   H   D   N   E   A   Y   E   G   S   D   V   D   P   A   E
GTCGGCGACCAGGGTCATGATAATGAAGCCTATGAGGGGTCCGATGTTGACCCTGCTGAG             1560

S   A   I   S   D   I   S   G   S   Y   V   V   P   G   T   A   L   Q   P   L
TCCGCCATTAGTGACATATCTGGGTCCTATGTCGTCCCTGGCACTGCCCTCCAACCGCTC

Y   Q   A   L   D   L   P   A   E   I   V   A   R   A   G   R   L   T   A   T
TACCAGGCCCTCGATCTCCCCGCTGAGATTGTGGCTCGCGCGGGCCGGCTGACCGCCACA             1680

V   K   V   S   Q   V   D   G   R   I   D   C   E   T   L   L   G   N   K   T
GTAAAGGTCTCCCAGGTCGATGGGCGGATCGATTGCGAGACCCTTCTTGGTAACAAAACC

F   R   T   S   F   V   D   G   A   V   L   E   T   N   G   P   E   R   H   N
TTTCGCACGTCGTTCGTTGACGGGGCGGTCTTAGAGACCAATGGCCCAGAGCGCCACAAT             1800

L   S   F   D   A   S   Q   S   T   M   A   A   G   P   F   S   L   T   Y   A
CTCTCCTTCGATGCCAGTCAGAGCACTATGGCCGCTGGCCCTTTCAGTCTCACCTATGCC

A   S   A   A   G   L   E   V   R   Y   V   A   A   G   L   D   H   R   A   V
GCCTCTGCAGCTGGGCTGGAGGTGCGCTATGTTGCTGCCGGGCTTGACCATCGGGCGGTT             1920

F   A   P   G   V   S   P   R   S   A   P   G   E   V   T   A   F   C   S   A
TTTGCCCCCGGTGTTTCACCCCGGTCAGCCCCCGGCGAGGTTACCGCCTTCTGCTCTGCC

L   Y   R   F   N   R   E   A   Q   R   H   S   L   I   G   N   L   W   F   H
CTATACAGGTTTAACCGTGAGGCCCAGCGCCATTCGCTGATCGGTAACTTATGGTTCCAT             2040

P   E   G   L   I   G   L   F   A   D   F   S   P   G   H   V   W   E   S   A
CCTGAGGGACTCATTGGCCTCTTCGCCCCGTTTTCGCCCGGGCATGTTTGGGAGTCGGCT

N   P   F   C   G   E   S   T   L   Y   T   R   T   W   S   E   V   D   A   V
AATCCATTCTGTGGCGAGAGCACACTTTACACCCGTACTTGGTCGGAGGTTGATGCCGTC             2160

S   S   P   A   R   P   D   L   G   F   M   S   E   P   S   I   P   S   R   A
TCTAGTCCAGCCCGGCCTGACTTAGGTTTTATGTCTGAGCCTTCTATACCTAGTAGGGCC

A   T   P   T   L   A   A   P   L   P   P   P   A   P   D   P   S   P   P   P
GCCACGCCTACCCTGGCGGCCCCTCTACCCCCCCCTGCACCGGACCCTTCCCCCCCTCCC             2280

S   A   P   A   L   A   E   P   A   S   G   A   T   A   G   A   P   A   I   T
TCTGCCCCGGCGCTTGCTGAGCCGGCTTCTGGCGCTACCGCCGGGGCCCCGGCCATAACT
```

-continued

SEQUENCE OF HEV (BURMA STRAIN)

```
H  Q  T  A  R  H  R  R  L  L  F  T  Y  P  D  G  S  K  V  F
CACCAGACGGCCCGGCACCGCCGCCTGCTCTTCACCTACCCGGATGGCTCTAAGGTATTC    2400

A  G  S  L  F  E  S  T  C  T  W  L  V  N  A  S  N  V  D  H
GCCGGCTCGCTGTTCGAGTCGACATGCACGTGGCTCGTTAACGCGTCTAATGTTGACCAC

R  P  G  G  G  L  C  H  A  F  Y  Q  R  Y  P  A  S  F  D  A
CGCCCTGGCGGCGGGCTTTGCCATGCATTTTACCAAAGGTACCCCGCCTCCTTTGATGCT    2520

A  S  F  V  M  R  D  G  A  A  A  Y  T  L  T  P  R  P  I  I
GCCTCTTTTGTGATGCGCGACGGCGCGGCCGCGTACACACTAACCCCCCGGCCAATAATT

H  A  V  A  P  D  Y  R  L  E  H  N  P  K  R  L  E  A  A  Y
CACGCTGTCGCCCCTGATTATAGGTTGGAACATAACCCAAAGAGGCTTGAGGCTGCTTAT    2640

R  E  T  C  S  R  L  G  T  A  A  Y  P  L  L  G  T  G  I  Y
CGGGAAACTTGCTCCCGCCTCGGCACCGCTGCATACCCGCTCCTCGGGACCGGCATATAC

Q  V  P  I  G  P  S  F  D  A  W  E  R  N  H  R  P  G  D  E
CAGGTGCCGATCGGCCCCAGTTTTGACGCCTGGGAGCGGAACCACCGCCCCGGGGATGAG    2760

L  Y  L  P  E  L  A  A  R  W  F  E  A  N  R  P  T  R  P  T
TTGTACCTTCCTGAGCTTGCTGCCAGATGGTTTGAGGCCAATAGGCCGACCCGCCCGACT

L  T  I  T  E  D  V  A  R  T  A  N  L  A  I  E  L  D  S  A
CTCACTATAACTGAGGATGTTGCACGGACAGCGAATCTGGCCATCGAGCTTGACTCAGCC    2880

T  D  V  G  R  A  C  A  G  C  R  V  T  P  G  V  V  Q  Y  Q
ACAGATGTCGGCCGGGCCTGTGCCGGCTGTCGGGTCACCCCCGGCGTTGTTCAGTACCAG

F  T  A  G  V  P  G  S  G  K  S  R  S  I  T  Q  A  D  V  D
TTTACTGCAGGTGTGCCTGGATCCGGCAAGTCCCGCTCTATCACCCAAGCCGATGTGGAC    3000

V  V  V  V  P  T  R  E  L  R  N  A  W  R  R  R  G  F  A  A
GTTGTCGTGGTCCCGACGCGTGAGTTGCGTAATGCCTGGCGCCGTCGCGGCTTTGCTGCT

F  T  P  H  T  A  A  R  V  T  Q  G  R  R  V  V  I  D  E  A
TTTACCCCGCATACTGCCGCCAGAGTCACCCAGGGGCGCCGGGTTGTCATTGATGAGGCT    3120

P  S  L  P  P  H  L  L  L  H  M  Q  R  A  A  T  V  H  L
CCATCCCTCCCCCCTCACCTGCTGCTGCTCCACATGCAGCGGGCCGCCACCGTCCACCTT

L  G  D  P  N  Q  I  P  A  I  D  F  E  H  A  G  L  V  P  A
CTTGGCGACCCGAACCAGATCCCAGCCATCGACTTTGAGCACGCTGGGCTCGTCCCCGCC    3240

I  R  P  D  L  G  P  T  S  W  W  H  V  T  H  R  W  P  A  D
ATCAGGCCCGACTTAGGCCCCACCTCCTGGTGGCATGTTACCCATCGCTGGCCTGCGGAT

V  C  E  L  I  R  G  A  Y  P  M  I  Q  T  T  S  R  V  L  R
GTATGCGAGCTCATCCGTGGTGCATACCCCATGATCCAGACCACTAGCCGGGTTCTCCGT    3360

S  L  F  W  G  E  P  A  V  G  Q  K  L  V  F  T  Q  A  A  K
TCGTTGTTCTGGGGTGAGCCTGCCGTCGGGCAGAAACTAGTGTTCACCCAGGCGGCCAAG

P  A  N  P  G  S  V  T  V  H  E  A  Q  G  A  T  Y  T  E  T
CCCGCCAACCCCGGCTCAGTGACGGTCCACGAGGCGCAGGGCGCTACCTACACGGAGACC    3480

T  I  I  A  T  A  D  A  R  G  L  I  Q  S  S  R  A  H  A  I
ACTATTATTGCCACAGCAGATGCCCGGGGCCTTATTCAGTCGTCTCGGGCTCATGCCATT

V  A  L  T  R  H  T  E  K  C  V  I  I  D  A  P  G  L  L  R
GTTGCTCTGACGCGCCACACTGAGAAGTGCGTCATCATTGACGCACCAGGCCTGCTTCGC    3600

E  V  G  I  S  D  A  I  V  N  N  F  F  L  A  G  G  E  I  G
GAGGTGGGCATCTCCGATGCAATCGTTAATAACTTTTTCCTCGCTGGTGGCGAAATTGGT

H  Q  R  P  S  V  I  P  R  G  N  P  D  A  N  V  D  T  L  A
CACCAGCGCCCATCAGTTATTCCCCGTGGCAACCCTGACGCCAATGTTGACACCCTGGCT    3720

A  F  P  P  S  C  Q  I  S  A  F  H  Q  L  A  E  E  L  G  H
GCCTTCCCGCCGTCTTGCCAGATTAGTGCCTTCCATCAGTTGGCTGAGGAGCTTGGCCAC

R  P  V  P  V  A  A  V  L  P  P  C  P  E  L  E  Q  G  L  L
AGACCTGTCCCTGTTGCAGCTGTTCTACCACCCTGCCCCGAGCTCGAACAGGGCCTTCTC    3840

Y  L  P  Q  E  L  T  T  C  D  S  V  V  T  F  E  L  T  D  I
```

SEQUENCE OF HEV (BURMA STRAIN)

```

TACCTGCCCCAGGAGCTCACCACCTGTGATAGTGTCGTAACATTTGAATTAACAGACATT

V   H   C   R   M   A   A   P   S   Q   R   K   A   V   L   S   T   L   V   G
GTGCACTGCCGCATGGCCGCCCCGAGCCAGCGCAAGGCCGTGCTGTCCACACTCGTGGGC          3960

R   Y   G   G   R   T   K   L   Y   N   A   S   H   S   D   V   R   D   S   L
CGCTACGGCGGTCGCACAAAGCTCTACAATGCTTCCCACTCTGATGTTCGCGACTCTCTC

A   R   F   I   P   A   I   G   P   V   Q   V   T   T   C   E   L   Y   E   L
GCCCGTTTTATCCCGGCCATTGGCCCCGTACAGGTTACAACTTGTGAATTGTACGAGCTA          4080

V   E   A   M   V   E   K   G   Q   D   G   S   A   V   L   E   L   D   L   C
GTGGAGGCCATGGTCGAGAAGGGCCAGGATGGCTCCGCCGTCCTTGAGCTTGATCTTTGC

N   R   D   V   S   R   I   T   F   F   Q   K   D   C   N   K   F   T   T   G
AACCGTGACGTGTCCAGGATCACCTTCTTCCAGAAAGATTGTAACAAGTTCACCACAGGT          4200

E   T   I   A   H   G   K   V   G   Q   G   I   S   A   W   S   K   T   F   C
GAGACCATTGCCCATGGTAAAGTGGGCCAGGGCATCTCGGCCTGGAGCAAGACCTTCTGC

A   L   F   G   P   W   F   R   A   I   E   K   A   I   L   A   L   L   P   Q
GCCCTCTTTGGCCCTTGGTTCCGCGCTATTGAGAAGGCTATTCTGGCCCTGCTCCCTCAG          4320

G   V   F   Y   G   D   A   F   D   D   T   V   F   S   A   A   V   A   A   A
GGTGTGTTTTACGGTGATGCCTTTGATGACACCGTCTTCTCGGCGGCTGTGGCCGCAGCA

K   A   S   M   V   F   E   N   D   F   S   E   F   D   S   T   Q   N   N   F
AAGGCATCCATGGTGTTTGAGAATGACTTTTCTGAGTTTGACTCCACCCAGAATAACTTT          4440

S   L   G   L   E   C   A   I   M   E   E   C   G   M   P   Q   W   L   I   R
TCTCTGGGTCTAGAGTGTGCTATTATGGAGGAGTGTGGGATGCCGCAGTGGCTCATCCGC

L   Y   H   L   I   R   S   A   W   I   L   Q   A   P   K   E   S   L   R   G
CTGTATCACCTTATAAGGTCTGCGTGGATCTTGCAGGCCCCGAAGGAGTCTCTGCGAGGG          4560

F   W   K   K   H   S   G   E   P   G   T   L   L   W   N   T   V   W   N   M
TTTTGGAAGAAACACTCCGGTGAGCCCGGCACTCTTCTATGGAATACTGTCTGGAATATG

A   V   I   T   H   C   Y   D   F   R   D   F   Q   V   A   A   F   K   G   D
GCCGTTATTACCCACTGTTATGACTTCCGCGATTTTCAGGTGGCTGCCTTTAAAGGTGAT          4680

D   S   I   V   L   C   S   E   Y   R   Q   S   P   G   A   A   V   L   I   A
GATTCGATAGTGCTTTGCAGTGAGTATCGTCAGAGTCCAGGAGCTGCTGTCCTGATCGCC

G   C   G   L   K   L   K   V   D   F   R   P   I   G   L   Y   A   G   V   V
GGCTGTGGCTTGAAGTTGAAGGTAGATTTCCGCCCGATCGGTTTGTATGCAGGTGTTGTG          4800

V   A   P   G   L   G   A   L   P   D   V   V   R   F   A   G   R   L   T   E
GTGGCCCCCGGCCTTGGCGCGCTCCCTGATGTTGTGCGCTTCGCCGGCCGGCTTACCGAG

K   N   W   G   P   G   P   E   R   A   E   Q   L   R   L   A   V   S   D   F
AAGAATTGGGGCCCTGGCCCTGAGCGGGCGGAGCAGCTCCGCCTCGCTGTTAGTGATTTC          4920

L   R   K   L   T   N   V   A   Q   M   C   V   D   V   V   S   R   V   Y   G
CTCCGCAAGCTCACGAATGTAGCTCAGATGTGTGTGGATGTTGTTTCCCGTGTTTATGGG

V   S   P   G   L   V   H   N   L   I   G   M   L   Q   A   V   A   D   G   K
GTTTCCCCTGGACTCGTTCATAACCTGATTGGCATGCTACAGGCTGTTGCTGATGGCAAG          5040

A   H   F   T   E   S   V   K   P   V   L   D   L   T   N   S   I   L   C   R
GCACATTTCACTGAGTCAGTAAAACCAGTGCTCGACTTGACAAATTCAATCTTGTGTCGG

|-ORF3--->
              M   N   N   M   S   F   A   A   P   M   G   S   R   P   C   A   L   G
                                                                      M   R   P   R   P
  V   E   Z                                               |-ORF2-->
GTGGAATGAATAACATGTCTTTTGCTGCGCCCATGGGTTCGCGACCATGCGCCCTCGGCC          5160

L   F   C   C   C   S   S   C   F   C   L   C   C   P   R   H   R   P   V   S
  I   L   L   L   L   M   F   L   P   M   L   P   A   P   P   P   G   Q   P

TATTTTGTTGCTGCTCCTCATGTTTTTGCCTATGCTGCCCGCGCCACCGCCCGGTCAGCC
  R   L   A   A   V   V   G   G   A   A   A   V   P   A   V   V   S   G   V   T
  S   G   R   R   R   G   R   R   S   G   G   S   G   G   G   F   W   G   D   R

GTCTGGCCGCCGTCGTGGGCGGCGCAGCGGCGGTTCCGGCGGTGGTTTCTGGGGTGACCG          5280
```

SEQUENCE OF HEV (BURMA STRAIN)

```
 G  L  I  L  S  P  S  Q  S  P  I  F  I  Q  P  T  P  S  P  P
    V  D  S  Q  P  F  A  I  P  Y  I  H  P  T  N  P  F  A  P  D
GGTTGATTCTCAGCCCTTCGCAATCCCCTATATTCATCCAACCAACCCCTTCGCCCCCGA

M  S  P  L  R  P  G  L  D  L  V  F  A  N  P  P  D  H  S  A
    V  T  A  A  A  G  A  G  P  R  V  R  Q  P  A  R  P  L  G  S
TGTCACCGCTGCGGCCGGGGCTGGACCTCGTGTTCGCCAACCCGCCCGACCACTCGGCTC         5400

P  L  G  V  T  R  P  S  A  P  P  L  P  H  V  V  D  L  P  Q
    A  W  R  D  Q  A  Q  R  P  A  V  A  S  R  R  R  P  T  T  A
CGCTTGGCGTGACCAGGCCCAGCGCCCCGCCGTTGCCTCACGTCGTAGACCTACCACAGC

L  G  P  R  R  Z
    G  A  A  P  L  T  A  V  A  P  A  H  D  T  P  P  V  P  D  V
TGGGGCCGCGCCGCTAACCGCGGTCGCTCCGGCCCATGACACCCCGCCAGTGCCTGATGT         5520
    D  S  R  G  A  I  L  R  R  Q  Y  N  L  S  T  S  P  L  T  S
CGACTCCCGCGGCGCCATCTTGCGCCGGCAGTATAACCTATCAACATCTCCCCTTACCTC

S  V  A  T  G  T  N  L  V  L  Y  A  A  P  L  S  P  L  L  P
TTCCGTGGCCACCGGCACTAACCTGGTTCTTTATGCCGCCCCTCTTAGTCCGCTTTTACC         5640

L  Q  D  G  T  N  T  H  I  M  A  T  E  A  S  N  Y  A  Q  Y
CCTTCAGGACGGCACCAATACCCATATAATGGCCACGGAAGCTTCTAATTATGCCCAGTA

R  V  A  R  A  T  I  R  Y  R  P  L  V  P  N  A  V  G  G  Y
CCGGGTTGCCCGTGCCACAATCCGTTACCGCCCGCTGGTCCCCAATGCTGTCGGCGGTTA         5760

A  I  S  I  S  F  W  P  Q  T  T  T  T  P  T  S  V  D  M  N
CGCCATCTCCATCTCATTCTGGCCACAGACCACCACCACCCCGACGTCCGTTGATATGAA

S  I  T  S  T  D  V  R  I  L  V  Q  P  G  I  A  S  E  L  V
TTCAATAACCTCGACGGATGTTCGTATTTTAGTCCAGCCCGGCATAGCCTCTGAGCTTGT         5880

I  P  S  E  R  L  H  Y  R  N  Q  G  W  R  S  V  E  T  S  G
GATCCCAAGTGAGCGCCTACACTATCGTAACCAAGGCTGGCGCTCCGTCGAGACCTCTGG

V  A  E  E  A  T  S  G  L  V  M  L  C  I  H  G  S  L  V
GGTGGCTGAGGAGGAGGCTACCTCTGGTCTTGTTATGCTTTGCATACATGGCTCACTCGT         6000

N  S  Y  T  N  T  P  Y  T  G  A  L  G  L  L  D  F  A  L  E
AAATTCCTATACTAATACACCCTATACCGGTGCCCTCGGGCTGTTGGACTTTGCCCTTGA

L  E  F  R  N  L  T  P  G  N  T  N  T  R  V  S  R  Y  S  S
GCTTGAGTTTCGCAACCTTACCCCCGGTAACACCAATACGCGGGTCTCCCGTTATTCCAG         6120

T  A  R  H  R  L  R  R  G  A  D  G  T  A  E  L  T  T  T  A
CACTGCTCGCCACCGCCTTCGTCGCGGTGCGGACGGGACTGCCGAGCTCACCACCACGGC

A  T  R  F  M  K  D  L  Y  F  T  S  T  N  G  V  G  E  I  G
TGCTACCCGCTTTATGAAGGACCTCTATTTTACTAGTACTAATGGTGTCGGTGAGATCGG         6240

R  G  I  A  L  T  L  F  N  L  A  D  T  L  L  G  G  L  P  T
CCGCGGGATAGCCCTCACCCTGTTCAACCTTGCTGACACTCTGCTTGGCGGCCTGCCGAC

E  L  I  S  S  A  G  G  Q  L  F  Y  S  R  P  V  V  S  A  N
AGAATTGATTTCGTCGGCTGGTGGCCAGCTGTTCTACTCCCGTCCCGTTGTCTCAGCCAA         6360

G  E  P  T  V  K  L  Y  T  S  V  E  N  A  Q  Q  D  K  G  I
```

-continued

SEQUENCE OF HEV (BURMA STRAIN)

```
TGGCGAGCCGACTGTTAAGTTGTATACATCTGTAGAGAATGCTCAGCAGGATAAGGGTAT

A   I   P   H   D   I   D   L   G   E   S   R   V   V   I   Q   D   Y   D   N

TGCAATCCCGCATGACATTGACCTCGGAGAATCTCGTGTGGTTATTCAGGATTATGATAA          6480

Q   H   E   Q   D   R   P   T   P   S   P   A   P   S   R   P   F   S   V   L

CCAACATGAACAAGATCGGCCGACGCCTTCTCCAGCCCCATCGCGCCCTTTCTCTGTCCT

R   A   N   D   V   L   W   L   S   L   T   A   A   E   Y   D   Q   S   T   Y

TCGAGCTAATGATGTGCTTTGGCTCTCTCTCACCGCTGCCGAGTATGACCAGTCCACTTA          6600

G   S   S   T   G   P   V   Y   V   S   D   S   V   T   L   V   N   V   A   T

TGGCTCTTCGACTGGCCCAGTTTATGTTTCTGACTCTGTGACCTTGGTTAATGTTGCGAC

G   A   Q   A   V   A   R   S   L   D   W   T   K   V   T   L   D   G   R   P

CGGCGCGCAGGCCGTTGCCCGGTCGCTCGATTGGACCAAGGTCACACTTGACGGTCGCCC          6720

L   S   T   I   Q   Q   Y   S   K   T   F   F   V   L   P   L   R   G   K   L

CCTCTCCACCATCCAGCAGTACTCGAAGACCTTCTTTGTCCTGCCGCTCCGCGGTAAGCT

S   F   W   E   A   G   T   T   K   A   G   Y   P   Y   N   Y   N   T   T   A

CTCTTTCTGGGAGGCAGGCACAACTAAAGCCGGGTACCCTTATAATTATAACACCACTGC          6840

S   D   Q   L   L   V   E   N   A   A   G   H   R   V   A   I   S   T   Y   T

TAGCGACCAACTGCTTGTCGAGAATGCCGCCGGGCACCGGGTCGCTATTTCCACTTACAC

T   S   L   G   A   G   P   V   S   I   S   A   V   A   V   L   A   P   H   S

CACTAGCCTGGGTGCTGGTCCCGTCTCCATTTCTGCGGTTGCCGTTTTAGCCCCCCACTC          6960

A   L   A   L   L   E   D   T   L   D   Y   P   A   R   A   H   T   F   D   D

TGCGCTAGCATTGCTTGAGGATACCTTGGACTACCCTGCCCGCGCCCATACTTTTGATGA

F   C   P   E   C   R   P   L   G   L   Q   G   C   A   F   Q   S   T   V   A

TTTCTGCCCAGAGTGCCGCCCCCTTGGCCTTCAGGGCTGCGCTTTCCAGTCTACTGTCGC          7080

E   L   Q   R   L   K   M   K   V   G   K   T   R   E   L   Z

TGAGCTTCAGCGCCTTAAGATGAAGGTGGGTAAAACTCGGGAGTTGTAGTTTATTTGCTT

GTGCCCCCCTTCTTTCTGTTGCTTATTTCTCATTTCTGCGTTCCGCGCTCCCTGA              7195
```

Total number of bases in this sequence as presented is 7195. The poly-A tail present in the cloned sequence has been omitted.

The ability of the methods described herein to isolate and identify genetic material from other NANB hepatitis strains has been confirmed by identifying genetic material from an isolate obtained in Mexico. The sequence of this isolate was about 75% identical to the ET1.1 sequence set forth in SEQ ID NO.1 above. The sequence was identified by hybridization using the conditions set forth in Section II.B below.

In this different approach to isolation of the virus, cDNA libraries were made directly from a semi-purified human stool specimen collected from an outbreak of ET-NANB in Telixtac. The recovery of cDNA and the construction of representative libraries was assured by the application of sequence independent single premier amplification (SISPA). A cDNA library constructed in lambda gt11 from such an amplified cDNA population was screened with a serum considered to have "high" titer anti-HEV antibodies as assayed by direct immunofluorescence on liver sections from infected cynos. Two cDNA clones, denoted 406.3-2 and 406.4-2, were identified by this approach from a total of 60,000 screened. The sequence of these clones was subsequently localized to the 3' half of the viral genome by homology comparison to the HEV (Burma) sequence obtained from clones isolated by hybridization screening of libraries with the original ET1.1 clone.

These isolated cDNA epitopes when used as hybridization probes on Northern blots of RNA extracted from infected cyno liver gave a somewhat different result when compared to the Northern blots obtained with the ET1.1 probe. In addition to the single 7.5 Kb transcript seen using ET1.1, two additional transcripts of 3.7 and 2.0 Kb were identified using either of these epitopes as hybridization probes. These polyadenylated transcripts were identified using the extreme 3' end epitope clone (406.3-2) as probe and therefore established these transcripts as co-terminal with the 3' end of the genome (see below). One of the epitope clones (406.4-2) was subsequently shown to react in a specific fashion with antisera collected from 5 different geographic epidemics (Somalia, Burma, Mexico, Tashkent and Pakistan). The 406.3-2 clone reacted with sera from 4 out of these same 5 epidemics (Yarbough et al., 1990). Both clones reacted with only post inoculation antisera from infected cynos. The latter experiment confirmed that seroconversion in experimentally infected cynos was related to the isolated exogenous cloned sequence.

A composite cDNA sequence (obtained from several clones of the Mexican strain) is set forth below. Composite Mexico strain sequence (SEQ ID NO.10):

```
GCCATGGAGG CCCACCAGTT CATTAAGGCT CCTGGCATCA CTACTGCTAT TGAGCAAGCA    60  SEQ ID NO. 10:
GCTCTAGCAG CGGCCAACTC CGCCCTTGCG AATGCTGTGG TGGTCCGGCC TTTCCTTTCC   120
CATCAGCAGG TTGAGATCCT TATAAATCTC ATGCAACCTC GGCAGCTGGT GTTTCGTCCT   180
GAGGTTTTTT GGAATCACCC GATTCAACGT GTTATACATA ATGAGCTTGA GCAGTATTGC   240
CGTGCTCGCT CGGGTCGCTG CCTTGAGATT GGAGCCCACC CACGCTCCAT TAATGATAAT   300
CCTAATGTCC TCCATCGCTG CTTTCTCCAC CCCGTCGGCC GGGATGTTCA GCGCTGGTAC   360
ACAGCCCCGA CTAGGGGACC TGCGGCGAAC TGTCGCCGCT CGGCACTTCG TGGTCTGCCA   420
CCAGCCGACC GCACTTACTG TTTTGATGGC TTTGCCGGCT GCCGTTTTGC CGCCGAGACT   480
GGTGTGGCTC TCTATTCTCT CCATGACTTG CAGCCGGCTG ATGTTGCCGA GGCGATGGCT   540
CGCCACGGCA TGACCCGCCT TTATGCAGCT TTCCACTTGC CTCCAGAGGT GCTCCTGCCT   600
CCTGGCACCT ACCGGACATC ATCCTACTTG CTGATCCACG ATGGTAAGCG CGCGGTTGTC   660
ACTTATGAGG GTGACACTAG CGCCGGTTAC AATCATGATG TTGCCACCCT CCGCACATGG   720
ATCAGGTCAA CTAAGGTTGT GGGTGAACAC CCTTTGGTGA TCGAGCGGGT GCGGGGTATT   780
GGCTGTCACT TTGTGTTGTT GATCACTGCG GCCCCTGAGC CCTCCCCGAT GCCCTACGTT   840
CCTTACCCGC GTTCGACGGA GGTCTATGTC CGGTCTATCT TTGGGCCCGG CGGGTCCCCG   900
TCGCTGTTCC CGACCGCTTG TGCTGTCAAG TCCACTTTTC ACGCCGTCCC CACGCACATC   960
TGGGACCGTC TCATGCTCTT TGGGGCCACC CTCGACGACC AGGCCTTTTG CTGCTCCAGG  1020
CTTATGACGT ACCTTCGTGG CATTAGCTAT AAGGTAACTG TGGGTGCCCT GGTCGCTAAT  1080
GAAGGCTGGA ATGCCACCGA GGATGCGCTC ACTGCAGTTA TTACGGCGGC TTACCTCACA  1140
ATATGTCATC AGCGTTATTT GCGGACCCAG GCGATTTCTA AGGGCATGCG CCGGCTTGAG  1200
CTTGAACATG CTCAGAAATT TATTTCACGC CTCTACAGCT GGCTATTTGA GAAGTCAGGT  1260
CGTGATTACA TCCCAGGCCG CCAGCTGCAG TTCTACGCTC AGTGCCGCCG CTGGTTATCT  1320
GCCGGGTTCC ATCTCGACCC CCGCACCTTA GTTTTTGATG AGTCAGTGCC TTGTAGCTGC  1380
CGAACCACCA TCCGGCGGAT CGCTGGAAAA TTTTGCTGTT TTATGAAGTG GCTCGGTCAG  1440
GAGTGTTCTT GTTTCCTCCA GCCCGCCGAG GGGCTGGCGG GCGACCAAGG TCATGACAAT  1500
GAGGCCTATG AAGGCTCTGA TGTTGATACT GCTGAGCCTG CCACCCTAGA CATTACAGGC  1560
TCATACATCG TGGATGGTCG GTCTCTGCAA ACTGTCTATC AAGCTCTCGA CCTGCCAGCT  1620
GACCTGGTAG CTCGCGCAGC CCGACTGTCT GCTACAGTTA CTGTTACTGA AACCTCTGGC  1680
CGTCTGGATT GCCAAACAAT GATCGGCAAT AAGACTTTTC TCACTACCTT TGTTGATGGG  1740
GCACGCCTTG AGGTTAACGG GCCTGAGCAG CTTAACCTCT CTTTTGACAG CCAGCAGTGT  1800
AGTATGGCAG CCGGCCCGTT TTGCCTCACC TATGCTGCCG TAGATGGCGG GCTGGAAGTT  1860
CATTTTTCCA CCGCTGGCCT CGAGAGCCGT GTTGTTTTCC CCCCTGGTAA TGCCCCGACT  1920
GCCCCGCCGA GTGAGGTCAC CGCCTTCTGC TCAGCTCTTT ATAGGCACAA CCGGCAGAGC  1980
CAGCGCCAGT CGGTTATTGG TAGTTTGTGG CTGCACCCTG AAGGTTTGCT CGGCCTGTTC  2040
CCGCCCTTTT CACCCGGGCA TGAGTGGCGG TCTGCTAACC CATTTTGCGG CGAGAGCACG  2100
```

```
                                            -continued
CTCTACACCC GCACTTGGTC CACAATTACA GACACACCCT TAACTGTCGG GCTAATTTCC    2160

GGTCATTTGG ATGCTGCTCC CCACTCGGGG GGGCCACCTG CTACTGCCAC AGGCCCTGCT    2220

GTAGGCTCGT CTGACTCTCC AGACCCTGAC CCGCTACCTG ATGTTACAGA TGGCTCACGC    2280

CCCTCTGGGG CCCGTCCGGC TGGCCCCAAC CCGAATGGCG TTCCGCAGCG CCGCTTACTA    2340

CACACCTACC CTGACGGCGC TAAGATCTAT GTCGGCTCCA TTTTCGAGTC TGAGTGCACC    2400

TGGCTTGTCA ACGCATCTAA CGCCGGCCAC CGCCCTGGTG GCGGGCTTTG TCATGCTTTT    2460

TTTCAGCGTT ACCCTGATTC GTTTGACGCC ACCAAGTTTG TGATGCGTGA TGGTCTTGCC    2520

GCGTATACCC TTACACCCCG GCCGATCATT CATGCGGTGG CCCCGGACTA TCGATTGGAA    2580

CATAACCCCA AGAGGCTCGA GGCTGCCTAC CGCGAGACTT GCGCCCGCCG AGGCACTGCT    2640

GCCTATCCAC TCTTAGGCGC TGGCATTTAC CAGGTGCCTG TTAGTTTGAG TTTTGATGCC    2700

TGGGAGCGGA ACCACCGCCC GTTTGACGAG CTTTACCTAA CAGAGCTGGC GGCTCGGTGG    2760

TTTGAATCCA ACCGCCCCGG TCAGCCCACG TTGAACATAA CTGAGGATAC CGCCCGTGCG    2820

GCCAACCTGG CCCTGGAGCT TGACTCCGGG AGTGAAGTAG GCCGCGCATG TGCCGGGTGT    2880

AAAGTCGAGC CTGGCGTTGT GCGGTATCAG TTTACAGCCG GTGTCCCCGG CTCTGGCAAG    2940

TCAAAGTCCG TGCAACAGGC GGATGTGGAT GTTGTTGTTG TGCCCACTCG CGAGCTTCGG    3000

AACGCTTGGC GGCGCCGGGG CTTTGCGGCA TTCACTCCGC ACACTGCGGC CCGTGTCACT    3060

AGCGGCCGTA GGGTTGTCAT TGATGAGGCC CCTTCGCTCC CCCCACACTT GCTGCTTTTA    3120

CATATGCAGC GTGCTGCATC TGTGCACCTC CTTGGGGACC CGAATCAGAT CCCCGCCATA    3180

GATTTTGAGC ACACCGGTCT GATTCCAGCA ATACGGCCGG AGTTGGTCCC GACTTCATGG    3240

TGGCATGTCA CCCACCGTTG CCCTGCAGAT GTCTGTGAGT TAGTCCGTGG TGCTTACCCT    3300

AAAATCCAGA CTACAAGTAA GGTGCTCCGT TCCCTTTTCT GGGGAGAGCC AGCTGTCGGC    3360

CAGAAGCTAG TGTTCACACA GGCTGCTAAG GCCGCGCACC CCGGATCTAT AACGGTCCAT    3420

GAGGCCCAGG GTGCCACTTT TACCACTACA ACTATAATTG CAACTGCAGA TGCCCGTGGC    3480

CTCATACAGT CCTCCCGGGC TCACGCTATA GTTGCTCTCA CTAGGCATAC TGAAAAATGT    3540

GTTATACTTG ACTCTCCCGG CCTGTTGCGT GAGGTGGGTA TCTCAGATGC CATTGTTAAT    3600

AATTTCTTCC TTTCGGGTGG CGAGGTTGGT CACCAGAGAC CATCGGTCAT TCCGCGAGGC    3660

AACCCTGACC GCAATGTTGA CGTGCTTGCG GCGTTTCCAC CTTCATGCCA AATAAGCGCC    3720

TTCCATCAGC TTGCTGAGGA GCTGGGCCAC CGGCCGGCGC CGGTGGCGGC TGTGCTACCT    3780

CCCTGCCCTG AGCTTGAGCA GGGCCTTCTC TATCTGCCAC AGGAGCTAGC CTCCTGTGAC    3840

AGTGTTGTGA CATTTGAGCT AACTGACATT GTGCACTGCC GCATGGCGGC CCCTAGCCAA    3900

AGGAAAGCTG TTTTGTCCAC GCTGGTAGGC CGGTATGGCA GACGCACAAG GCTTTATGAT    3960

GCGGGTCACA CCGATGTCCG CGCCTCCCTT GCGCGCTTTA TTCCCACTCT CGGGCGGGTT    4020

ACTGCCACCA CCTGTGAACT CTTTGAGCTT GTAGAGGCGA TGGTGGAGAA GGGCCAAGAC    4080

GGTTCAGCCG TCCTCGAGTT GGATTTGTGC AGCCGAGATG TCTCCCGCAT AACCTTTTTC    4140

CAGAAGGATT GTAACAAGTT CACGACCGGC GAGACAATTG CGCATGGCAA AGTCGGTCAG    4200

GGTATCTTCC GCTGGAGTAA GACGTTTTGT GCCCTGTTTG GCCCTGGTT CCGTGCGATT    4260

GAGAAGGCTA TTCTATCCCT TTTACCACAA GCTGTGTTCT ACGGGATGC TTATGACGAC    4320

TCAGTATTCT CTGCTGCCGT GGCTGGCGCC AGCCATGCCA TGGTGTTTGA AAATGATTTT    4380

TCTGAGTTTG ACTCGACTCA GAATAACTTT TCCCTAGGTC TTGAGTGCGC CATTATGAA    4440

GAGTGTGGTA TGCCCCAGTG GCTTGTCAGG TTGTACCATG CCGTCCGGTC GGCGTGGATC    4500
```

-continued

```
CTGCAGGCCC CAAAAGAGTC TTTGAGAGGG TTCTGGAAGA AGCATTCTGG TGAGCCGGGC    4560
AGCTTGCTCT GGAATACGGT GTGGAACATG GCAATCATTG CCCATTGCTA TGAGTTCCGG    4620
GACCTCCAGG TTGCCGCCTT CAAGGGCGAC GACTCGGTCG TCCTCTGTAG TGAATACCGC    4680
CAGAGCCCAG GCGCCGGTTC GCTTATAGCA GGCTGTGGTT TGAAGTTGAA GGCTGACTTC    4740
CGGCCGATTG GGCTGTATGC CGGGGTTGTC GTCGCCCCGG GGCTCGGGGC CCTACCCGAT    4800
GTCGTTCGAT TCGCCGGACG GCTTTCGGAG AAGAACTGGG GGCCTGATCC GGAGCGGGCA    4860
GAGCAGCTCC GCCTCGCCGT GCAGGATTTC CTCCGTAGGT TAACGAATGT GGCCCAGATT    4920
TGTGTTGAGG TGGTGTCTAG AGTTTACGGG GTTTCCCCGG GTCTGGTTCA TAACCTGATA    4980
GGCATGCTCC AGACTATTGG TGATGGTAAG GCGCATTTTA CAGAGTCTGT TAAGCCTATA    5040
CTTGACCTTA CACACTCAAT TATGCACCGG TCTGAATGAA TAACATGTGG TTTGCTGCGC    5100
CCATGGGTTC GCCACCATGC GCCCTAGGCC TCTTTTGCTG TTGTTCCTCT TGTTTCTGCC    5160
TATGTTGCCC GCGCCACCGA CCGGTCAGCC GTCTGGCCGC CGTCGTGGGC GGCGCAGCGG    5220
CGGTACCGGC GGTGGTTTCT GGGGTGACCG GGTTGATTCT CAGCCCTTCG CAATCCCCTA    5280
TATTCATCCA ACCAACCCCT TTGCCCCAGA CGTTGCCGCT GCGTCCGGGT CTGGACCTCG    5340
CCTTCGCCAA CCAGCCCGGC CACTTGGCTC CACTTGGCGA GATCAGGCCC AGCGCCCCTC    5400
CGCTGCCTCC CGTCGCCGAC CTGCCACAGC CGGGGCTGCG GCGCTGACGG CTGTGGCGCC    5460
TGCCCATGAC ACCTCACCCG TCCCGGACGT TGATTCTCGC GGTGCAATTC TACGCCGCCA    5520
GTATAATTTG TCTACTTCAC CCCTGACATC CTCTGTGGCC TCTGGCACTA ATTTAGTCCT    5580
GTATGCAGCC CCCCTTAATC CGCCTCTGCC GCTGCAGGAC GGTACTAATA CTCACATTAT    5640
GGCCACAGAG GCCTCCAATT ATGCACAGTA CCGGGTTGCC CGCGCTACTA TCCGTTACCG    5700
GCCCCTAGTG CCTAATGCAG TTGGAGGCTA TGCTATATCC ATTTCTTTCT GGCCTCAAAC    5760
AACCACAACC CCTACATCTG TTGACATGAA TTCCATTACT TCCACTGATG TCAGGATTCT    5820
TGTTCAACCT GGCATAGCAT CTGAATTGGT CATCCCAAGC GAGCGCCTTC ACTACCGCAA    5880
TCAAGGTTGG CGCTCGGTTG AGACATCTGG TGTTGCTGAG GAGGAAGCCA CCTCCGGTCT    5940
TGTCATGTTA TGCATACATG GCTCTCCAGT TAACTCCTAT ACCAATACCC CTTATACCGG    6000
TGCCCTTGGC TTACTGGACT TTGCCTTAGA GCTTGAGTTT CGCAATCTCA CCACCTGTAA    6060
CACCAATACA CGTGTGTCCC GTTACTCCAG CACTGCTCGT CACTCCGCCC GAGGGGCCGA    6120
CGGGACTGCG GAGCTGACCA CAACTGCAGC CACCAGGTTC ATGAAAGATC TCCACTTTAC    6180
CGGCCTTAAT GGGGTAGGTG AAGTCGGCCG CGGGATAGCT CTAACATTAC TTAACCTTGC    6240
TGACACGCTC CTCGGCGGGC TCCCGACAGA ATTAATTTCG TCGGCTGGCG GGCAACTGTT    6300
TTATTCCCGC CCGGTTGTCT CAGCCAATGG CGAGCCAACC GTGAAGCTCT ATACATCAGT    6360
GGAGAATGCT CAGCAGGATA AGGGTGTTGC TATCCCCCAC GATATCGATC TTGGTGATTC    6420
GCGTGTGGTC ATTCAGGATT ATGACAACCA GCATGAGCAG GATCGGCCCA CCCCGTCGCC    6480
TGCGCCATCT CGGCCTTTTT CTGTTCTCCG AGCAAATGAT GTACTTTGGC TGTCCCTCAC    6540
TGCAGCCGAG TATGACCAGT CCACTTACGG GTCGTCAACT GGCCCGGTTT ATATCTCGGA    6600
CAGCGTGACT TTGGTGAATG TTGCGACTGG CGCGCAGGCC GTAGCCCGAT CGCTTGACTG    6660
GTCCAAAGTC ACCCTCGACG GGCGGCCCCT CCCGACTGTT GAGCAATATT CCAAGACATT    6720
CTTTGTGCTC CCCCTTCGTG GCAAGCTCTC CTTTTGGGAG GCCGGCACAA CAAAAGCAGG    6780
TTATCCTTAT AATTATAATA CTACTGCTAG TGACCAGATT CTGATTGAAA ATGCTGCCGG    6840
CCATCGGGTC GCCATTTCAA CCTATACCAC CAGGCTTGGG GCCGGTCCGG TCGCCATTTC    6900
```

-continued

```
TGCGGCCGCG GTTTTGGCTC CACGCTCCGC CCTGGCTCTG CTGGAGGATA CTTTTGATTA     6960

TCCGGGGCGG GCGCACACAT TTGATGACTT CTGCCCTGAA TGCCGCGCTT TAGGCCTCCA     7020

GGGTTGTGCT TTCCAGTCAA CTGTCGCTGA GCTCCAGCGC CTTAAAGTTA AGGTGGGTAA     7080

AACTCGGGAG TTGTAGTTTA TTTGGCTGTG CCCACCTACT TATATCTGCT GATTTCCTTT     7140

ATTTCCTTTT TCTCGGTCCC GCGCTCCCTG A                                    7171
```

The above sequence was obtained from polyadenylated clones. For clarity the 3' polyA "tail" has been omitted.

The sequence above includes a partial cDNA sequence consisting of 1661 nucleotides that was identified in a previous application in this series. The previously identified partial sequence is set forth below, with certain corrections (SEQ ID NO.11). The corrections include deletion of the first 80 bases of the prior reported sequence, which are cloning artifacts; insertion of G after former position 174, of C after 270, and of GGCG after 279; change of C to T at former position 709, of GC to CG at 722–723, of CC to TT at 1238–39, and of C to G at 1606; deletion of T at former position 765; and deletion of the last 11 bases of the former sequence, which are part of a linker sequence and are not of viral origin.

Non-A Non-B T: M' Mexican Strain; SEQ ID NO.11

```
GTTGCGTGAG GTGGGTATCT CAGATGCCAT TGTTAATAAT TTCTTCCTTT CGGGTGGCGA       60  SEQ ID NO. 11:

GGTTGGTCAC CAGAGACCAT CGGTCATTCC GCGAGGCAAC CCTGACCGCA ATGTTGACGT      120

GCTTGCGGCG TTTCCACCTT CATGCCAAAT AAGCGCCTTC CATCAGCTTG CTGAGGAGCT      180

GGGCCACCGG CCGGCGCCGG TGGCGGCTGT GCTACCTCCC TGCCCTGAGC TTGAGCAGGG      240

CCTTCTCTAT CTGCCACAGG AGCTAGCCTC CTGTGACAGT GTTGTGACAT TGAGCTAAC       300

TGACATTGTG CACTGCCGCA TGGCGGCCCC TAGCCAAAGG AAAGCTGTTT TGTCCACGCT      360

GGTAGGCCGG TATGGCAGAC GCACAAGGCT TTATGATGCG GGTCACACCG ATGTCCGCGC      420

CTCCCTTGCG CGCTTTATTC CCACTCTCGG GCGGGTTACT GCCACCACCT GTGAACTCTT      480

TGAGCTTGTA GAGGCGATGG TGGAGAAGGG CCAAGACGGT TCAGCCGTCC TCGAGTTGGA      540

TTTGTGCAGC CGAGATGTCT CCCGCATAAC CTTTTTCCAG AAGGATTGTA ACAAGTTCAC      600

GACCGGCGAG ACAATTGCGC ATGGCAAAGT CGGTCAGGGT ATCTTCCGCT GGAGTAAGAC      660

CTTTTGTGCC CTGTTTGGCC CCTGGTTCCG TGCGATTGAG AAGGCTATTC TATCCCTTTT      720

ACCACAAGCT GTGTTCTACG GGATGCTTA TGACGACTCA GTATTCTCTG CTGCCGTGGC       780

TGGCGCCAGC CATGCCATGG TGTTTGAAAA TGATTTTTCT GAGTTTGACT CGACTCAGAA      840

TAACTTTTCC CTAGGTCTTG AGTGCGCCAT TATGGAAGAG TGTGGTATGC CCCAGTGGCT      900

TGTCAGGTTG TACCATGCCG TCCGGTCGGC GTGGATCCTG CAGGCCCCAA AAGAGTCTTT     960

GAGAGGGTTC TGGAAGAAGC ATTCTGGTGA GCCGGGCACG TTGCTCTGGA ATACGGTGTG    1020

GAACATGGCA ATCATTGCCC ATTGCTATGA GTTCCGGGAC CTCCAGGTTG CCGCCTTCAA    1080

GGGCGACGAC TCGGTCGTCC TCTGTAGTGA ATACCGCCAG AGCCCAGGCG CCGGTTCGCT    1140

TATAGCAGGC TGTGGTTTGA AGTTGAAGGC TGACTTCCGG CCGATTGGGC TGTATGCCGG    1200

GGTTGTCGTC GCCCCGGGGC TCGGGGCCCT ACCCGATGTC GTTCGATTCG CCGGACGGCT    1260

TTCGGAGAAG AACTGGGGGC CTGATCCGGA GCGGGCAGAG CAGCTCCGCC TCGCCGTGCA    1320

GGATTTCCTC CGTAGGTTAA CGAATGTGGC CCAGATTTGT GTTGAGGTGG TGTCTAGAGT    1380

TTACGGGGTT TCCCCGGGTC TGGTTCATAA CCTGATAGGC ATGCTCCAGA CTATTGGTGA    1440

TGGTAAGGCG CATTTTACAG AGTCTGTTAA GCCTATACTT GACCTTACAC ACTCAATTAT    1500

GCACCGGTCT GAATGAATAA CATGTGGTTT GCTGCGCCCA TGGGTTCGCC ACCATGCGCC    1560

CTAGGCCTCT TTTGC                                                     1575
```

When comparing the Burmese and Mexican strains, 75.7% identity is seen in a 7189 nucleotide overlap beginning at nucleotide 1 of the Mexican strain and nucleotide 25 of the Burmese strain.

In the same manner, a different strain of HEV was identified in an isolate obtained in Tashkent, U.S.S.R. The Tashkent sequence is given below (SEQ ID NO.12):

```
CGGGCCCCGT ACAGGTCACA ACCTGTGAGT TGTACGAGCT AGTGGAGGCC ATGGTCGAGA    60   SEQ ID. NO. 12:

AAGGCCAGGA TGGCTCCGCC GTCCTTGAGC TCGATCTCTG CAACCGTGAC GTGTCCAGGA   120

TCACCTTTTT CCAGAAAGAT TGCAATAAGT TCACCACGGG AGAGACCATC GCCCATGGTA   180

AAGTGGGCCA GGGCATTTCG GCCTGGAGTA AGACCTTCTG TGCCCTTTTC GGCCCCTGGT   240

TCCGTGCTAT TGAGAAGGCT ATTCTGGCCC TGCTCCCTCA GGGTGTGTTT TATGGGGATG   300

CCTTTGATGA CACCGTCTTC TCGGCGCGTG TGGCCGCAGC AAAGGCGTCC ATGGTGTTTG   360

AGAATGACTT TTCTGAGTTT GACTCCACCC AGAATAATTT TTCCCTGGGC CTAGAGTGTG   420

CTATTATGGA GAAGTGTGGG ATGCCGAAGT GGCTCATCCG CTTGTACCAC CTTATAAGGT   480

CTGCGTGGAT CCTGCAGGCC CCGAAGGAGT CCCTGCGAGG GTGTTGGAAG AAACACTCCG   540

GTGAGCCCGG CACTCTTCTA TGGAATACTG TCTGGAACAT GGCCGTTATC ACCCATTGTT   600

ACGATTTCCG CGATTTGCAG GTGGCTGCCT TTAAAGGTGA TGATTCGATA GTGCTTTGCA   660

GTGAGTACCG TCAGAGTCCA GGGGCTGCTG TCCTGATTGC TGGCTGTGGC TTAAAGCTGA   720

AGGTGGGTTT CCGTCCGATT GGTTTGTATG CAGGTGTTGT GGTGACCCCC GGCCTTGGCG   780

CGCTTCCCGA CGTCGTGCGC TTGTCCGGCC GGCTTACTGA GAAGAATTGG GGCCCTGGCC   840

CTGAGCGGGC GGAGCAGCTC CGCCTTGCTG TGCG                              874
```

As shown in the following comparison of sequences, the Tashkent (Tash.) sequence more closely resembles the Burma sequence than the Mexico sequence, as would be expected of two strains from more closely related geographical areas. The numbering system used in the comparison is based on the Burma sequence. As indicated previously, Burma has SEQ ID NO:6; Mexico, SEQ ID NO:10; and Tashkent, SEQ ID NO:12. The letters present in the lines between the sequences indicate conserved nucleotides.

```
                  10v       20v       30v       40v       50v       60v
-BURMA    AGGCAGACCACATATGTGGTCGATGCCATGGAGGCCCATCAGTTTATTAAGGCTCCTGGCA
                                    GCCATGGAGGCCCA CAGTT ATTAAGGCTCCTGGCA
-MEXICO                             GCCATGGAGGCCCACCAGTTCATTAAGGCTCCTGGCA 70v       80v       90v      100v      110v      120v
-BURMA    TCACTACTGCTATTGAGCAGGCTGCTCTAGCAGCGGCCAACTCTGCCCTGGCGAATGCTG
          TCACTACTGCTATTGAGCA GC GCTCTAGCAGCGGCCAACTC GCCCT GCGAATGCTG
-MEXICO   TCACTACTGCTATTGAGCAAGCAGCTCTAGCAGCGGCCAACTCCGCCCTTGCGAATGCTG 130v      140v      150v      150v      170v      180v
-BURMA    TGGTAGTTAGGCCTTTTCTCTCTCACCAGCAGATTGAGATCCTCATTAACCTAATGCAAC
          TGGT GT  GGCCTTT CT TC CA CAGCAG TTGAGATCCT AT AA CT ATGCAAC
-MEXICO   TGGTGGTCCGGCCTTTCCTTTCCCATCAGCAGGTTGAGATCCTTATAAATCTCATGCAAC 190v      200v      210v      220v      230v      240v
-BURMA    CTCGCCAGCTTGTTTTCCGCCCCGAGGTTTTCTGGAATCATCCCATCCAGCGTGTCATCC
          CTCG CAGCT GT TT CG CC GAGGTTTT TGGAATCA CC AT CA CGTGT AT C
-MEXICO   CTCGGCAGCTGGTGTTTCGTCCTGAGGTTTTTTGGAATCACCCGATTCAACGTGTTATAC 250v      260v      270v      280v      290v      300v
-BURMA    ATAACGAGCTGGAGCTTTACTGCCGCGCCCGCTCCGGCCGCTGTCTTGAAATTGGCGCCC
          ATAA GAGCT GAGC  TA TGCCG GC CGCTC GG CGCTG CTTGA ATTGG GCCC
-MEXICO   ATAATGAGCTTGAGCAGTATTGCCGTGCTCGCTCGGGTCGCTGCCTTGAGATTGGAGCCC
```

-continued

```
              310v       320v       330v       340v       350v       360v
-BURMA   ATCCCCGCTCAATAAATGATAATCCTAATGTGGTCCACCGCTGCTTCCTCCGCCCTGTTG
         A  CC CGCTC AT AATGATAATCCTAATGT  TCCA CGCTGCTT CTCC CCC GT G
-MEXICO  ACCCACGCTCCATTAATGATAATCCTAATGTCCTCCATCGCTGCTTTCTCCACCCCGTCG 370v       380v       380v       400v       410v       420v
-BURMA   GGCGTGATGTTCAGCGCTGGTATACTGCTCCCACTCGCGGGCCGGCTGCTAATTGCCGGC
         G CG GATGTTCAGCGCTGGTA AC GC CC ACT G GG CC GC GC AA TG CG C
-MEXICO  GCCGGGATGTTCAGCGCTAATACACAGCCCCGACTAGGGGACCTGCGGCGAACTGTCGCC 430v       440v       450v       460v       470v       480v
-BURMA   GTTCCGCGCTGCGCGGGCTTCCCGCTGCTGACCGCACTTACTGCCTCGACGGGTTTTCTG
         G TC GC CT CG GG CT CC  C GC GACCGCACTTACTG  T GA GG TTT C G
-MEXICO  GCTCGGCACTTCGTGGTCTGCCACCAGCCGACCGCACTTACTGTTTTGATGGCTTTGCCG 490v       500v       510v       520v       530v       540v
-BURMA   GCTGTAACTTTCCCGCCGAGACTGGCATCGCCCTCTACTCCCTTCATGATATGTCACCAT
         GCTG    TTT CCGCCGAGACTGG   T GC CTCTA TC CT CATGA TG   CC
-MEXICO  GCTGCCGTTTTGCCGCCGAGACTGGTGTGGCTCTCTATTCTCTCCATGACTTGCAGCCGG 550v       560v       570v       580v       590v       600v
-BURMA   CTGATGTCGCCGAGGCCATGTTCCGCCATGGTATGACGCGGCTCTATGCCGCCCTCCATC
         CTGATGT GCCGAGGC ATG   CGCCA GG ATGAC CG CT TATGC GC   TCCA
-MEXICO  CTGATGTTGCCGAGGCGATGGCTCGCCACGGCATGACCCGCCTTTATGCAGCTTTCCACT 610v       620v       630v       640v       650v       660v
-BURMA   TTCCGCCTGAGGTCCTGCTGCCCCCTGGCACATATCGCACCGCATCGTATTTGCTAATTC
         T CC CC GAGGT CT CTGCC CCTGGCAC TA CG AC  CATC TA TTGCT AT C
-MEXICO  TGCCTCCAGAGGTGCTCCTGCCTCCTGGCACCTACCGGACATCATCCTACTTGCTGATCC 670v       680v       690v       700v       710v       720v
-BURMA   ATGACGGTAGGCGCGTTGTGGTGACGTATGAGGGTGATACTAGTGCTGGTTACAACCACG
         A GA GGTA GCGCG  GT GT AC TATGAGGGTGA ACTAG GC GGTTACAA CA G
-MEXICO  ACGATGGTAAGCGCGCGGTTGTCACTTATGAGGGTGACACTAGCGCCGGTTACAATCATG 730v       740v       750v       750v       770v       780v
-BURMA   ATGTCTCCAACTTGCGCTCCTGGATTAGAACCACCAAGGTTACCGGAGACCATCCCCTCG
         ATGT    CCA C T CGC C  TGGAT AG AC AC AAGGTT    GG GA CA CC   T G
-MEXICO  ATGTTGCCACCCTCCGCACATGGATCAGGACAACTAAGGTTGTGGGTGAACACCCTTTGG 790v       800v       810v       820v       830v       840v
-BURMA   TTATCGAGCGGGTTAGGGCCATTGGCTGCCACTTTGTTCTCTTGCTCACGGCAGCCCCGG
         T ATCGAGCGGGT  GGG  ATTGGCTG CACTTTGT  T TTG TCAC GC GCCCC G
-MEXICO  TGATCGAGCGGGTGCGGGGTATTGGCTGTCACTTTGTGTTGTTGATCACTGCGGCCCCTG 850v       860v       870v       880v       890v       900v
-BURMA   AGCCATCACCTATGCCTTATGTTCCTTACCCCCGGTCTACCGAGGTCTATGTCCGATCGA
         AGCC TC CC ATGCC TA GTTCCTTACCC CG TC AC GAGGTCTATGTCCG TC A
-MEXICO  AGCCCTCCCCGATGCCCTACGTTCCTTACCCGCGTTCGACGGAGGTCTATGTCCGGTCTA 910v       920v       930v       940v       950v       960v
-BURMA   TCTTCGGCCCGGGTGGCACCCCTTCCTTATTCCCAACCTCATGCTCCACTAAGTCGACCT
         TCTT GG CC GG GG  CCCC TC  T TTCCC ACC C TG  C    AAGTC AC T
-MEXICO  TCTTTGGGCCCGGCGGGTCCCCGTCGCTGTTCCCGACCGCTTGTGCTGTCAAGTCCACTT 970v       980v       990v       1000v      1010v      1020v
-BURMA   TCCATGCTGTCCCTGCCCATATTTGGGACCGTCTTATGCTGTTCGGGGCCACCTTGGATG
         T CA GC GTCCC  C CA AT TGGGACCGTCT ATGCT TT GGGGCCACC T GA G
-MEXICO  TTCACGCCGTCCCCACGCACATCTGGGACCGTCTCATGCTCTTTGGGGCCACCCTCGACG 1030v      1040v      1050v      1060v      1070v      1080v
-BURMA   ACCAAGCCTTTTGCTGCTCCCGTTTAATGACCTACCTTCGCGGCATTAGCTACAAGGTCA
         ACCA GCCTTTTGCTGCTCC  G  T ATGAC TACCTTCG GGCATTAGCTA AAGGT A
-MEXICO  ACCAGGCCTTTTGCTGCTCCAGGCTTATGACGTACCTTCGTGGCATTAGCTATAAGGTAA 1090v      1100v      1110v      1120v      1130v      1140v
-BURMA   CTGTTGGTACCCTTGTGGCTAATGAAGGCTGGAATGCCTCTGAGGACGCCCTCACAGCTG
         CTGT GGT CCCT GT GCTAATGAAGGCTGGAATGCC C GAGGA GC CTCAC GC G
-MEXICO  CTGTGGGTGCCCTGGTCGCTAATGAAGGCTGGAATGCCACCGAGGATGCGCTCACTGCAG 1150v      1160v      1170v      1180v      1190v      1200v
-BURMA   TTATCACTGCCGCCTACCTTACCATTTGCCACCAGCGGTATCTCCGCACCCAGGCTATAT
         TTAT AC GC GC TACCT AC AT TG CA CAGCG TAT T CG ACCCAGGC AT T
-MEXICO  TTATTACGGCGGCTTACCTCACAATATGTCATCAGCGTTATTTGCGGACCCAGGCGATTT 1210v      1220v      1230v      1240v      1250v      1260v
-BURMA   CCAAGGGGATGCGTCGTCTGGAACGGGAGCATGCCCAGAAGTTTATAACACGCCTCTACA
         C AAGGG ATGCG CG CT GA C  GA CATGC CAGAA TTTAT  CACGCCTCTACA
-MEXICO  CTAAGGGCATGCGCCGGCTTGAGCTTGAACATGCTCAGAAATTTATTTCACGCCTCTACA
```

```
                          -continued
               1270v    1280v    1290v    1300v    1310v    1320v
-BURMA         GCTGGCTCTTCGAGAAGTCCGGCCGTGATTACATCCCTGGCCGTCAGTTGGAGTTCTACG
               GCTGGCT TT GAGAAGTC GG CGTGATTACATCCC GGCCG CAG TG AGTTCTACG
-MEXICO        GCTGGCTATTTGAGAAGTCAGGTCGTGATTACATCCCAGGCCGCCAGCTGACGTTCTACG 1330v    1340v    1350v    1360v    1370v    1380v
-BURMA         CCCAGTGCAGGCGCTGGCTCTCCGCCGGCTTTCATCTTGATCCACGGGTGTTGGTTTTTG
               C CAGTGC G CGCTGG T TC GCCGG TT CATCT GA CC CG    TT GTTTTTG
-MEXICO        CTCAGTGCCGCCGCTGGTTATCTGCCGGGTTCCATCTCGACCCCCGCACCTTAGTTTTTG 1390v    1400v    1410v    1420v    1430v    1440v
-BURMA         ACGAGTCGGCCCCCTGCCATTGTAGGACCGCGATCCGTAAGGCGCTCTCAAAGTTTTGCT
               A GAGTC G  CC TG   TG G ACC C ATCCG   G       AAA TTTTGCT
-MEXICO        ATGAGTCAGTGCCTTGTAGCTGCCGAACCACCATCCGGCGGATCGCTGGAAAATTTTGCT 1450v    1460v    1470v    1480v    1490v    1500v
-BURMA         GCTTCATGAAGTGGCTTGGTCAGGAGTGCACCTGCTTCCTTCAGCCTGCAGAAGGCGCCG
               G TT ATGAAGTGGCT GGTCAGGAGTG  C TG TTCCT CAGCC GC GA GG     G
-MEXICO        GTTTTATGAAGTGGCTCGGTCAGGAGTGTTCTTGTTTCCTCCAGCCCGCCGAGGGGCTGG 1510v    1520v    1530v    1540v    1550v    1560v
-BURMA         TCGGCGACCAGGGTCATGATAATGAAGCCTATGAGGGGTCCGATGTTGACCCTGCTGAGT
                 GGCGACCA GGTCATGA AATGA GCCTATGA GG TC GATGTTGA CTGCTGAG
-MEXICO        CGGGCGACCAAGGTCATGACAATGAGGCCTATGAAGGCTCTGATGTTGATACTGCTGAGC 1570v    1580v    1590v    1600v    1610v    1620v
-BURMA         CCGCCATTAGTGACATATCTGGGTCCTATGTCGTCCCTGGCACTGCCCTCCAACCGCTCT
               C GCCA     GACAT  C GG TC TA  TCGT    TGG     C CT CAA C TCT
-MEXICO        CTGCCACCCTAGACATTACAGGCTCATACATCGTGGATGGTCGGTCTCTGCAAACTGTCT 1630v    1640v    1650v    1660v    1670v    1680v
-BURMA         ACCAGGCCCTCGATCTCCCCGCTGAGATTGTGGCTCGCGCGGGCCGGCTGACCGCCACAG
               A CA GC CTCGA CT CC GCTGA   T GT GCTCGCGC G CCG CTG C GC ACAG
-MEXICO        ATCAAGCTCTCGACCTGCCAGCTGACCTGGTAGCTCGCGCAGCCCGACTGTCTGCTACAG 1690v    1700v    1710v    1720v    1730v    1740v
-BURMA         TAAAGGTCTCCCAGGTCGATGGGCGGATCGATTGCGAGACCCTTCTTGGTAACAAAACCT
               T A  GT  C  A    C  TGG CG  T GATTGC A AC   T  T GG AA AA AC T
-MEXICO        TTACTGTTACTGAAACCTCTGGCCGTCTGGATTGCCAAACAATGATCGGCAATAAGACTT 1750v    1760v    1770v    1780v    1790v    1800v
-BURMA         TTCGCACCTCGTTCGTTGACGGGGCGGTCTTAGAGACCAATGGCCCAGAGCGCCACAATC
               TTC CAC  C TT GTTGA GGGGC   C T GAG    AA GG CC GAGC   C  AA C
-MEXICO        TTCTCACTACCTTTGTTGATGGGGCACGCCTTGAGGTTAACGGGCCTGAGCAGCTTAACC 1810v    1820v    1830v    1840v    1850v    1860v
-BURMA         TCTCCTTCGATGCCAGTCAGAGCACTATGGCCGCTGGCCCTTTCAGTCTCACCTATGCCG
               TCTC TT GA   C   CAG G A TATGGC GC GGCCC TT  G CTCACCTATGC G
-MEXICO        TCTCTTTTGACAGCCAGCAGTGTAGTATGGCAGCCGGCCCGTTTTGCCTCACCTATGCTG 1870v    1880v    1890v    1900v    1910v    1920v
-BURMA         CCTCTGCAGCTGGGCTGGAGGTGCGCTATGTTGCTGCCGGGCTTGACCATCGGGCGGTTT
               CC   G  G  GGGCTGGA GT C  T T    C GC GG CT GA    CG G  GTTT
-MEXICO        CCGTAGATGGCGGGCTGGAAGTTCATTTTTCCACCGCTGGCCTCGAGAGCCGTGTTGTTT 1930v    1940v    1950v    1960v    1970v    1980v
-BURMA         TTGCCCCCGGTGTTTCACCCCGGTCAGCCCCCGGCGAGGTTACCGCCTTCTGCTCTGCCC
               T  CCCC GGT  T C CC     C  C CC  G GAGGT ACCGCCTTCTGCTC GC C
-MEXICO        TCCCCCCTGGTAATGCCCCGACTGCCCCGCCGAGTGAGGTCACCGCCTTCTGCTCAGCTC 1990v    2000v    2010v    2020v    2030v    2040v
-BURMA         TATACAGGTTTAACCGTGAGGCCCAGCGCCATTCGCTGATCGGTAACTTATGGTTCCATC
               T TA AGG    AACCG  AG  CCAGCGCCA TCG T AT GGTA  TT TGG T CA C
-MEXICO        TTTATAGGCACAACCGGCAGAGCCAGCGCCAGTCGGTTATTGGTAGTTTGTGGCTGCACC 2050v    2060v    2070v    2080v    2090v    2100v
-BURMA         CTGAGGGACTCATTGGCCTCTTCGCCCCGTTTTCGCCCGGGCATGTTTGGGAGTCGGCTA
               CTGA GG   T   T GGCCT TTC C  CC  TTTTC CCCGGGCATG   TGG  GTC GCTA
-MEXICO        CTGAAGGTTTGCTCGGCCTGTTCCCGCCCTTTTCACCCGGGCATGAGTGGCGGTCTGCTA 2110v    2120v    2130v    2140v    2150v    2160v
-BURMA         ATCCATTCTGTGGCGAGAGCACACTTTACACCCGTACTTGGTCGGAGGTTGATGCCGTCT
               A CCATT TG  GGCGAGAGCAC CT TACACCCG ACTTGGTC      TT    G C
-MEXICO        ACCCATTTTGCGGCGAGAGCACGCTCTACACCCGCACTTGGTCCACAATTACAGACACAC 2170v    2180v    2190v    2200v    2210v    2220v
-BURMA         CTAGTCCAGCCCGGCCTGACTTAGGTTTTATGTCTGAGCCTTCTATACCTAGTAGGGCCG
               C    CG C GGC    T  GGT T TG TG   CT C     C  G GG C
-MEXICO        CCTTAACTGTCGGGCTAATTTCCGGTCATTTGGATGCTGCTCCCCACTCGGGGGGCCAC
```

```
                    -continued
             2230v      2240v      2250v      2260v      2270v      2280v
-BURMA       CCACGCCTACCCTGGCGGCCCCTCTACCCCCCCCTGCACCGGACCCTTCCCCCCCTCCCT
             C  C   CT CC    G   C  CT TA  C C  CTG    C        C   CCC C
-MEXICO      CTGCTACTGCCACAGGCCCTGCTGTAGGCTCGTCTGACTCTCCAGACCCTGACCCGCTAC 2290v      2300v      2310v      2320v      2330v      2340v
-BURMA       CTGCCCCGGCGCTTGCTGAGCCGGCTTCTGGCGCTACCGCCGGGGCCCCGGCCATAACTC
             CTG       C   TG     C   C TCTGG GC       C G  G CCC    C   A T
-MEXICO      CTGATGTTACAGATGGCTCACGCCCCTCTGGGGCCCGTCCGGCTGGCCCCAACCCGAATG 2350v      2360v      2370v      2380v      2390v      2400v
-BURMA       ACCAGACGGCCCGGCACCGCCGCCTGCTCTTCACCTACCCGGATGGCTCTAAGGTATTCG
              C    CG           CGCCGC T CT     CACCTACCC  GA  GGC  CTAAG T  T    G
-MEXICO      GCGTTCCGCAG------CGCCGCTTACTACACACCTACCCTGACGGCGCTAAGATCTATG 2410v      2420v      2430v      2440v      2450v      2460v
-BURMA       CCGGCTCGCTGTTCGAGTCGACATGCACGTGGCTCGTTAACGCGTCTAATGTTGACCACC
              CGGCTC   T  TTCGAGTC    TGCAC  TGGCT  GT  AACGC  TCTAA  G   G CCACC
-MEXICO      TCGGCTCCATTTTCGAGTCTGAGTGCACCTGGCTTGTCAACGCATCTAACGCCGGCCACC 2470v      2480v      2490v      2500v      2510v      2520v
-BURMA       GCCCTGGCGGCGGGCTTTGCCATGCATTTTACCAAAGGTACCCCGCCTCCTTTGATGCTG
             GCCCTGG  GGCGGGCTTT   CATGC TTTT   CA  G TACCC  G  TC TTTGA GC
-MEXICO      GCCCTGGTGGCGGGCTTTGTCATGCTTTTTTTCAGCGTTACCCTGATTCGTTTGACGCCA 2530v      2540v      2550v      2560v      2570v      2580v
-BURMA       CCTCTTTTGTGATGCGCGACGGCGCGGCCGCGTACACACTAACCCCCCGGCCAATAATTC
             CC    TTTGTGATGCG GA GG      GCCGCGTA AC CT AC CCCCGGCC AT ATTC
-MEXICO      CCAAGTTTGTGATGCGTGATGGTCTTGCCGCGTATACCCTTACACCCCGGCCGATCATTC 2590v      2600v      2610v      2620v      2630v      2640v
-BURMA       ACGCTGTCGCCCCTGATTATAGGTTGGAACATAACCCAAAGAGGCTTGAGGCTGCTTATC
             A GC GT GCCCC GA TAT G TTGGAACATAACCC AAGAGGCT GAGGCTGC TA C
-MEXICO      ATGCGGTGGCCCCGGACTATGGATTGGAACATAACCCCAAGAGGCTCGAGGCTGCCTACC 2650v      2660v      2670v      2680v      2690v      2700v
-BURMA       GGGAAACTTGCTCCCGCCTCGGCACCGCTGCATACCCGCTCCTCGGGACCGGCATATACC
             G GA ACTTGC CCCGCC   GGCAC GCTGC TA CC CTC T GG  C GGCAT TACC
-MEXICO      GCGAGACTTGCGCCCGCCGAGGCACTGCTGCCTATCCACTCTTAGGCGCTGGCATTTACC 2710v      2720v      2730v      2740v      2750v      2760v
-BURMA       AGGTGCCGATCGGCCCCAGTTTTGACGCCTGGGAGCGGAACCACCGCCCCGGGGATGAGT
             AGGTGCC  T  G    AGTTTTGA GCCTGGGAGCGGAACCACCGCCC     GA GAG
-MEXICO      AGGTGCCTGTTAGTTTGAGTTTTGATGCCTGGGAGCGGAACCACCGCCCGTTTGACGAGC 2770v      2780v      2790v      2800v      2810v      2820v
-BURMA       TGTACCTTCCTGAGCTTGCTGCCAGATGGTTTGAGGCCAATAGGCCGACCCGCCCGACTC
             T TACCT  C GAGCT GC GC  G TGGTTTGA  CCAA  G CC     C  CC AC
-MEXICO      TTTACCTAACAGAGCTGGCGGCTCGGTGGTTTGAATCCAACCGCCCCGGTCAGCCCACGT 2830v      2840v      2850v      2860v      2870v      2880v
-BURMA       TCACTATAACTGAGGATGTTGCACGGACAGCGAATCTGGCCATCGAGCTTGACTCAGCCA
             T A  ATAACTGAGGAT   GC CG  C GC AA  CTGGCC T GAGCTTGACTC G  A
-MEXICO      TGAACATAACTGAGGATACGGCCCGTGCGGCCAACCTGGCCCTGGAGCTTGACTCCGGGA 2890v      2900v      2910v      2920v      2930v      2940v
-BURMA       CAGATGTCGGCCGGGCCTGTGCCGGCTGTCGGGTCACCCCCGGCGTTGTTCAGTACCAGT
                  GA GT GGCCG GC TGTGCCGG TGT     GTC    CC GGCGTTGT C GTA CAGT
-MEXICO      GTGAAGTAGGCCGCGCATGTGCCGGGTGTAAAGTCGAGCCTGGCGTTGTGCGGTATCAGT 2950v      2960v      2970v      2980v      2990v      3000v
-BURMA       TTACTGCAGGTGTGCCTGGATCCGGCAAGTCCCGCTCTATCACCCAAGCCGATGTGGACG
             TTAC GC GGTGT CC GG TC GGCAAGTC     TC  T    CA GC GATGTGGA G
-MEXICO      TTACAGCCGGTGTCCCCGGCTCTGGCAAGTCAAAGTCCGTGCAACAGGCGGATGTGGATG 3010v      3020v      3030v      3040v      3050v      3050v
-BURMA       TTGTCGTGGTCCCGACGCGTGAGTTGCGTAATGCCTGGCGCCGTCGCGGCTTTGCTGCTT
             TTGT GT GT CC AC CG GAG T CG AA  GC TGGCG CG CG GGCTTTGC GC T
-MEXICO      TTGTTGTTGTGCCCACTCGCGAGCTTCGGAACGCTTGGCGGCGCCGGGGCTTTGCGGCAT 3070v      3080v      3090v      3100v      3110v      3120v
-BURMA       TTACCCCGCATACTGCCGCCAGAGTCACCCAGGGGCGCCGGGTTGTCATTGATGAGGCTC
             T AC  CCGCA  ACTGC GCC G GTCAC    GG CG  GGGTTGTCATTGATGAGGC  C
-MEXICO      TCACTCCGCACACTGCGGCCCGTGTCACTAGCGGCCGTACCCTTGTCATTGATGAGGCCC 3130v      3140v      3150v      3160v      3170v      3180v
-BURMA       CATCCCTCCCCCCTCACCTGCTGCTGCTCCACATGCAGCGGGCCGCCACCGTCCACCTTC
             C  TC CTCCCCCC CAC TGCTGCT  T CA ATGCAGCG GC GC   C GT CACCT C
-MEXICO      CTTCGCTCCCCCCACACTTGCTGCTTTTACATATGCAGCGTGCTGCATCTGTGCACCTCC
```

-continued

```
                  3190v      3200v      3210v      3220v      3230y      3240v
-BURMA    TTGGCGACCCGAACCAGATCCCAGCCATCGACTTTGAGCACGCTGGGCTCGTCCCCGCCA
          TTGG GACCCGAA CAGATCCC GCCAT GA TTTGAGCAC C GG CT  T CC GC A
-MEXICO   TTGGGGACCCGAATCAGATCCCCGCCATAGATTTTGAGCACACCGGTCTGATTCCAGCAA 3250v      3250v      3270v      3280v      3290v      3300v
-BURMA    TCAGGCCCGACTTAGGCCCCACCTCCTGGTGGCATGTTACCCATCGCTGGCCTGCGGATG
          T   GGCC GA TT G CCC AC TC TGGTGGCATGT ACCCA CG TG CCTGC GATG
-MEXICO   TACGGCCGGAGTTGGTCCCGACTTCATGGTGGCATGTCACCCACCGTTGCCCTGCAGATG 3310v      3320v      3330v      3340v      3350v      3360v
-BURMA    TATGCGAGCTCATCCGTGGTGCATACCCCATGATCCAGACCACTAGCCGGGTTCTCCGTT
          T TG GAG T  TCCGTGGTGC TACCC A  ATCCAGAC AC AG   GGT CTCCGTT
-MEXICO   TCTGTGAGTTAGTCCGTGGTGCTTACCCTAAAATCCAGACTACAAGTAAGGTGCTCCGTT 3370v      3380v      3390v      3400v      3410v      3420v
-BURMA    CGTTGTTCTGGGGTGAGCCTGCCGTCGGGCAGAAACTAGTGTTCACCCAGGCGGCCAAGC
          C  T TTCTGGGG GAGCC GC GTCGG CAGAA CTAGTGTTCAC CAGGC GC AAG
-MEXICO   CCCTTTTCTGGGGAGAGCCAGCTGTCGGCCAGAAGCTAGTGTTCACACAGGCTGCTAAGG 3430v      3440v      3450v      3460v      3470v      3480v
-BURMA    CCGCCAACCCCGGCTCAGTGACGGTCCACGAGGCGCAGGGCGCTACCTACACGGAGACCA
          CCGC  ACCCCGG TC  T ACGGTCCA GAGGC CAGGG GC AC T  AC    AC A
-MEXICO   CCGCGCACCCCGGATCTATAACGGTCCATGAGGCCCAGGGTGCCACTTTTACCACTACAA 3490v      3500v      3510v      3520v      3530v      3540v
-BURMA    CTATTATTGCCACAGCAGATGCCCGGGGCCTTATTCAGTCGTCTCGGGCTCATGCCATTG
          CTAT ATTGC AC GCAGATGCCCG GGCCT AT CAGTC TC CGGGCTCA GC AT G
-MEXICO   CTATAATTGCAACTGCAGATGCCCGTGGCCTCATACAGTCCTCCCGGGCTCACGCTATAG 3550v      3560v      3570v      3580v      3590v      3600v
-BURMA    TTGCTCTGACGCGCCACACTGAGAAGTGCGTCATCATTGACGCACCAGGCCTGCTTCGCG
          TTGCTCT AC  G CA ACTGA AA TG GT AT   TTGAC C CC GGCCTG T CG G
-MEXICO   TTGCTCTCACTAGGCATACTGAAAAATGTGTTATACTTGACTCTCCCGGCCTGTTGCGTG 3610v      3620v      3630v      3640v      3650v      3660v
-BURMA    AGGTGGGCATCTCCGATGCAATCGTTAATAACTTTTTCCTCGCTGGTGGCGAAATTGGTC
          AGGTGGG ATCTC GATGC AT GTTAATAA TT TTCCT  C GGTGGCGA  TTGGTC
-MEXICO   AGGTGGGTATCTCAGATGCCATTGTTAATAATTTCTTCCTTTCGGGTGGCGAGGTTGGTC 3670v      3680v      3690v      3700v      3710v      3720v
-BURMA    ACCAGCGCCCATCAGTTATTCCCCGTGGCAACCCTGACGCCAATGTTGACACCCTGGCTG
          ACCAG G CCATC GT ATTCC CG GGCAACCCTGAC  CAATGTTGAC   CT GC G
-MEXICO   ACCAGAGACCATCGGTCATTCCGCGAGGCAACCCTGACCGCAATGTTGACGTGCTTGCGG 3730v      3740v      3750v      3760v      3770v      3780v
-BURMA    CCTTCCCGCCGTCTTGCCAGATTAGTGCCTTCCATCAGTTGGCTGAGGAGCTTGGCCACA
          C TT CC CC TC TGCCA AT AG GCCTTCCATCAG T GCTGAGGAGCT GGCCAC
-MEXICO   CGTTTCCACCTTCATGCCAAATAAGCGCCTTCCATCAGCTTGCTGAGGAGCTGGGCCACC 3790v      3800v      3810v      3820v      3830v      3840v
-BURMA    GACCTGTCCCTGTTGCAGCTGTTCTACCACCCTGCCCCGAGCTCGAACAGGGCCTTCTCT
          G CC G   CC GT GC GCTGT CTACC CCCTGCCC GAGCT GA CAGGGCCTTCTCT
-MEXICO   GGCCGGCGCCGGTGGCGGCTGTGCTACCTCCCTGCCCTGAGCTTGAGCAGGGCCTTCTCT 3850v      3860v      3370v      3880v      3890v      3900v
-BURMA    ACCTGCCCCAGGAGCTCACCACCTGTGATAGTGTCGTAACATTTGAATTAACAGACATTG
          A CTGCC CAGGAGCT  CC CCTGTCA AGTGT GT ACATTTGA  TAAC GACATTG
-MEXICO   ATCTGCCACAGGAGCTAGCCTCCTGTGACAGTGTTGTGACATTTGAGCTAACTGACATTG 3910v      3920v      3930v      3940v      3950v      3960v
-BURMA    TGCACTGCCGCATGGCCGCCCCGAGCCAGCGCAAGGCCGTGCTGTCCACACTCGTGGGCC
          TGCACTGCCGCATGGC GCCCC AGCCA  G AA GC GT  TGTCCAC CT GT GGCC
-MEXICO   TGCACTGCCGCATGGCGGCCCCTAGCCAAAGGAAAGCTGTTTTGTCCACGCTGGTAGGCC 3970v      3980v      3990v      4000v      4010v      4020v
-BURMA    GCTACGGCGGTCGCACAAAGCTCTACAATGCTTCCCACTCTGATGTTCGCGACTCTCTCG
          G  TA GGC G CGCACAA GCT  TA ATGC   CAC C GATGT CGCG CTC CT G
-MEXICO   GGTATGGCAGACGCACAAGGCTTTATGATGCGGGTCACACCGATGTCCGCGCCTCCCTTG 4030v      4040v      4050v      4060v      4070v      4080v
-TASHKENT                    GGCCCCGTACAGGTCACAACCTGTGAGTTGTACGAGCTAG
                             GGCCCCGTACAGGT ACAAC TGTGA TTGTACGAGCTAG
-BURMA    CCCGTTTTATCCCGGCCATTGGCCCCGTACAGGTTACAACTTGTGAATTGTACGAGCTAG
          C CG TTTAT CC  C  T GG C  GT    G  AC AC TGTGAA T T  GAGCT G
-MEXICO   CGCGCTTTATTCCCACTCTCGGGCGGGTTACTGCCACCACCTGTGAACTCTTTGAGCTTG 4090v      4100v      4110v      4120v      4130v      4140v
-TASHKENT TGGAGGCCATGGTCGAGAAAGGCCAGGATGGCTCCGCCGTCCTTGAGCTCGATCTCTGCA
          TGGAGGCCATGGTCGAGAA GGCCAGGATGGCTCCGCCGTCCTTGAGCT GATCT TGCA
```

```
                                          -continued
-BURMA      TGGAGGCCATGGTCGAGAAGGGCCAGGATGGCTCCGCCGTCCTTGAGCTTGATCTTTGCA
            T GAGGC ATGGT GAGAAGGGCCA GA GG TC GCCGTCCT GAG T GAT T TGCA
-MEXICO     TAGAGGCGATGGTGGAGAAGGGCCAAGACGGTTCAGCCGTCCTCGAGTTGGATTTGTGCA 4150v     4150v     4170v     4180v     4190v     4200v
-TASHKENT   ACCGTGACGTGTCCAGGATCACCTTTTTCCAGAAAGATTGCAATAAGTTCACCACGGGAG
            ACCGTGACGTGTCCAGGATCACCTT TTCCAGAAAGATTG AA AAGTTCACCAC GG G
-BURMA      ACCGTGACGTGTCCAGGATCACCTTCTTCCAGAAAGATTGTAACAAGTTCACCACAGGTG
              CCG GA GT TCC G AT ACCTT TTCCAGAA GATTGTAACAAGTTCAC AC GG G
-MEXICO     GCCGAGATGTCTCCCGCATAACCTTTTTCCAGAAGGATTGTAACAAGTTCACGACCGGCG 4210v     4220v     4230v     4240v     4250v     4260v
-TASHKENT   AGACCATCGCCCATGGTAAAGTGGGCCAGGGCATTTCGGCCTGGAGTAAGACCTTCTGTG
            AGACCAT GCCCATGGTAAAGTGGGCCAGGGCATTTCGGCCTGGAG AAGACCTTCTG G
-BURMA      AGACCATTGCCCATGGTAAAGTGGGCCAGGGCATCTCGGCCTGGAGCAAGACCTTCTGCG
             AGAC ATTGC CATGG AAAGT GG CAGGG ATCT   CTGGAG AAGAC TT TG G
-MEXICO     AGACAATTGCGCATGGCAAAGTCGGTCAGGGTATCTTCCGCTGGAGTAAGACGTTTTGTG 4270v     4280v     4290v     4300v     4310v     4320v
-TASHKENT   CCCTTTTCGGCCCCTGGTTCCGTGCTATTGAGAAGGCTATTCTGGCCCTGCTCCCTCAGG
             CCCT TT GGCCC TGGTTCCG GCTATTGAGAAGGCTATTCTGGCCCTGCTCCCTCAGG
-BURMA      CCCTCTTTGGCCCTTGGTTCCGCGCTATTGAGAAGGCTATTCTGGCCCTGCTCCCTCAGG
             CCCT TTTGGCCC TGGTTCCG GC ATTGAGAAGGCTATTCT   CCCT  T CC CA G
-MEXICO     CCCTGTTTGCCCCTGGTTCCGTGCGATTGAGAAGGCTATTCTATCCCTTTTACCACAAG 4330v     4340v     4350v     4360v     4370v     4380v
-TASHKENT   GTGTGTTTTATGGGGATGCCTTTGATGACACCGTCTTCTCGGCGCGTGTGGCCGCAGCAA
            GTGTGTTTTA GG GATGCCTTTGATGACACCGTCTTCTCGGCG TGTGGCCGCAGCAA
-BURMA      GTGTGTTTTACGGTGATGCCTTTGATGACACCGTCTTCTCGGCGGCTGTGGCCGCAGCAA
             TGTGTT TACGG GATGC T TGA GAC C GT TTCTC GC GC GTGGC G  GC A
-MEXICO     CTGTGTTCTACGGGGATGCTTATGACGACTCAGTATTCTCTGCTGCCGTGGCTGGCGCCA 4390v     4400v     4410v     4420v     4430v     4440v
-TASHKENT   AGGCGTCCATGGTGTTTGAGAATGACTTTTCTGAGTTTGACTCCACCCAGAATAATTTTT
            AGGC TCCATGGTGTTTGAGAATGACTTTTCTGAGTTTGACTCCACCCAGAATAA TTTT
-BURMA      AGGCATCCATGGTGTTTGAGAATGACTTTTCTGAGTTTGACTCCACCCAGAATAACTTTT
                  CCATGGTGTTTGA AATGA TTTTCTGAGTTTGACTC AC CAGAATAACTTTT
-MEXICO     GCCATGCCATGGTGTTTGAAAATGATTTTTCTGAGTTTGACTGACTCAGAATAACTTTT 4450v     4460v     4470v     4480v     4490v     4500v
-TASHKENT   CCCTGGGCCTAGAGTGTGCTATTATGGAGAAGTGTGGGATGCCGAAGTGGCTCATCCGCT
            C CTGGG CTAGAGTGTGCTATTATGGAG AGTGTGGGATGCCG AGTGGCTCATCCGC
-BURMA      CTCTGGGTCTAGAGTGTGCTATTATGGAGGAGTGTGGGATGCCGCAGTGGCTCATCCGCC
            C CT GGTCT GAGTG GC ATTATGGA GAGTGTGG ATGCC CAGTGGCT  TC G
-MEXICO     CCCTAGGTCTTGAGTGCGCCATTATGGAAGAGTGTGGTATGCCCCAGTGGCTTGTCAGGT 4510v     4520v     4530v     4540v     4550v     4560v
-TASHKENT   TGTACCACCTTATAAGGTCTGCGTGGATCCTGCAGGCCCCGAAGGAGTCCCTGCGAGGGT
            TGTA CACCTTATAAGGTCTGCGTGGATC TGCAGGCCCCGAAGGAGTC CTGCGAGGGT
-BURMA      TGTATCACCTTATAAGGTCTGCGTGGATCTTGCAGGCCCCGAAGGAGTCTCTGCGAGGGT
            TGTA CA     T  GGTC GCGTGGATC TGCAGGCCCC AA GAGTCT TG GAGGGT
-MEXICO     TGTACCATGCCGTCCGGTCGGCGTGGATCCTGCAGGCCCCAAAAGAGTCTTTGAGAGGGT 4570v     4580v     4590v     4600v     4610v     4620v
-TASHKENT   GTTGGAAGAAACACTCCGGTGAGCCCGGCACTCTTCTATGGAATACTGTCTGGAACATGG
             TTGGAAGAAACACTCCGGTGAGCCCGGCACTCTTCTATGGAATACTGTCTGGAA ATGG
-BURMA      TTTGGAAGAAACACTCCGGTGAGCCCGGCACTCTTCTATGGAATACTGTCTGGAATATGG
            T TGGAAGAA CA TC GGTGAGCC GGCA   T CT TGGAATAC GT TGGAA ATGG
-MEXICO     TCTGGAAGAAGCATTCTGGTGAGCCGGGCAGCTTGCTCTGGAATACGGTGTGGAACATGG 4630v     4640v     4650v     4660v     4670v     4680v
-TASKENT    CCGTTATCACCCATTGTTACGATTTCCGCGATTTGCAGGTGGCTGCCTTTAAAGGTGATG
            CCGTTAT ACCCA TGTTA GA TTCCGCGATTT  AGGTGGCTGCCTTTAAAGGTGATG
-BURMA      CCGTTATTACCCACTGTTATGACTTCCGCGATTTTCAGGTGGCTGCCTTTAAAGGTGATG
            C  T ATT CCCA TG TATGA TTCCG GA  T CAGGT GC GCCTT AA GG GA G
-MEXICO     CAATCATTGCCCATTGCTATGAGTTCCGGGACCTCCAGGTTGCCGCCTTCAAGGGCGACG 4690v     4700v     4710v     4720v     4730v     4740v
-TASHKENT   ATTCGATAGTGCTTTGCAGTGAGTACCGTCAGAGTCCAGGGGATGCTGTCCTGATTGCTG
            ATTCGATAGTGCTTTGCAGTGAGTA CGTCAGAGTCCAGG GCTGTCTCCTGAT GC CG
-BURMA      ATTCGATAGTGCTTTGCAGTGAGTATCGTCAGAGTCCAGGAGCTGCTGTCCTGATCGCCG
              A TCG T GT CT TG AGTGA TA CG CAGAG CCAGG GC G T  CT AT GC G
-MEXICO     ACTCGGTCGTCCTGTGTAGTGAATACCGCCAGAGCCCAGGCGCCGGTTCGCTTATAGCAG 4750v     4760v     4770v     4780v     4790v     4800v
-TASHKENT   GCTGTGGCTTAAAGCTGAAGGTGGGTTTCCGTCCGATTGGTTTGTATGCAGGTGTTGTGG
            GCTGTGGCTT AAG TG AGGT G TTTCCG CCGAT GGTTTGTATGCAGGTGTTGTGG
-BURMA      GCTGTGGCTTGAAGTTGAAGGTAGATTTCCGCCCGATCGGTTTGTATGCAGGTGTTGTGG
            GCTGTGG TTGAAGTTGAAGG  GA TTCCG CCGAT GG  TGTATGC GG GTTGT G
-MEXICO     GCTGTGGTTTGAAGTTGAAGGCTGACTTCCGGCCGATTGGGCTGTATGCCGGGGTTGTCG
```

```
                       4810v      4820v      4830v      4840v      4850v      4860v
-TASHKENT   TGACCCCCGGCCTTGGCGCGCTTCCCGACGTCGTGCGCTTGTCCGGCCGGCTTACTGAGA
            TG  CCCCCGGCCTTGGCGCGCTTCCCGA GT GTGCGCTTG CCGGCCGGCTTAC GAGA
-BURMA      TGGCCCCCGGCCTTGGCGCGCTCCCTGATGTTGTGCGCTTCGCCGGCCGGCTTACCGAGA
            T GCCCC GG CTGGGC   CT CC GATGT GT CG TTCGCCGG CGGCTT C GAGA
-MEXICO     TCGCCCCGGGGCTCGGGGCCCTACCCGATGTCGTTCGATTCGCCGGACGGCTTTCGGAGA 4870v      4880v      4890v      49C0v      4910v      4920v
-TASHKENT   AGAATTGGGGCCCTGGCCCTGAGCGGGCGGAGCAGCTCCGCCTTGCTGT
            AGAATTGGGGCCCTGGCCCTGAGCGGGCGGAGCAGCTCCGCCT GCTGT
-BURMA      AGAATTGGGGCCCTGGCCCTGAGCGGGCGGAGCAGCTCCGCCTCGCGTTAGTGATTTCC
            AGAA TGGGG CCTG  CC  AGCGGGC GAGCAGCTCCGCCTCGC GT      GATTTCC
-MEXICO     AGAACTGGGGGCCTGATCCGGAGCGGGCAGAGCAGCTCCGCCTCGCCGTGCAGGATTTCC 4930v      4940v      4950v      4960v      4970v      4980v
-BURMA      TCCGCAAGCTCACGAATGTAGCTCAGATGTGTGTGGATGTTGTTTCCCGTGTTTATGGGG
            TCCG A G T ACGAATGT GC CAGAT TGTGT GA GT GT TC  G GTTTA GGGG
-MEXICO     TCCGTAGGTTAACGAATGTGGCCCAGATTTGTGTTGAGGTGGTGTCTAGAGTTTACGGGG 4990v      5000v      5010v      5020v      5030v      5040v
-BURMA      TTTCCCCTGGACTCGTTCATAACCTGATTGGCATGCTACAGGCTGTTGCTGATGGCAAGG
            TTTCCCC GG CT GTTCATAACCTGAT GGCATGCT CAG CT TTG TGATGG AAGG
-MEXICO     TTTCCCCGGGTCTGGTTCATAACCTGATAGGCATGCTCCAGACTATTGGTGATGGTAAGG 5050v      5060v      5070v      5080v      5090v      5100v
-BURMA      CACATTTCACTGAGTCAGTAAAACCAGTGCTCGACTTGACAAATTCAATCTTGTGTCGGG
            C CATTT AC GAGTC GT AA CC  T CT GAC T ACA A  TCAAT  TG   CGG
-MEXICO     CGCATTTTACAGAGTCTGTTAAGCCTATACTTGACCTTACACACTCAATTATGCACCGGT 5110v      5120v      5130v      5140v      5150v
-BURMA      TGGAATGAATAACATGTCTTTTGCTGCGCCCATGGGTTCGCGACCATGCGCCCTCGGCCT
             GAATGAATAACATGT  TTTGCTGCGCCCATGGGTTCGC ACCATGCGCCCT GGCCT
-MEXICO     CTGAATGAATAACATGTGGTTTGCTGCGCCCATGGGTTCGCCACCATGCGCCCTAGGCCT 5170v      5180v      5190v      5200v      5210v      5220v
-BURMA      ATTTTGTTGCTGCTCCTCATGTTTTTGCCTATGCTGCCCGCGCCACCGCCCGGTCAGCCG
             TTTTG TG TG TCCTC TGTTT TGCCTATG TGCCCGCGCCACCG CCGGTCAGCCG
-MEXICO     CTTTTGCTGTTGTTCCTCTTGTTTCTGCCTATGTTGCCCGCGCCACCGACCGGTCAGCCG 5230v      5240v      5250v      5260v      5270v      5280v
-BURMA      TCTGGCCGCCGTCGTGGGCGGCGCAGCGGCGGTTCCGGCGGTGGTTTCTGGGGTGACCGG
            TCTGGCCGCCGTCGTGGGCGGCGCAGCGGCGGT CCGGCGGTGGTTTCTGGGGTGACCGG
-MEXICO     TCTGGCCGCCGTCGTGGGCGGCGCAGCGGCGGTACCGGCGGTGGTTTCTGGGGTGACCGG 5290v      5300v      5310v      5320v      5330v      5340v
-BURMA      GTTGATTCTCAGCCCTTCGCAATCCCCTATATTCATCCAACCAACCCCTTCGCCCCCGAT
            GTTGATTCTCAGCCCTTCGCAATCCCCTATATTCATCCAACCAACCCCTT  GCCCC GA
-MEXICO     GTTGATTCTCAGCCCTTCGCAATCCCCTATATTCATCCAACCAACCCCTTTGCCCCAGAC 5350v      5360v      5370v      5380v      5390v      5400v
-BURMA      GTCACCGCTGCGGCCGGGGCTGGACCTCGTGTTCGCCAACCCGCCCGACCACTCGGCTCC
            GT   CCGCTGCG CCGGG CTGGACCTCG  TTCGCCAACC GCCCG CCACT GGCTCC
-MEXICO     GTTGCCGCTGCGTCCGGGTCTGGACCTCGCCTTCGCCAACCAGCCCGGCCACTTGGCTCC 5410v      5420v      5430v      5440v      5450v      5460v
-BURMA      GCTTGGCGTGACCAGGCCCAGCGCCCCGCCGTTGCCTCACGTCGTAGACCTACCACAGCT
             CTTGGCG GA CAGGCCCAGCGCCCC  CCG TGCCTC CGTCG  GACCT CCACAGC
-MEXICO     ACTTGGCGAGATCAGGCCCAGCGCCCCTCCGCTGCCTCCCGTCGCCGACCTGCCACAGCC 5470v      5480v      5490v      5500v      5510v      5520v
-BURMA      GGGGCCGCGCCGCTAACCGCGGTCGCTCCGGCCCATGACACCCGCCAGTGCCTGATGTC
            GGGGC GCG CGCT AC GC GT GC CC GCCCATGACACC C CC GT CC GA GT
-MEXICO     GGGGCTGCGGCGCTGACGGCTGTGGCGCCTGCCCATGACACCTCACCCGTCCGGACGTT 5530v      5540v      5550v      5560v      5570v      5580v
-BURMA      GACTCCCGCGGCGCCATCTTGCGCCGGCAGTATAACCTATCAACATCTCCCCTTACCTCT
            GA TC CGCGG GC AT  T CGCCG CAGTATAA  T TC AC TC CCCCT AC TC
-MEXICO     GATTCTCGCGGTGCAATTCTACGCCGCAGTATAATTTGTCTACTTCACCCCTGACATCC 5590v      5600v      5610v      5620v      5630v      5640v
-BURMA      TCCGTGGCCACCGGCACTAACCTGGTTCTTTATGCCGCCCCTCTTAGTCCGCTTTTACCC
            TC GTGGCC C GGCACTAA  T GT CT TATGC GCCCC CTTA TCCGC T T CC
-MEXICO     TCTGTGGCCTCTGGCACTAATTTAGTCCTGTATGCAGCCCCCCTTAATCCGCCTCTGCCG 5650v      5660v      5670v      5680v      5690v      5700v
-BURMA      CTTCAGGACGGCACCAATACCCATATAATGGCCACGGAAGCTTCTAATTATGCCCAGTAC
            CT CAGGACGG AC AATAC CA AT ATGGCCAC GA GC TC AATTATGC CAGTAC
-MEXICO     CTGCAGGACGGTACTAATACTCACATTATGGCCACAGAGGCCTCCAATTATGCACAGTAC
```

-continued

```
              5710v      5720v      5730v      5740v      5750v      5760v
-BURMA    CGGGTTGCCCGTGCCACAATCCGTTACCGCCCGCTGGTCCCCAATGCTGTCGGCGGTTAC
          CGGGTTGCCCG GC AC ATCCGTTACCG CC CT GT CC AATGC GT GG GG TA
-MEXICO   CGGGTTGCCCGCGCTACTATCCGTTACCGGCCCCTAGTGCCTAATGCAGTTGGAGGCTAT 5770v      5780v      5790v      5800v      5810v      5820v
-BURMA    GCCATCTCCATCTCATTCTGGCCACAGACCACCACCACCCCGACGTCCGTTGATATGAAT
          GC AT TCCAT TC TTCTGCC CA AC ACCAC ACCCC AC TC GTTGA ATGAAT
-MEXICO   GCTATATCCATTTCTTTCTGGCCTCAAACAACCACAACCCCTACATCTGTTGACATGAAT 5830v      5840v      5850v      5860v      5870v      5880v
-BURMA    TCAATAACCTCGACGGATGTTCGTATTTTAGTCCAGCCCGGCATAGCCTCTGAGCTTGTG
          TC AT AC TC AC GATGT  G ATT   GT CA CC GGCATAGC TCTGA  T GT
-MEXICO   TCCATTACTTCCACTGATGTCAGGATTCTTGTTCAACCTGGCATAGCATCTGAATTGGTC 5890v      5900v      5910v      5920v      5930v      5940v
-BURMA    ATCCCAAGTGAGCGCCTACACTATCGTAACCAAGGCTGGCGCTCCGTCGAGACCTCTGGG
          ATCCCAAG GAGCGCCT CACTA CG AA CAAGG TGGCGCTC GT GAGAC TCTGG
-MEXICO   ATCCCAAGCGAGCGCCTTCACTACCGCAATCAAGGTTGGCGCTCGGTTGAGACATCTGGT 5950v      5960v      5970v      5980v      5990v      6000v
-BURMA    GTGGCTGAGGAGGAGGCTACCTCTGGTCTTGTTATGCTTTGCATACATGGCTCACTCGTA
          GT GCTGAGGAGGA GC ACCTC GGTCTTGT ATG T TGCATACATGGCTC C  GT
-MEXICO   GTTGCTGAGGAGGAAGCCACCTCCGGTCTTGTCATGTTATGCATACATGGCTCTCCAGTT 6010v      6020v      6020v      6040v      6050v      6060v
-BURMA    AATTCCTATACTAATACACCCTATACCGGTGCCCTCGGGCTGTTGGACTTTGCCCTTGAG
          AA TCCTATAC AATAC CC TATACCGGTGCCCT GG  T  TGGACTTTGCC T GAG
-MEXICO   AACTCCTATACCAATACCCCCTATACCGGTGCCCTTGGCTTACTGGACTTTGCCTTAGAG 6070v      6080v      6090v      6100v      6110v      6120v
-BURMA    CTTGAGTTTCGCAACCTTACCCCCGGTAACACCAATACGCGGGTCTCCCGTTATTCCAGC
          CTTGAGTTTCGCAA CT ACC CC GTAACACCAATAC CG GT TCCCGTTA TCCAGC
-MEXICO   CTTGAGTTTCGCAATCTCACCACCTGTAACACCAATACACGTGTGTCCCGTTACTCCAGC 6130v      6140v      6150v      6160v      6170v      6180v
-BURMA    ACTGCTCGCCACCGCCTTCGTCGCGGTGCGGACGGGACTGCCGAGCTCACCACCACGGCT
          ACTGCTCG CAC  C    CG  G  G     GACGGGACTGC GAGCT ACCAC AC GC
-MEXICO   ACTGCTCGTCACTCCGCCCGAGGGGCC---GACGGGACTGCGGAGCTGACCACAACTGCA 6190v      62C0v      6210v      6220v      6230v      6240v
-BURMA    GCTACCCGCTTTATGAAGGACCTCTATTTTACTAGTACTAATGGTGTCGGTGAGATCGGC
          GC ACC G TT ATGAA GA CTC A TTTAC  G    TAATGG GT GGTGA TCGGC
-MEXICO   GCCACCAGGTTCATGAAAGATCTCCACTTTACCGGCCTTAATGGGGTAGGTGAAGTCGGC 6250v      6260v      6270v      6280v      6290v      6300v
-BURMA    CGCGGGATAGCCCTCACCCTGTTCAACCTTGCTGACACTCTGCTTGGCGGCCTGCCGACA
          CGCGGGATAGC CT AC   T  T AACCTTGCTGACAC CT CT GGCGG CT CCGACA
-MEXICO   CGCGGGATAGCTCTAACATTACTTAACCTTGCTGACACGCTCCTCGGCGGGCTCCCGACA 6310v      6320v      6330v      6340v      6350v      6360v
-BURMA    GAATTGATTTCGTCGGCTGGTGGCCAGCTGTTCTACTCCCGTCCCGTTGTCTCAGCCAAT
          GAATT ATTTCGTCGGCTGG GG  CA CTGTT  TA TCCCG CC GTTGTCTCAGCCAAT
-MEXICO   GAATTAATTTCGTCGGCTGGCGGGCAACTGTTTTATTCCCGCCCGGTTGTCTCAGCCAAT 6370v      6380v      6390v      6400v      6410v      6420v
-BURMA    GGCGAGCCGACTGTTAAGTTGTATACATCTGTAGAGAATGCTCAGCAGGATAAGGGTATT
          GGCGAGCC AC GT AAG T TATACATC GT GAGAATGCTCAGCAGGATAAGGGT TT
-MEXICO   GGCGAGCCAACCGTGAAGCTCTATACATCGGAGGAGAATGCTCAGCAGGATAAGGGTGTT 6430v      6440v      6450v      6460v      6470v      6480v
-BURMA    GCAATCCCGCATGACATTGACCTCGGAGAATCTCGTGTGGTTATTCAGGATTATGATAAC
          GC ATCCC CA GA AT GA CT GG GA TC CGTGTGGT ATTCAGGATTATGA AAC
-MEXICO   GCTATCCCCCACGATATCGATCTTGGTGATTCGCGTGTGGTCATTCAGGATTATGACAAC 6490v      6500v      6510v      6520v      6530v      6540v
-BURMA    CAACATGAACAAGATCGGCCGACGCCTTCTCCAGCCCCATCGCGCCCTTTCTCTGTCCTT
          CA CATGA CA GATCGGCC AC CC TC CC GC CCATC CG CCTTT TCTGT CT
-MEXICO   CAGCATGAGCAGGATCGGCCCACCCCGTCGCCTGCGCCATCTCGGCCTTTTTCTGTTCTC 6550v      6560v      6570v      6580v      6590v      6600v
-BURMA    CGAGCTAATGATGTGCTTTGGCTCTCTCTCACCGCTGCCGAGTATGACCAGTCCACTTAT
          CGAGC AATGATGT CTTTGGCT TC CTCAC GC GCCGAGTATGACCAGTCCACTTA
-MEXICO   CGAGCAAATGATGTACTTTGGCTGTCCCTCACTGCAGCCGAGTATGACCAGTCCACTTAC 6610v      6620v      6630v      6640v      6650v      6660v
-BURMA    GGCTCTTCGACTGGCCCAGTTTATGTTTCTGACTCTGTGACCTTGGTTAATGTTGCGACC
          GG TC TC ACTGGCCC GTTTAT T TC GAC   GTGAC TTGGT AATGTTGCGAC
-MEXICO   GGGTCGTCAACTGGCCCGGTTTATATCTCGGACAGCGTGACTTTGGTGAATGTTGCGACT
```

```
                     -continued
              6670v     6680v    6690v    6700v    6710v    6720v
-BURMA        GGCGCGCAGGCCGTTGCCCGGTCGCTCGATTGGACCAAGGTCACACTTGACGGTCGCCCC GGCGCGCAGGCCGT GCCCG TCGCT GA TGG CCAA GTCAC CT GACGG CG CCC
-MEXICO       GGCGCGCAGGCCGTAGCCCGATCGCTTGACTGGTCCAAAGTCACCCTCGACGGGCGGCCC 6730v     6740v    6750v    6760v    6770v    6780v
-BURMA        CTCTCCACCATCCAGCAGTACTCGAAGACCTTCTTTGTCCTGCCGCTCCGCGGTAAGCTC CTC C AC   T   AGCA TA TC AAGAC TTCTTTGT CT CC CT CG GG AAGCTC
-MEXICO       CTCCCGACTGTTGAGCAATATTCCAAGACATTCTTTGTGCTCCCCCTTCGTGGCAAGCTC 6790v     6800v    6810v    6820v    6830v    6840v
-BURMA        TCTTTCTGGGAGGCAGGCACAACTAAAGCCGGGTACCCTTATAATTATAACACCACTGCT TC TT  TGGGAGGC GGCACAAC AAAGC GG TA CCTTATAATTATAA AC ACTGCT
-MEXICO       TCCTTTTGGGAGGCCGGCACAACAAAAGCAGGTTATCCTTATAATTATAATACTACTGCT 6850v     6860v    6870v    6880v    6890v    6900v
-BURMA        AGCGACCAACTGCTTGTCGAGAATGCCGCCGGGCACCGGGTCGCTATTTCCACTTACACC AG GACCA   T CT   T GA AATGC GCCGG CA CGGGTCGC ATTTC AC TA ACC
-MEXICO       AGTGACCAGATTCTGATTGAAAATGCTGCCGGCCATCGGGTCGCCATTTCAACCTATACC 6910v     6920v    6930v    6940v    6950v    6960v
-BURMA        ACTAGCCTGGGTGCTGGTCCCGTCTCCATTTCTGCGGTTGCCGTTTTAGCCCCCCACTCT AC AG CT GG GC GGTCC GTC CCATTTCTGCGG  GC GTTTT GC CC C CTC
-MEXICO       ACCAGGCTTGGGGCCGGTCCGGTCGCCATTTCTGCGGCCGCGGTTTTGGCTCCACGCTCC 6970v     6980v    6990v    7000v    7010v    7020v
-BURMA        GCGCTAGCATTGCTTGAGGATACCTTGGACTACCCTGCCCGCGCCCATACTTTTGATGAT GC CT GC   TGCT GAGGATAC TT GA TA CC G   CG GC CA AC TTTGATGA
-MEXICO       GCCCTGGCTCTGCTGGAGGATACTTTTGATTATCCGGGGCGGGCGCACACATTTGATGAC 7030v     7040v    7050v    7060v    7070v    7080v
-BURMA        TTCTGCCCAGAGTGCCGCCCCCTTGGCCTTCAGGGCTGCGCTTTCCAGTCTACTGTCGCT TTCTGCCC GA TGCCGC C  T GGCCT CAGGG TG GCTTTCCAGTC ACTGTCGCT
-MEXICO       TTCTGCCCTGAATGCCGCGCTTTAGGCCTCCAGGGTTGTGCTTTCCAGTCAACTGTCGCT 7090v     7100v    7110v    7120v    7130v    7140v
-BURMA        GAGCTTCAGCGCCTTAAGATGAAGGTGGGTAAAACTCGGGAGTTGTAGTTTATTTGCTTG GAGCT CAGCGCCTTAA   T AAGGTGGGTAAAACTCGGGAGTTGTAGTTTATTTG   TG
-MEXICO       GAGCTCCAGCGCCTTAAAGTTAAGGTGGGTAAAACTCGGGAGTTGTAGTTTATTTGGCTG 7150v     7160v             7170v    7180v    7190v
-BURMA        TGCCCCCCTTCTTTCTGTTGC---------TTATTTCTCATTTCTGCGTTCCGCGCTCCC TGCCC CCT CTT      TGC            TTATTTC   TTTCT  GT CCGCGCTCCC
-MEXICO       TGCCCACCTACTTATATCTGCTGATTTCCTTTATTTCCTTTTTCTCGGTCCCGCGCTCCC v 7195
-BURMA        TGA
              TGA
-MEXICO       TGA
```

A number of open reading frames, which are potential coding regions, have been found within the DNA sequences set forth above. As has already been noted, consensus residues for the RNA-directed RNA polymerase (RDRP) were identified in the HEV (Burma) strain clone ET1.1. Once a contiguous overlapping set of clones was accumulated, it became clear that the nonstructural elements containing the RDRP as well as what were identified as consensus residues for the helicase domain were located in the first large open reading frame (ORFI). ORFI covers the 5' half of the genome and begins at the first encoded met, after the 27th bp of the apparent non-coding sequence, and then extends 5079 bp before reaching a termination codon. Beginning 37 bp downstream from the ORF1 stop codon in the plus 1 frame is the second major opening reading frame (ORF2) extending 1980 bp and terminating 68 bp upstream from the point of poly A addition. The third forward ORF (in the plus 2 frame) is also utilized by HEV. ORF3 is only 370 bp in length and would not have been predicted to be utilized by the virus were it not for the identification of the immunoreactive cDNA clone 406.4-2 from the Mexico SISPA cDNA library (see below for detailed discussion). This epitope confirmed the utilization of ORF3 by the virus, although the means by which this ORF is expressed has not yet been fully elucidated. If we assume that the first met is utilized, ORF3 overlaps ORF1 by 1 bp at its 5' end and ORF2 by 328 bp at its 3' end. ORF2 contains the broadly reactive 406.3-2 epitope and also a signal sequence at its extreme 5' end. The first half of this ORF2 also has a high pI value (>10) similar to that seen with other virus capsid proteins. These data suggest that the ORF2 might be the predominant structural gene of HEV.

The existence of subgenomic transcripts prompted a set of experiments to determine whether these RNAs were produced by splicing from the 5' end of the genome. An analysis using subgenomic probes from throughout the genome, including the extreme 5' end, did not provide evidence for a spliced transcript. However, it was discovered that a region of the genome displayed a high degree of homology with a 21 bp segment identified in Sindbis as a probably internal initiation site for RNA transcription used in the production of its subgenomic messages. Sixteen of 21 (76%) of the nucleotides are identical.

Two cDNA clones which encode an epitope of HEV that is recognized by sera collected from different ET-NANB outbreaks (i.e., a universally recognized epitope) have been isolated and characterized. One of the clones immunoreacted with 8 human sera from different infected individuals and the other clone immunoreacted with 7 of the human sera tested. Both clones immunoreacted specifically with cyno sera from infected animals and exhibited no immunologic response to sera from uninfected animals. The sequences of the cDNAs in these recombinant phages, designated 406.3-2 and 406.4-2 have been determined. The HEV open reading frames are shown to encode epitopes specifically recognized by sera from patients with HEV infections. The cDNA sequences and the polypeptides that they encode are set forth below.

Epitopes Derived From Mexican Strain of HEV 406.4-2 sequence (nucleotide sequence has SEQ ID NO.13; amino acid sequence has SEQ ID NO.14):

The universal nature of these epitopes is evident from the homology exhibited by the DNA that encodes them. If the epitope coding sequences from the Mexican strains shown above are compared to DNA sequences from other strains, such as the Burmese Strain also set forth above, similarities are evident, as shown in the following comparisons.

```
C GCC AAC CAG CCC GGC CAC TTG GCT CCA CTT GGC GAG ATC AGG CCC       46 SEQ ID NO. 13:
  Ala Asn Gln Pro Gly His Leu Ala Pro Leu Gly Glu Ile Arg Pro
    1               5                  10                 15

AGC GCC CCT CCG CTG CCT CCC GTC GCC GAC CTG CCA CAG CCG GGG CTG     94
Ser Ala Pro Pro Leu Pro Pro Val Ala Asp Leu Pro Gln Pro Gly Leu
                 20                  25                  30

CGG CGC TGA CGGCTGTGGC GCCTGCCCAT GACACCTCAC CCGTCCCGGA           143
Arg Arg  .

CGTTGATTCT CGCGGTGCAA TTCTACGCCG CCAGTATAAT TTGTCTACTT CACCCCTGAC  203

ATCCTCTGTG GCCTCTGGCA CTAATTTAGT CCTGTATGCA GCCCCCCTTA ATCCGCCTCT  253

GCCGCTGCAG GACGGTACTA ATACTCACAT TATGGCCACA GAGGCCTCCA ATTATGCACA  323

GTACCGGGTT GCCCGCGCTA CTATCCGTTA CCGGCCCCTA GTGCCTAATG CAGTTGGAGG  383

CTATGCTATA TCCATTTCTT TCTGGCCTCA AACAACCACA ACCCCTACAT CTGTTGACAT  443

GAATTC                                                             449

Ala Asn Gln Pro Gly His Leu Ala Pro Leu Gly Glu Ile Arg Pro Ser        SEQ ID NO. 14:
  1               5                  10                  15

Ala Pro Pro Leu Pro Pro Val Ala Asp Leu Pro Gln Pro Gly Leu Arg
             20                  25                  30
Arg  .
```

406.3-2 sequence (nucleotide sequence has SEQ ID NO.15; amino acid sequence has SEQ ID NO.16):

```
GGAT ACT TTT GAT TAT CCG GGG CGG GCG CAC ACA TTT GAT GAC TTC TGC    49 SEQ ID NO. 15:
     Thr Phe Asp Tyr Pro Gly Arg Ala His Thr Phe Asp Asp Phe Cys
       1               5                  10                  15

CCT GAA TGC CGC GCT TTA GGC CTC CAG GGT TGT GCT TTC CAG TCA ACT     97
Pro Glu Cys Arg Ala Leu Gly Leu Gln Gly Cys Ala Phe Gln Ser Thr
                 20                  25                  30

GTC GCT GAG CTC CAG CGC CTT AAA GTT AAG GTT                       130
Val Ala Glu Leu Gln Arg Leu Lys Val Lys Val
             35                  40

Thr Phe Asp Tyr Pro Gly Arg Ala His Thr Phe Asp Asp Phe Cys Pro        SEQ ID NO. 16:
  1               5                  10                  15

Glu Cys Arg Ala Leu Gly Leu Gln Gly Cys Ala Phe Gln Ser Thr Val
             20                  25                  30

Ala Glu Leu Gln Arg Leu Lys Val Lys Val
         35                  40
```

Comparison of 406.4-2 Epitopes, HEV Mexico and Burma Strains

```
                                10        20        30
MEXICAN (SEQ ID NO. 17)  ANQPGHLAPLGEIRPSAPPLPPVADLPQPGLRR

::..:.: :::: .::::::::.:.:::: : ::

BURMA (SEQ ID NO. 18)    ANPPDHSAPLGVTRPSAPPLPHVVDLPQLGPRR
                                10        20        30
```

There is 73.5% identity in a 33-amino acid overlap

Comparison of 406.3-2 Epitopes, HEV Mexico and Burma Strains

```
                                 10        20        30        40
MEXICAN (SEQ ID No. 19)  TFDYPGRAHTFDDFCPECRALGLQGCAFQSTVAELQRLKVKV

:.:::.:::::::::::::.::::::::::::::::::.::

BURMA (SEQ ID No. 20)    TLDYPARAHTFDDFCPECRPLGLQGCAFQSTVAELQRLKMKV
                                 10        20        30        40
```

There is 90.5% identity in the 42-amino acid overlap

It will be recognized by one skilled in the art of molecular genetics that each of the specific DNA sequences given above shows a corresponding complementary DNA sequence as well as RNA sequences corresponding to both the principal sequence shown and the complementary DNA sequence. Additionally, open reading frames encoding peptides are present, and expressible peptides are disclosed by the nucleotide sequences without setting forth the amino acid sequences explicitly, in the same manner as if the amino acid sequences were explicitly set forth as in the ET1.1 sequence or other sequences above.

DETAILED DESCRIPTION OF THE INVENTION

I. Definitions

The terms defined below have the following meaning herein:

1. "Enterically transmitted non-A/non-B hepatitis viral agent, ET-NANB, or HEV" means a virus, virus type, or virus class which (1) causes water-borne, infectious hepatitis, (ii) is transmissible in cynomolgus monkeys, (iii) is serologically distinct from hepatitis A virus (HAV), hepatitis B virus (HBV), hepatitis C virus (HCV), and hepatitis D virus, and (iv) includes a genomic region which is homologous to the 1.33 kb cDNA insert in plasmid pTZKF1 (ET1.1) carried in E. coli strain BB4 identified by ATCC deposit number 67717.

2. Two nucleic acid fragments are "homologous" if they are capable of hybridizing to one another under hybridization conditions described in Maniatis et al., op. cit., pp. 320–323. However, using the following wash conditions: 2×SCC, 0.1% SDS, room temperature twice, 30 minutes each; then 2×SCC, 0.1% SDS, 50° C. once, 30 minutes; then 2×SCC, room temperature twice, 10 minutes each, homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

3. Two amino acid sequences or two nucleotide sequences (in an alternative definition for homology between two nucleotide sequences) are considered homologous (as this term is preferably used in this specification) if they have an alignment score of >5 (in standard deviation units) using the program ALIGN with the mutation gap matrix and a gap penalty of 6 or greater. See Dayhoff, M. O., in Atlas of Protein Sequence and Structure (1972) Vol. 5, National Biomedical Research Foundation, pp. 101–110, and Supplement 2 to this volume, pp. 1–10. The two sequences (or parts thereof, preferably at least 30 amino acids in length) are more preferably homologous if their amino acids are greater than or equal to 50% identical when optimally aligned using the ALIGN program mentioned above.

4. A DNA fragment is "derived from" an ET-NANB viral agent if it has the same or substantially the same basepair sequence as a region of the viral agent genome.

5. A protein is "derived from" an ET-NANB viral agent if it is encoded by an open reading frame of a DNA or RNA fragment derived from an ET-NANB viral agent.

II. Obtaining Cloned ET-NANB Fragments

According to one aspect of the invention, it has been found that a virus-specific DNA clone can be produced by (a) isolating RNA from the bile of a cynomolgus monkey having a known ET-NANB infection, (b) cloning the cDNA fragments to form a fragment library, and (c) screening the library by differential hybridization to radiolabeled cDNAs from infected and non-infected bile sources.

A. cDNA Fragment Mixture

ET-NANB infection in cynomolgus monkeys is initiated by inoculating the animals intravenously with a 10% w/v suspension from human case stools positive for 27–34 nm ET-NANB particles (mean diameter 32 nm). An infected animal is monitored for elevated levels of alanine aminotransferase, indicating hepatitis infection. ET-NANB infection is confirmed by immunospecific binding of seropositive antibodies to virus-like particles (VLPs), according to published methods (Gravelle). Briefly, a stool (or bile) specimen taken from the infected animal 3–4 weeks after infection is diluted 1:10 with phosphate-buffered saline, and the lot suspension is clarified by low-speed centrifugation and filtration successively through 1.2 and 0.45 micron filters. The material may be further purified by pelleting through a 30% sucrose cushion (Bradley). The resulting preparation of VLPs is mixed with diluted serum from human patients with known ET-NANB infection. After incubation overnight, the mixture is centrifuged overnight to pellet immune aggregates, and these are stained and examined by electron microscopy for antibody binding to the VLPs.

ET-NANB infection can also be confirmed by seroconversion to VLP-positive serum. Here the serum of the infected animal is mixed as above with 27–34 nm VLPs isolated from the stool specimens of infected human cases and examined by immune electron microscopy for antibody binding to the VLPs.

Bile can be collected from ET-NANB positive animals by either cannulating the bile duct and collecting the bile fluid or by draining the bile duct during necropsy. Total RNA is extracted from the bile by hot phenol extraction, as outlined in Example 1A. The RNA fragments are used to synthesize corresponding duplex cDNA fragments by random priming, also as referenced in Example 1A. The cDNA fragments may be fractionated by gel electrophoresis density gradient centrifugation to obtain a desired size class of fragments, e.g., 500–4,000 basepair fragments.

Although alternative sources of viral material, such as VLPs obtained from stool samples (as described in Example 4), may be used for producing a CDNA fraction, the bile source is preferred. According to one aspect of the invention, it has been found that bile from ET-NANB-infected monkeys shows a greater number of intact viral particles than material obtained from stool samples, as evidenced by immune electron microscopy. Bile obtained from an ET-NANB infected human or cynomolgus macaque, for use as a source of ET-NANB viral protein or genomic material, or intact virus, forms part of the present invention.

B. CDNA Library and Screening

The CDNA fragments from above are cloned into a suitable cloning vector to form a cDNA library. This may be done by equipping blunt-ended fragments with a suitable end linker, such as an EcoRI sequence, and inserting the fragments into a suitable insertion site of a cloning vector, such as at a unique EcoRI site. After initial cloning, the library may be re-cloned, if desired, to increase the percentage of vectors containing a fragment insert. The library construction described in Example 1B is illustrative. Here cDNA fragments were blunt-ended, equipped with EcoRI ends, and inserted into the EcoRI site of the lambda phage vector gt10. The library phage, which showed less than 5% fragment inserts, was isolated, and the fragment inserts re-cloned into the lambda gt10 vector, yielding more than 95% insert-containing phage.

The cDNA library is screened for sequences specific for ET-NANB by differential hybridization to cDNA probes derived from infected and non-infected sources. cDNA fragments from infected and non-infected source bile or stool viral isolates can be prepared as above. Radiolabeling the fragments is by random labeling nick translation, or ending, according to conventional methods (Maniatis, p. 109). The cDNA library from above is screened by transfer to duplicate nitrocellulose filters, and hybridization with both infected-source and non-infected-source (control) radiolabeled probes, as detailed in Example 2. In order to recover sequences that hybridize at the preferred outer limit of 25–30% basepair mismatches, clones can be selected if they hybridize under the conditions described in Maniatis et al., op. cit., pp. 320–323, but using the following wash conditions: 2×SCC, 0.1% SDS, room temperature—twice, 30 minutes each; then 2×SCC, 0.1% SDS, 50° C.—once, 30 minutes; then 2×SCC, room temperature—twice, 10 minutes each. These conditions allowed identification of the Mexican isolate discussed above using the ET1.1 sequence as a probe. Plaques which show selective hybridization to the infected-source probes are preferably re-plated at low plating density and re-screened as above, to isolate single clones which are specific for ET-NANB sequences. As indicated in Example 2, sixteen clones which hybridized specifically with infected-source probes were identified by these procedures. One of the clones, designated lambda gt101.1, contained a 1.33 kilobase fragment insert.

C. ET-NANB Sequences

The basepair sequence of cloned regions of the ET-NANB fragments from Part B are determined by standard sequencing methods. In one illustrative method, described in Example 3, the fragment insert from the selected cloning vector is excised, isolated by gel electrophoresis, and inserted into a cloning vector whose basepair sequence on either side of the insertion site is known. The particular vector employed in Example 3 is a pTZKF1 vector shown at the left in FIG. 1. The ET-NANB fragment from the gt10-1.1 phage was inserted at the unique EcoRI site of the pTZKF1 plasmid. Recombinants carrying the desired insert were identified by hybridization with the isolated 1.33 kilobase fragment, as described in Example 3. One selected plasmid, identified as pTZKF1 (ET1.1), gave the expected 1.33 kb fragment after vector digestion with EcoRI. *E. coli* strain BB4 infected with the pTZKF1 (ET1.1) plasmid has been deposited with the American Type Culture Collection, Rockville, Md., and is identified by ATCC deposit number 67717.

The pTZKF1(ET1.1) plasmid is illustrated at the bottom in FIG. 1. The fragment insert has 5' and 3' end regions denoted at A and C, respectively, and an intermediate region, denoted at B. The sequences in these regions were determined by standard dideoxy sequencing and were set forth in an earlier application in this series. The three short sequences (A, B, and C) are from the same insert strand. As will be seen in Example 3, the B-region sequence was actually determined from the opposite strand, so that the B region sequence shown above represents the complement of the sequence in the sequenced strand. The base numbers of the partial sequences are approximate.

Later work in the laboratory of the inventors identified the full sequence, set forth above. Fragments of this total sequence can readily be prepared using restriction endonucleases. Computer analysis of both the forward and reverse sequence has identified a number of cleavage sites.

III. ET-NANB Fragments

According to another aspect, the invention includes ET-NANB-specific fragments or probes which hybridize with ET-NANB genomic sequences or cDNA fragments derived therefrom. The fragments may include full-length cDNA fragments such as described in Section II, or may be derived from shorter sequence regions within cloned CDNA fragments. Shorter fragments can be prepared by enzymatic digestion of full-length fragments under conditions which yield desired-sized fragments, as will be described in Section IV. Alternatively, the fragments can be produced by oligonucleotide synthetic methods, using sequences derived from the cDNA fragments. Methods or commercial services for Producing selected-sequence oligonucleotide fragments are available. Fragments are usually at least 12 nucleotides in length, preferably at least 14, 20, 30 or 50 nucleotides, when used as probes. Probes can be full length or less than 500, preferably less than 300 or 200, nucleotides in length.

To confirm that a given ET-NANB fragment is in fact derived from the ET-NANB viral agent, the fragment can be shown to hybridize selectively with cDNA from infected sources. By way of illustration, to confirm that the 1.33 kb fragment in the pTZKF1(ET1.1) plasmid is ET-NANB in origin, the fragment was excised from the pTZKF1(ET1.1) plasmid, purified, and radiolabeled by random labeling. The radiolabeled fragment was hybridized with fractionated cDNAs from infected and non-infected sources to confirm that the probe reacts only with infected-source cDNAs. This method is illustrated in Example 4, where the above radiolabeled 1.33 kb fragment from pTZKF1(ET1.1) plasmid was examined for binding to cDNAs prepared from infected and non-infected sources. The infected sources are (1) bile from a cynomolgus macaque infected with a strain of virus derived from stool samples from human patients from Burma with known ET-NANB infections and (2) a viral agent derived from the stool sample of a human ET-NANB patient from Mexico. The cDNAs in each fragment mixture were first amplified by a linker/primer amplification method described in Example 4. Fragment separation was on agarose gel, followed by Southern blotting and then hybridization to bind the radiolabeled 1.33 kb fragment to the fractionated cDNAs. The lane containing cDNAs from the infected sources showed a smeared band of bound probe, as expected (cDNAs amplified by the linker/primer amplification method would be expected to have a broad range of sizes). No probe binding to the amplified cDNAs from the non-infected sources was observed. The results indicate that the 1.33 kb probe is specific for CDNA fragments associated with ET-NANB infection. This same type of study, using ET 1.1 as the probe, has demonstrated hybridization to ET-NANB samples collected from Tashkent, Somalia, Borneo and Pakistan. Secondly, the fact that the probe is specific for ET-NANB related sequences derived from different continents (Asia, Africa and North America) indicates the cloned ET-NANB Burma sequence (ET1.1) is derived from a common ET-NANB virus or virus class responsible for ET-NANB hepatitis infection worldwide.

In a related confirmatory study, probe binding to fractionated genomic fragments prepared from human or cynomolgus macaque genomic DNA (both infected and uninfected) was examined. No probe binding was observed to either genomic fraction, demonstrating that the ET-NANB fragment is not an endogenous human or cynomolgus genomic fragment and additionally demonstrating that HEV is an RNA virus.

Another confirmation of ET-NANB specific sequences in the fragments is the ability to express ET-NANB proteins from coding regions in the fragments and to demonstrated specific sero-reactivity of these proteins with sera collected during documented outbreaks of ET-NANB. Section IV below discusses methods of protein expression using the fragments.

One important use of the ET-NANB-specific fragments is for identifying ET-NANB-derived cDNAs which contain additional sequence information. The newly identified cDNAs, in turn, yield new fragment probes, allowing further iterations until the entire viral genome is identified and sequenced. Procedures for identifying additional ET-NANB library clones and generating new probes therefrom generally follow the cloning and selection procedures described in Section II.

The fragments (and oligonucleotides prepared based on the sequences given above) are also useful as primers for a polymerase chain reaction method of detecting ET-NANB viral genomic material in a patient sample. This diagnostic method will be described in Section V below.

Two specific genetic sequences derived from the Mexican strain, identified herein as 406.3-2 and 406.4-2, have been identified that encode immunogenic epitopes. This was done by isolating clones which encode epitopes that immunologically react specifically with sera from individuals and experimental animals infected with HEV. Comparison of the isolated sequences with those in the Genebank collection of genetic sequences indicate that these viral sequences are novel. Since these sequences are unique, they can be used to identify the presence of HEV and to distinguish this strain of hepatitis from HAV, HBV, and HCV strains. The sequences are also useful for the design of oligonucleotide probes to diagnose the presence of virus in samples. They can be used for the synthesis of polypeptides that themselves are used in immunoassays. The specific 406.3-2 and 406.4-2 sequences can be incorporated into other genetic material, such as vectors, for ease of expression or replication. They can also be used (as demonstrated above) for identifying similar antigenic regions encoded by related viral strains, such as the Burmese strain.

IV. ET-NANB Proteins

As indicated above, ET-NANB proteins can be prepared by expressing open reading-frame coding regions in ET-NANB fragments. In one preferred approach, the ET-NANB fragments used for protein expression are derived from cloned cDNAs which have been treated to produce desired-size fragments, and preferably random fragments with sizes predominantly between about 100 to about 300 base pairs. Example 5 describes the preparation of such fragments by DNAs digestion. Because it is desired to obtain peptide antigens of between about 30 to about 100 amino acids, the digest fragments are preferably size fractionated, for example by gel electrophoresis, to select those in the approximately 100–300 basepair size range. Alternatively, cDNA libraries constructed directly from HEV-containing sources (e.g., bile or stool) can be screened directly if cloned into an appropriate expression vector (see below).

For example, the ET-NANB proteins expressed by the 406.3-2 and 406.4-2 sequences (and peptide fragments thereof) are particularly preferred since these proteins have been demonstrated to be immunoreactive with a variety of different human sera, thereby indicating the presence of one or more epitopes specific for HEV on their surfaces. These clones were identified by direct screening of a gt11 library.

A. Expression Vector

The ET-NANB fragments are inserted into a suitable expression vector. One exemplary expression vector is lambda gt11, which contains a unique EcoRI insertion site 53 base pairs upstream of the translation termination codon of the beta-galactosidase gene. Thus, the inserted sequence will be expressed as a beta-galactosidase fusion protein which contains the N-terminal portion of the beta-galactosidase gene, the heterologous peptide, and optionally the C-terminal region of the beta-galactosidase peptide (the C-terminal portion being expressed when the heterologous peptide coding sequence does not contain a translation termination codon). This vector also produces a temperature-sensitive repressor (c1857) which causes viral lysogeny at permissive temperatures, e.g., 32° C., and leads to viral lysis at elevated temperatures, e.g., 37° C. Advantages of this vector include: (1) highly efficient recombinant generation, (2) ability to select lysogenized host cells on the basis of host-cell growth at permissive, but not non-permissive, temperatures, and (3) high levels of recombinant fusion protein production. Further, since phage containing a heterologous insert produces an inactive beta-galactosidase enzyme, phage with inserts can be readily identified by a beta-galactosidase colored-substrate reaction.

For insertion into the expression vector, the viral digest fragments may be modified, if needed, to contain selected restriction-site linkers, such as EcoRI linkers, according to conventional procedures. Example 1 illustrates methods for cloning the digest fragments into lambda gt11, which includes the steps of blunt-ending the fragments, ligating with EcoRI linkers, and introducing the fragments into EcoRI-cut lambda gt11. The resulting viral genomic library may be checked to confirm that a relatively large (representative) library has been produced. This can be done, in the case of the lambda gt11 vector, by infecting a suitable bacterial host, plating the bacteria, and examining the plaques for loss of beta-galactosidase activity. Using the procedures described in Example 1, about 50% of the plaques showed loss of enzyme activity.

B. Peptide Antigen Expression

The viral genomic library armed above is screened for production of peptide antigen (expressed as a fusion protein) which is immunoreactive with antiserum from ET-NANB seropositve individuals. In a preferred screening method, host cells infected with phage library vectors are plated, as above, and the plate is blotted with a nitrocellulose filter to transfer recombinant protein antigens produced by the cells onto the filter. The filter is then reacted with the ET-NANB antiserum, washed to remove unbound antibody, and reacted with reporter-labeled, anti-human antibody, which becomes bound to the filter, in sandwich fashion, through the anti-ET-NANB antibody.

Typically phage plaques which are identified by virtue of their production of recombinant antigen of interest are re-examined at a relatively low density for production of antibody-reactive fusion protein. Several recombinant phage clones which produced immunoreactive recombinant antigen were identified in the procedure.

The selected expression vectors may be used for scale-up production, for purposes of recombinant protein purification. Scale-up production is carried out using one of a variety of reported methods for (a) lysogenizing a suitable host, such as *E. coli*, with a selected lambda gt11 recombinant (b) culturing the transduced cells under conditions that yield high levels of the heterologous peptide, and (c) purifying the recombinant antigen from the lysed cells.

In one preferred method involving the above lambda gt11 cloning vector, a high-producer *E. coli* host, BNN103, is infected with the selected library phage and replica plated on two plates. One of the plates is grown at 32° C., at which viral lysogeny can occur, and the other at 42° C., at which the infecting phage is in a lytic stage and therefore prevents cell growth. Cells which grow at the lower but not the higher temperature are therefore assumed to be successfully lysogenized.

The lysogenized host cells are then grown under liquid culture conditions which favor high production of the fused protein containing the viral insert, and lysed by rapid freezing to release the desired fusion protein.

C. Peptide Purification

The recombinant peptide can be purified by standard protein purification procedures which may include differential precipitation, molecular sieve chromatography, ion-exchange chromatography, isoelectric focusing, gel electrophoresis and affinity chromatography. In the case of a fused protein, such as the beta-galactosidase fused protein prepared as above, the protein isolation techniques which are used can be adapted from those used in isolation of the native protein. Thus, for isolation of a soluble betagalactosidase fusion protein, the protein can be isolated readily by simple affinity chromatography, by passing the cell lysis material over a solid support having surface-bound anti-beta-galactosidase antibody.

D. Viral Proteins

The ET-NANB protein of the invention may also be derived directly from the ET-NANB viral agent. VLPs or protein isolated from stool or liver samples from an infected individual, as above, are one suitable source of viral protein material. The VLPs isolated from the stool sample may be further purified by affinity chromatography prior to protein isolation (see below). The viral agent may also be raised in cell culture, which provides a convenient and potentially concentrated source of viral protein. Co-owned U.S. patent application Ser. No. 846,757, filed Apr. 1, 1986, describes an immortalized trioma liver cell which supports NANB infection in cell culture. The trioma cell line is prepared by fusing human liver cells with a mouse/human fusion partner selected for human chromosome stability. Cells containing the desired NANB viral agent can be identified by immunofluorescence methods, employing anti-ET-NANB human antibodies.

The viral agent is disrupted, prior to protein isolation, by conventional methods, which can include sonication, high- or low-salt conditions, or use of detergents.

Purification of ET-NANB viral protein can be carried out by affinity chromatography, using a purified anti-ET-NANB antibody attached according to standard methods to a suitable solid support. The antibody itself may be purified by affinity chromatography, where an immunoreactive recombinant ETNANB protein, such as described above, is attached to a solid support, for isolation of anti-ET-NANB antibodies from an immune serum source. The bound antibody is released from the support by standard methods.

Alternatively, the anti-ET-NANB antibody may be an antiserum or a monoclonal antibody (Mab) prepared by immunizing a mouse or other animal with recombinant ETNANB protein. For Mab production, lymphocytes are isolated from the animal and immortalized with a suitable fusion partner, and successful fusion products which react with the recombinant protein immunogen are selected. These in turn may be used in affinity purification procedures, described above, to obtain native ET-NANB antigen.

V. Utility

Although ET-NANB is primarily of interest because of its effects on humans, recent data has shown that this virus is also capable of infecting other animals, especially mammals. Accordingly, any discussion herein of utility applies to both human and veterinary uses, especially commercial veterinary uses, such as the diagnosis and treatment of pigs, cattle, sheep, horses, and other domesticated animals.

A. Diagnostic Methods

The particles and antigens of the invention, as well as the genetic material, can be used in diagnostic assays. Methods for detecting the presence of ET-NANB hepatitis comprise analyzing a biological sample such as a blood sample, stool sample or liver biopsy specimen for the presence of an analyte associated with ET-NANB hepatitis virus.

The analyte can be a nucleotide sequence which hybridizes with a probe comprising a sequence of at least about 16 consecutive nucleotides, usually 30 to 200 nucleotides, up to substantially the full sequence of the sequences shown above (cDNA sequences). The analyte can be RNA or cDNA. The analyte is typically a virus particle suspected of being ET-NANB or a particle for which this classification is being ruled out. The virus particle can be further characterized as having an RNA viral genome comprising a sequence at least about 70% homologous to a sequence of at least 12 consecutive nucleotides of the "forward" and "reverse"

sequences given above, usually at least about 80% homologous to at least about 60 consecutive nucleotides within the sequences, and may comprise a sequence substantially homologous to the full-length sequences. In order to detect an analyte, where the analyte hybridizes to a probe, the probe may contain a detectable label. Particularly preferred for use as a probe are sequences of consecutive nucleotides derived from the 406.3-2 and 406.4-2 clones described herein, since these clones appear to be particularly diagnostic for HEV.

The analyte can also comprise an antibody which recognizes an antigen, such as a cell surface antigen, in a ET-NANB virus particle. The analyte can also be a ET-NANB viral antigen. Where the analyte is an antibody or an antigen, either a labelled antigen or antibody, respectively, can be used to bind to the analyte to form an immunological complex, which can then be detected by means of the label.

Typically, methods for detecting analytes such as surface antigens and/or whole particles are based on immunoassays. Immunoassays can be conducted either to determine the presence of antibodies in the host that have arisen from infection by ET-NANB hepatitis virus or by assays that directly determine the presence of virus particles or antigens. Such techniques are well known and need not be described here in detail. Examples include both heterogeneous and homogeneous immunoassay techniques. Both techniques are based on the formation of an immunological complex between the virus particle or its antigen and a corresponding specific antibody. Heterogeneous assays for viral antigens typically use a specific monoclonal or polyclonal antibody bound to a solid surface. Sandwich assays are becoming increasingly popular. Homogeneous assays, which are carried out in solution without the presence of a solid phase, can also be used, for example by determining the difference in enzyme activity brought on by binding of free antibody to an enzyme-antigen conjugate. A number of suitable assays are disclosed in U.S. Pat. Nos. 3,817,837, 4,006,360, 3,996,345.

When assaying for the presence of antibodies induced by ET-NANB viruses, the viruses and antigens of the invention can be used as specific binding agents to detect either IgG or IgM antibodies. Since IgM antibodies are typically the first antibodies that appear during the course of an infection, when IgG synthesis may not yet have been initiated, specifically distinguishing between IgM and IgG antibodies present in the blood stream of a host will enable a physician or other investigator to determine whether the infection is recent or convalescent. Proteins expressed by the 406.3-2 and 406.4-2 clones described herein and peptide fragments thereof are particularly preferred for use as specific binding agents to detect antibodies since they have been demonstrated to be reactive with a number of different human HEV sera. Further, they are reactive with both acute and convalescent sera.

In one diagnostic configuration, test serum is reacted with a solid phase reagent having surface-bound ET-NANB protein antigen. After binding anti-ET-NANB antibody to the reagent and removing unbound serum components by washing, the reagent is reacted with reporter-labeled anti-human antibody to bind reporter to the reagent in proportion to the amount of bound anti-ET-NANB antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric or colorimetric substrate.

The solid surface reagent in the above assay prepared by known techniques for attaching protein material to solid support material, such as polymeric beads, dip sticks, or filter material. These attachment methods generally include non-specific adsorption of the protein to the support or covalent attachment of the protein, typically through a free amine group, to a chemically reactive group on the solid support, such as an activate carboxyl, hydroxyl, or aldehyde group.

In a second diagnostic configuration, known as a homogeneous assay, antibody binding to a solid support produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labeled anti-human antibody to the antibody being examined, either IgM (acute phase) or IgG (convalescent phase), and measuring the amount of reporter bound to the solid support, as in the first method, or may involve observing the effect of antibody binding on a homogeneous assay reagent, as in the second method.

Also forming part of the invention is an assay system or kit for carrying out the assay method just described. The kit generally includes a support with surface-bound recombinant protein antigen which is (a) immunoreactive with antibodies present in individuals infected with enterically transmitted nonA/nonB viral agent and (b) derived from a viral hepatitis agent whose genome contains a region which is homologous to the 1.33 kb DNA EcoRI insert present in plasmid pTZKF1(ET1.1) carried in *E. Coli* strain BB4, and having ATCC deposit no. 67717. A reporter-labeled anti-human antibody in the kit is used for detecting surface-bound anti-ET-NANB antibody.

B. Viral Genome Diagnostic Applications

The genetic material of the invention can itself be used in numerous assays as probes for genetic material present in naturally occurring infections. One method for amplification of target nucleic acids, for later analysis by hybridization assays, is known as the polymerase chain reaction or PCR technique. The PCR technique can be applied to detecting virus particles of the invention in suspected pathological samples using oligonucleotide primers spaced apart from each other and based on the genetic sequence set forth above. The primers are complementary to opposite strands of a double stranded DNA molecule and are typically separated by from about 50 to 450 nt or more (usually not more than 2000 nt). This method entails preparing the specific oligonucleotide primers and then repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula $2^n$ where n is the number of cycles. Given that the average efficiency per cycle ranges from about 65% to 85%, 25 cycles produce from 0.3 to 4.8 million copies of the target sequence. The PCR method is described in a number of publications, including Saiki et al., Science (1985) 230:1350–1354; Saiki et al., Nature (1986) 324:163–166; and Scharf et al., Science (1986) 233:1076–1078. Also see U.S. Pat. Nos. 4,683,194; 4,683,195; and 4,683,202.

The invention includes a specific diagnostic method for determination of ET-NANB viral agent, based on selective amplification of ET-NANB fragments. This method employs a pair of single-strand primers derived from non-homologous regions of opposite a strands of a DNA duplex fragment, which in turn is derived from an enterically transmitted viral hepatitis agent whose genome contains a region which is homologous to the 1.33 kb DNA EcoRI insert present in plasmid pTZKF1(ET1.1) carried in E. coli strain BB4, and having ATCC deposit no. 67717. These "primer fragments," which form one aspect of the invention, are prepared from ET-NANB fragments such as described in Section III above. The method follows the process for amplifying selected nucleic acid sequences as disclosed in U.S. Pat. No. 4,683,202, as discussed above.

C. Peptide Vaccine

Any of the antigens of the invention can be used in preparation of a vaccine. A preferred starting material for preparation of a vaccine is the particle antigen isolated from bile. The antigens are preferably initially recovered as intact particles as described above. However, it is also possible to prepare a suitable vaccine from particles isolated from other sources or non-particle recombinant antigens. When non-particle antigens are used (typically soluble antigens), proteins derived from the viral envelope or viral capsid are preferred for use in preparing vaccines. These proteins can be purified by affinity chromatography, also described above.

If the purified protein is not immunogenic per se, it can be bound to a carrier to make the protein immunogenic. Carriers include bovine serum albumin, keyhole limpet hemocyanin and the like. It is desirable, but not necessary, to purify antigens to be substantially free of human protein. However, it is more important that the antigens be free of proteins, viruses, and other substances not of human origin that may have been introduced by way of, or contamination of, the nutrient medium, cell lines, tissues, or pathological fluids from which the virus is cultured or obtained.

Vaccination can be conducted in conventional fashion. For example, the antigen, whether a viral particle or a protein, can be used in a suitable diluent such as water, saline, buffered salines, complete or incomplete adjuvants, and the like. The immunogen is administered using standard techniques for antibody induction, such as by subcutaneous administration of physiologically compatible, sterile solutions containing inactivated or attenuated virus particles or antigens. An immune response producing amount of virus particles is typically administered per vaccinizing injection, typically in a volume of one milliliter or less.

A specific example of a vaccine composition includes, in a pharmacologically acceptable adjuvant, a recombinant protein or protein mixture derived from an enterically transmitted nonA/nonB viral hepatitis agent whose genome contains a region which is homologous to the 1.33 kb DNA EcoRI insert present in plasmid pTZKF1(ET1.1) carried in E. coli strain BB4, and having ATCC deposit no. 67717. The vaccine is administered at periodic intervals until a significant titer of anti-ET-NANB antibody is detected in the serum. The vaccine is intended to protect against ET-NANB infection.

Particularly preferred are vaccines prepared using proteins expressed by the 406.3-2 and 406.4-2 clones described herein and equivalents thereof, including fragments of the expressed proteins. Since these clones have already been demonstrated to be reactive with a variety of human HEV-positive sera, their utility in protecting against a variety of HEV strains is indicated.

D. Prophylactic and Therapeutic Antibodies and Antisera

An addition to use as a vaccine, the compositions can be used to prepare antibodies to ET-NANB virus particles. The antibodies can be used directly as antiviral agents. To prepare antibodies, a host animal is immunized using the virus particles or, as appropriate, non-particle antigens native to the virus particle are bound to a carrier as described above for vaccines. The host serum or plasma is collected following an appropriate time interval to provide a composition comprising antibodies reactive with the virus particle. The gamma globulin fraction or the IgG antibodies can De obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the FC portion of a foreign species antibody or using an antibody of the same species as the host animal, for example, the use of antibodies from human/human hybridomas.

The antibodies can also be used as a means of enhancing the immune response since antibody-virus complexes are recognized by macrophages. The antibodies can be administered in amounts similar to those used for other therapeutic administrations of antibody. For example, pooled gamma globulin is administered at 0.02–0.1 ml/lb body weight during the early incubation of other viral diseases such as rabies, measles and hepatitis B to interfere with viral entry into cells. Thus, antibodies reactive with the ET-NANB virus particle can be passively administered alone or in conjunction with another anti-viral agent to a host infected with an ET-NANB virus to enhance the immune response and/or the effectiveness of an antiviral drug.

Alternatively, anti-ET-NANB-virus antibodies can be induced by administering anti-idiotype antibodies as immunogens. Conveniently, a purified anti-ET-NANB-virus antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-ET-NANB virus antibodies, or by affinity chromatography using anti-ET-NANB-virus antibodies bound to the affinity matrix. The anti-idiotype antibodies produced are similar in conformation to the authentic ET-NANB antigen and may be used to prepare an ET-NANB vaccine rather than using a ET-NANB particle antigen.

When used as a means of inducing anti-ET-NANB virus antibodies in a patient, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable. The anti-idiotype method of induction of anti-ET-NANB virus antibodies can alleviate problems which may be caused by passive administration of anti-ET-NANB-virus antibodies, such as an adverse immune response, and those associated with administration of purified blood components, such as infection with as yet undiscovered viruses.

The ET-NANB derived proteins of the invention are also intended for use in producing antiserum designed for pre- or post-exposure prophylaxis. Here an ET-NANB protein, or mixture of proteins is formulated with a suitable adjuvant and administered by injection to human volunteers, according to known methods for producing human antisera. Antibody response to the injected proteins is monitored, during a several-week period following immunization, by periodic serum sampling to detect the presence an anti-ET-NANB serum antibodies, as described in Section IIA above.

The antiserum from immunized individuals may be administered as a pre-exposure prophylactic measure for individuals who are at risk of contracting infection. The antiserum is also useful in treating an individual post-exposure, analogous to the use of high titer antiserum against hepatitis B virus for post-exposure prophylaxis.

E. Monoclonal Antibodies

For both in vivo use of antibodies to ET-NANB virus particles and proteins and anti-idiotype antibodies and diagnostic use, it may be preferable to use monoclonal antibodies. Monoclonal anti-virus particle antibodies or anti-idiotype antibodies can be produced as follows. The spleen or lymphocytes from an immunized animal are removed and immortalized or used to prepare hybridomas by methods known to those skilled in the art. To produce a human-human hybridoma, a human lymphocyte donor is selected. A donor known to be infected with a ET-NANB virus (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-virus particle antibodies, the antibodies must bind to ET-NANB virus particles. For monoclonal anti-idiotype antibodies, the antibodies must bind to anti-virus particle antibodies. Cells producing antibodies of the desired specificity are selected.

The following examples illustrate various aspects of the invention, but are in no way intended to limit the scope thereof.

MATERIAL

The materials used in the following Examples were as follows:

Enzymes: DNAse I and alkaline phosphatase were obtained from Boehringer Mannheim Biochemicals (BMB, Indianapolis, Ind.); EcoRI, EcoRI methylase, DNA ligase, and DNA Polymerase I, from New England Biolabs (NEB, Beverly Ma.); and RNase A was obtained from Sigma (St. Louis, Mont.)

Other reagents: EcoRI linkers were obtained from NEB; and nitro blue tetrazolium (NBT), S-bromo-4-chloro-3-indolyl phosphate (BCIP) S-bromo-4-chloro-3-indolyl-B-D-galactopyranoside (Xgal) and isopropyl B-D-thiogalactopyranoside (IPTG) were obtained from Sigma.

cDNA synthesis kit and random priming labeling kits are available from Boehringer-Mannheim Biochemical (BMB, Indianapolis, Ind.).

EXAMPLE 1

Preparing CDNA Library

A. Source of ET-NANB Virus

Two cynomolgus monkeys (cynos) were intravenously injected with a 10% suspension of a stool pool obtained from a second-passage cyno (cyno #37) infected with a strain of ET-NANB virus isolated from Burma cases whose stools were positive for ET-NANB, as evidenced by binding of 27–34 nm virus-like particles (VLPs) in the stool to immune serum from a known ETNANB patient. The animals developed elevated levels of alanine aminotransferase (ALT) between 24–36 days after inoculation, and one excreted 27–34 nm VLPS in its bile in the pre-acute phase of infection.

The bile duct of each infected animal was cannulated and about 1–3 cc of bile was collected daily. RNA was extracted from one bile specimen (cyno #121) by hot phenol extraction, using a standard RNA isolation procedure. Double-strand cDNA was formed from the isolated RNA by a random primer for first-strand generation, using a cDNA synthesis kit obtained from Boehringer-Mannheim (Indianapolis, Ind.).

B. Cloning the Duplex Fragments

The duplex CDNA fragments were blunt-ended with T4 DNA polymerase under standard conditions (Maniatis, p. 118), then extracted with phenol/chloroform and precipitated with ethanol. The blunt-ended material was ligated with EcoRI linkers under standard conditions (Maniatis, pp. 396–397) and digested with EcoRI to remove redundant linker ends. Non-ligated linkers were removed by sequential isopropanol precipitation.

Lambda gt10 phage vector (Huynh) was obtained-from Promega Biotec (Madison, Wis.). This cloning vector has a unique EcoRI cloning site in the phage CI repressor gene. The cDNA fragments from above were introduced into the EcoRI site by mixing 0.5–1.0 $\mu$g EcoRI-cleaved gt10, 0.5–3 $\mu$l of the above duplex fragments, 0.5 $\mu$l 10×ligation buffer, 0.5 $\mu$l ligase (200 units), and distilled water to 5 $\mu$l. The mixture was incubated overnight at 14° C., followed by in vitro packaging, according to standard methods (Maniatis, pp. 256–268).

The packaged phage were used to infect an E. coli hfl strain, such as strain HG415. Alternatively, E. coli, strain C600 hfl available from Promega Biotec, Madison, Wis., could be used. The percentage of recombinant plaques obtained with insertion of the EcoRI-ended fragments was less than 5% by analysis of 20 random plaques.

The resultant cDNA library was plated and phage were eluted from the selection plates by addition of elution buffer. After DNA extraction from the phage, the DNA was digested with EcoRI to release the heterogeneous insert population, and the DNA fragments were fractionated on agarose to remove phage fragments. The 500–4,000 basepair inserts were isolated and recloned into lambda gt10 as above, and the packaged phage was used to infect E. coli strain HG415. The percentage of successful recombinants was greater than 95%. The phage library was plated on E. coli strain HG415, at about 5,000 plaques/plate, on a total of 8 plates.

67

EXAMPLE 2
Selecting ET-NANB Cloned Fragments
A. CDNA Probes

Duplex cDNA fragments from noninfected and ETNANB-infected cynomolgus monkeys were prepared as in Example 1. The cDNA fragments were radiolabeled by random priming, using a random-priming labeling kit obtained from Boehringer-Mannheim (Indianapolis, Ind.).

B. Clone Selection

The plated CDNA library from Example 1 was transferred to each of two nitrocellulose filters, and the phage DNA was fixed on the filters by baking, according to standard methods (Maniatis, pp. 320323). The duplicate filters were hybridized with either infected-source or control CDNA probes from above. Autoradiographs of the filters were examined to identify library clones which hybridized with radiolabeled CDNA probes from infected source only, i.e., did not hybridize with cDNA probes from the non-infected source. Sixteen such clones, out of a total of about 40,000 clones examined, were identified by this subtraction selection method.

Each of the sixteen clones was picked and replated at low concentration on an agar plate. The clones on each plate were transferred to two nitro-cellulose ag duplicate lifts, and examined for hybridization to radiolabeled cDNA probes from infected and noninfected sources, as above. Clones were selected which showed selective binding for infected-source probes (i.e., binding with infected-source probes and substantially no binding with non-infected-source probes). One of the clones which bound selectively to probe from infected source was isolated for further study. The selected vector was identified as lambda gt10-1.1, indicated in FIG. 1.

EXAMPLE 3
ET-NANB Sequence

Clone lambda gt10-1.1 from Example 2 was digested with EcoRI to release the heterologous insert, which was separated from the vector fragments by gel electrophoresis. The electrophoretic mobility of the fragment was consistent with a 1.33 kb fragment. This fragment, which contained EcoRI ends, was inserted into the EcoRI site of a pTZKF1 vector, whose construction and properties are described in co-owned U.S. patent application for "Cloning Vector System and Method for Rare Clone Identification", Ser. No. 125,650, filed Nov. 25, 1987. Briefly, and as illustrated in FIG. 1, this plasmid contains a unique EcoRI site adjacent a T7 polymerase promoter site, and plasmid and phage origins of replication. The sequence immediately adjacent each side of the EcoRI site is known. E. coli BB4 bacteria, obtained from Stratagene (La Jolla, Calif., were transformed with the plasmid.

Radiolableled ET-NANB probe was prepared by excising the 1.33 kb insert from the lambda gt10-1.1 phage in Example 2, separating the fragment by gel electrophoresis, and randomly labeling as above. Bacteria transfected with the above pTZKF1 and containing the desired ET-NANB insert were selected by ET-NANB probe, according to methods outlined in Example 2.

One bacterial colony containing a successful recombinant was used for sequencing a portion of the 1.33 kb insert. This isolate, designated pTZKF1(ET1.1), has been deposited with the American Type Culture Collection, and is identified by ATCC deposit no. 67717. Using a standard dideoxy sequencing procedure, and primers for the sequences flanking the EcoRI site, about 200–250 basepairs of sequence from the 5'-end region and 3'-end region of the insert were obtained. The sequences are given above in Section II. Later sequencing by the same techniques gave the full sequence in both directions, also given above.

68

EXAMPLE 4
Detecting ET-NANB Sequences cDNA fragment mixtures from the bile of noninfected and ET-NANB-infected cynomolgus monkeys were prepared as above. The cDNA fragments obtained from human stool samples were prepared as follows. Thirty mg of a 10% stool suspension gained from an individual from Mexico diagnosed as infected with ET-NANB as a result of an ET-NANB outbreak, and a similar volume of stool from a healthy, non-infected individual, were layered over a 30% sucrose density gradient cushion, and centrifuged at 25,000×g for 6 hr in an SW27 rotor, at 15° C. The pelleted material from the infected-source stool contained 27–34 nm VLP particles characteristic of ET-NANB infection in the infected-stool sample. RNA was isolated from the sucrose-gradient pellets in both the infected and non-infected samples, and the isolated RNA was used to produce cDNA fragments as described in Example 1.

The CDNA fragment mixtures from infected and non-infected bile source, and from infected and non-infected human-stool source were each amplified by a novel linker/primer replication method described in co-owned patent application Ser. No. 07/208,512 for "DNA Amplification and Subtraction Technique," filed Jun. 17, 1988. Briefly, the fragments in each sample were blunt-ended with KNA Pol I then extracted with phenol/chloroform and precipitated with ethanol. The blunt-ended material was ligated with linkers having the following sequence (top or 5' sequence has SEQ ID NO.21; bottom or 3'sequence has SEQ ID NO:22):

```
 5'-GGAATTCGCGGCCGCTCG-3'
3'-TTCCTTAAGCGCCGGCGAGC-5'
```

The duplex fragments were digested with NruI to remove linker timers, mixed with a primer having the sequence 5'-GGAATTCGCGGCCGCTCG-3', and then heat denatured and cooled to room temperature to form single-strand DNA/primer complexes. The complexes were replicated to form duplex fragments by addition of Thermus aquaticus (Taq) polymerase and all four deoxynucleotides. The replication procedures, involving successive strand denaturation, formation of strand/primer complexes, and replication, was repeated 25 times.

The amplified CDNA sequences were fractionated by agarose gel electrophoresis, using a 2% agarose matrix. After transfer of the DNA fragments from the agarose gels to nitrocellulose paper, the filters were hybridized to a random-labeled 32p probe prepared by (i) treating the pTZKF1(ET1.1) plasmid from above with EcoRI, (ii) isolating the released 1.33 kb ET-NANB fragment, and (iii) randomly labeling the isolated fragment. The probe hybridization wag performed by conventional Southern blotting methods (Maniatis, pp. 382–389). FIG. 2 shows the hybridization pattern obtained with cDNAs from infected (I) and non-infected (N) bile sources (2A) and from infected (I) and noninfected (N) human stool sources (2B). As seen, the ET-NANB probe hybridized with fragments obtained from both of the infected sources, but was non-homologous to sequences obtained from either of the non-infected sources, thus confirming the specificity of derived sequence.

Southern blots of the radiolabeled 1.33 kb fragment with genomic DNA fragments from both human and cynomolgus-monkey DNA were also prepared. No probe hybridization to either of the genomic fragment mixtures was observed, confirming that the ET-NANB sequence is exogenous to either human or cynomolgus genome.

EXAMPLE 5
Expressing ET-NANB Proteins
A. Preparing ET-NANB Coding Sequences The pTZKF1(ET1.1) plasmid from Example 2 was digested with EcoRI to release the 1.33 kb ET-NANB insert which was purified from the linearized plasmid by gel electrophoresis. The purified fragment was suspended in a standard digest buffer (0.5 M Tris HCl, pH 7.5; 1 mg/ml BSA; 10 mM MnC12) to a concentration of about 1 mg/ml and digested with DNAse I at room temperature for about 5 minutes. These reaction conditions were determined from a prior calibration study, in which the incubation time required to produce predominantly 100–300 basepair fragments was determined. The material was extracted with phenol/chloroform before ethanol precipitation.

The fragments in the digest mixture were blunt-ended and ligated with EcoRI linkers as in Example 1. The resultant fragments were analyzed by electrophoresis (5–10 V/cm) on 1.2% agarose gel, using PhiX174/HaeIII and lambda/HindIII size markers. The 100–300 bp fraction was eluted onto NA45 strips (Schleicher and Schuell), which were then placed into 1.5 ml microtubes with eluting solution (1 M NaCl, 50 mM arginine, pH 9.0), and incubated at 67° C. for 30–60 minutes. The eluted DNA was phenol/chloroform extracted and then precipitated with two volumes of ethanol. The pellet was resuspended in 20 μl TE (0.01 M Tris HCl, pH 7.5, 0.001 M EDTA).

B. Cloning in an Expression Vector

Lambda gt11 phage vector (Huynh) was obtained from Promega Biotec (Madison, Wis.). This cloning vector has a unique EcoRI cloning site 53 base pairs upstream from the beta-galactosidase translation termination codon. The genomic fragments from above, provided either directly from coding sequences (Example 5) or after amplification of cDNA (Example 4), were introduced into the EcoRI site by mixing 0.5–1.0 μg EcoRI-cleaved gt11, 0.3–3 μl of the above sized fragments, 0.5 μl 10×ligation buffer (above), 0.5 μl ligase (200 units), and distilled water to 5 μl. The mixture was incubated overnight at 14° C., followed by in vitro packaging, according to standard methods (Maniatis, pp. 256–268).

The packaged phage were used to infect *E. coli* strain KM392, obtained from Dr. Kevin Moore, DNAX (Palo Alto, Calif.). Alternatively, *E. Coli* strain Y1090, available from the American Type Culture Collection (ATCC #37197), could be used. The infected bacteria were plated and the resultant colonies were checked for loss of beta-galactosidase activity-(clear plaques) in the presence of X-gal using a standard X-gal substrate plaque assay method (Maniatis). About 50% of the phage plaques showed loss of beta-galactosidase enzyme activity (recombinants).

C. Screening for ET-NANB Recombinant Proteins

ET-NANB convalescent antiserum was obtained from patients infected during documented ET-NANB outbreaks in Mexico, Borneo, Pakistan, Somalia, and Burma. The sera were immunoreactive with VLPs in stool specimens from each of several other patients with ET-NANB hepatitis.

A lawn of *E. coli* KM392 cells infected with about 104 pfu of the phage stock from above was prepared on a 150 mm plate and incubated, inverted, for 5–8 hours at 37° C. The lawn was overlaid with a nitrocellulose sheet, causing transfer of expressed ETNANB recombinant protein from the plaques to the paper. The plate and filter were indexed for matching corresponding plate and filter positions.

The filter was washed twice in TBST buffer (10 mM Tris, pH 8.0, 150 mM NaCl, 0.05% Tween 20), blocked with AIB (TBST buffer with 1% gelatin), washed again in TBST, and incubated overnight after addition of antiserum (diluted to 1:50 in AIB, 12–15 ml/plate). The sheet was washed twice in TBST and then contacted with enzyme-labeled anti-human antibody to attach the labeled antibody at filter sites containing antigen recognized by the antiserum. After a final washing, the filter was developed in a substrate medium containing 33 μl NBT (50 mg/ml stock solution maintained at 4° C.) mixed with 16 μl BCIP (50 mg/ml stock solution maintained at 4° C.) in 5 ml of alkaline phosphatase buffer (100 mM Tris, 9.5, 100 mM NaCl, 5 mM MgC12). Purple color appeared at points of antigen production, as recognized by the antiserum.

D. Screening Plating

The areas of antigen production determined in the previous step were replated at about 100–200 pfu on an 82 mm plate. The above steps, beginning with a 5–8 hour incubation, through NBT-BCIP development, were repeated in order to plaque purify phage secreting an antigen capable of reacting with the ET-NANB antibody. The identified plaques were picked and eluted in phage buffer (Maniatis, p. 443).

E. Epitope Identification

A series of subclones derived from the original pTZKF1 (ET1.1) plasmid from Example 2 were isolated using the same techniques described above. Each of these five subclones were immunoreactive with a pool of anti-ET antisera noted in C. The subclones contained short sequences from the "reverse" sequence set forth previously. The beginning and ending points of the sequences in the subclones (relative to the full "reverse" sequence), are identified in the table below.

TABLE 1

| | Position in "Reverse" Sequence | |
|---|---|---|
| Subclone | 5'-end | 3'-end |
| Y1 | 522 | 643 |
| Y2 | 594 | 667 |
| Y3 | 508 | 665 |
| Y4 | 558 | 752 |
| Y5 | 545 | 665 |

Since all of the gene sequences identified in the table must contain the coding sequence for the epitope, it is apparent that the coding sequence for the epitope falls in the region between nucleotide 594 (5'-end) and 643 (3'-end). Genetic sequences equivalent to and complementary to this relatively short sequence are therefore particularly preferred aspects of the present invention, as are peptides produced using this coding region.

A second series of clones identifying an altogether different epitope was isolated with only Mexican serum.

TABLE 2

| | Position in "Forward" Sequence | |
|---|---|---|
| Subclone | 5' end | 3' end |
| ET 2-2 | 2 | 193 |
| ET 8-3 | 2 | 135 |
| ET 9-1 | 2 | 109 |
| ET 13-1 | 2 | 101 |

The coding system for this epitope falls between nucleotide 2 (S-end) and 101 (3-end). Genetic sequences related to this short sequence are therefore also preferred, as are peptides produced using this coding region.

Two particularly preferred subclones for use in preparing polypeptides containing epitopes specific for HEV are the 406.3-2 and 406.4-2 clones whose sequences are set forth above. These sequences were isolated from an amplified cDNA library derived from a Mexican stool. Using the techniques described in this section, polypeptides expressed by these clones have been tested for immunoreactivity against a number of different human HEV-positive sera obtained from sources around the world. As shown in Table 3 below, 8 sera immunoreactive with the polypeptide expressed by the 406.4-2, and 6 sera immunoreacted with polypeptide expressed by the 406.3-2 clone.

For comparison, the Table also shows reactivity of the various human sera with the Y2 clone identified in Table 1 above. Only one of the sera reacted with the polypeptide expressed by this clone. No immunoreactivity was seen for normal expression products of the gt11 vector.

TABLE 3

Immunoreactivity of HEV Recombinant Proteins: Human Sera

| Sera | Source | Stage[1] | 406.3-2 | 406.4-2 | Y2 | λgtll |
|---|---|---|---|---|---|---|
| FVH-21 | Burma | A | – | – | – | – |
| FVH-8 | Burma | A | – | + | + | – |
| SOM-19 | Somalia | A | + | + | – | – |
| SOM-20 | Somalia | A | + | + | – | – |
| IM-35 | Borneo | A | + | + | – | – |
| IM-36 | Borneo | A | – | – | – | – |
| PAK-1 | Pakistan | A | + | + | – | – |
| FFI-4 | Mexico | A | + | + | – | – |
| FFI--125 | Mexico | A | – | + | – | – |
| F 387 IC | Mexico | C | + | + | ND | – |
| Normal | U.S.A. | – | – | – | – | – |

[1]A = acute; C = convalescent

While the invention has been described with reference to particular embodiments, methods, construction and use, it will be apparent to those skilled in the art that various changes and modifications can be made without departing from the invention.

What is claimed is:

1. A method for detecting the presence of an enterically transmitted nonA/nonB hepatitis viral agent in a biological sample, comprising preparing a mixture of duplex DNA fragments derived from the sample, denaturing the duplex fragments, adding to the denatured DNA fragments, a pair of single-strand primers derived from nonhomologous regions of opposite strands of a DNA duplex fragment derived from an enterically transmitted viral hepatitis agent whose genome contains a region which is homologous to the 1.33 kb DNA EcoRI insert present in plasmid pTZKF1(ET1.1) carried in *E. coli* strain BB4, and having ATCC deposit no. 67717, hybridizing said primers to homologous-sequence region of opposite strands of such duplex DNA fragments derived from enterically transmitted nonA/nonB hepatitis agent, reacting the primed fragment strands with DNA polymerase in the presence of DNA nucleotides, to form new DNA duplexes containing the primer sequences, and repeating said denaturing, adding, hybridizing and reacting steps, until a desired degree of amplification of sequences is achieved.

2. The method of claim 1, wherein the primers are derived from opposite strands of the EcoRI duplex insert in said plasmid.

3. The method of claim 1, for detecting the presence of viral agent in a sample of cultured cells infected with the agent.

4. In a method of isolating an enterically transmitted nonA/nonB viral agent or a nucleic acid fragment produced by the agent, an improvement which comprises: utilizing, as a source of said agent, bile obtained from a human or cynomolgus monkey having an active infection of enterically transmitted non-A/non-B hepatitis.

5. The method of claim 4, wherein the bile is obtained from an infected cynomolgus monkey.

* * * * *

SEQUENCE LISTING

```
(1) GENERAL INFORMATION:

(iii) NUMBER OF SEQUENCES: 20

(2) INFORMATION FOR SEQ ID NO:1:

(i) SEQUENCE CHARACTERISTICS:
          (A) LENGTH: 1295 base pairs
          (B) TYPE: nucleic acid
          (C) STRANDEDNESS: double
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: 1.33 kb EcoRI insert of ET1.1,
               forward sequence (ix) FEATURE:
          (A) NAME/KEY: CDS
          (B) LOCATION: 1..1293

(ix) FEATURE:
          (A) NAME/KEY: CDS
          (B) LOCATION: 2..1294

(ix) FEATURE:
          (A) NAME/KEY: CDS
          (B) LOCATION: 3..1295

(xi) SEQUENCE DESCRIPTION: SEQ ID NO:1:

AGACCTGTCC CTGTTGCAGC TGTTCTACCA CCCTGCCCCG AGCTCGAACA G GGCCTTCTC     60

TACCTGCCCC AGGAGCTCAC CACCTGTGAT AGTGTCGTAA CATTTGAATT A ACAGACATT    120

GTGCACTGCC GCATGGCCGC CCCGAGCCAG CGCAAGGCCG TGCTGTCCAC A CTCGTGGGC    180
```

```
CGCTACGGCG GTCGCACAAA GCTCTACAAT GCTTCCCACT CTGATGTTCG C GACTCTCTC    240
GCCCGTTTTA TCCCGGCCAT GGCCCCGTA CAGGTTACAA CTTGTGAATT G TACGAGCTA    300
GTGGAGGCCA TGGTCGAGAA GGGCCAGGAT GGCTCCGCCG TCCTTGAGCT T GATCTTTGC    360
AACCGTGACG TGTCCAGGAT CACCTTCTTC CAGAAAGATT GTAACAAGTT C ACCACAGGT    420
GAGACCATTG CCCATGGTAA AGTGGGCCAG GGCATCTCGG CCTGGAGCAA G ACCTTCTGC    480
GCCCTCTTTG GCCCTTGGTT CCGCGCTATT GAGAAGGCTA TTCTGGCCCT G CTCCCTCAG    540
GGTGTGTTTT ACGGTGATGC CTTTGATGAC ACCGTCTTCT CGGCGGCTGT G GCCGCAGCA    600
AAGGCATCCA TGGTGTTTGA GAATGACTTT TCTGAGTTTG ACTCCACCCA G AATAACTTT    660
TCTCTGGGTC TAGAGTGTGC TATTATGGAG GAGTGTGGGA TGCCGCAGTG G CTCATCCGC    720
CTGTATCACC TTATAAGGTC TGCGTGGATC TTGCAGGCCC CGAAGGAGTC T CTGCGAGGG    780
TTTTGGAAGA ACACTCCGG TGAGCCCGGC ACTCTTCTAT GGAATACTGT C TGGAATATG    840
GCCGTTATTA CCCACTGTTA TGACTTCCGC GATTTTCAGG TGGCTGCCTT T AAAGGTGAT    900
GATTCGATAG TGCTTTGCAG TGAGTATCGT CAGAGTCCAG GAGCTGCTGT C CTGATCGCC    960
GGCTGTGGCT TGAAGTTGAA GGTAGATTTC CGCCCGATCG GTTTGTATGC A GGTGTTGTG   1020
GTGGCCCCCG GCCTTGGCGC GCTCCCTGAT GTTGTGCGCT TCGCCGGCCG G CTTACCGAG   1080
AAGAATTGGG GCCCTGGCCC TGAGCGGGCG GAGCAGCTCC GCCTCGCTGT T AGTGATTTC   1140
CTCCGCAAGC TCACGAATGT AGCTCAGATG TGTGTGGATG TTGTTTCCCG T GTTTATGGG   1200
GTTTCCCCTG GACTCGTTCA TAACCTGATT GGCATGCTAC AGGCTGTTGC T GATGGCAAG   1260
GCACATTTCA CTGAGTCAGT AAAACCAGTG CTCGA                              1295

(2) INFORMATION FOR SEQ ID NO:2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:2:

Arg Pro Val Pro Val Ala Ala Val Leu Pro P ro Cys Pro Glu Leu Glu
  1               5                  10                  15

Gln Gly Leu Leu Tyr Leu Pro Gln Glu Leu T hr Thr Cys Asp Ser Val
             20                  25                  30

Val Thr Phe Glu Leu Thr Asp Ile Val His C ys Arg Met Ala Ala Pro
         35                  40                  45

Ser Gln Arg Lys Ala Val Leu Ser Thr Leu V al Gly Arg Tyr Gly Gly
     50                  55                  60

Arg Thr Lys Leu Tyr Asn Ala Ser His Ser A sp Val Arg Asp Ser Leu
 65                  70                  75                  80

Ala Arg Phe Ile Pro Ala Ile Gly Pro Val G ln Val Thr Thr Cys Glu
                 85                  90                  95

Leu Tyr Glu Leu Val Glu Ala Met Val Glu L ys Gly Gln Asp Gly Ser
            100                 105                 110

Ala Val Leu Glu Leu Asp Leu Cys Asn Arg A sp Val Ser Arg Ile Thr
        115                 120                 125

Phe Phe Gln Lys Asp Cys Asn Lys Phe Thr T hr Gly Glu Thr Ile Ala
    130                 135                 140

His Gly Lys Val Gly Gln Gly Ile Ser Ala T rp Ser Lys Thr Phe Cys
```

```
145                 150                 155                 160
Ala Leu Phe Gly Pro Trp Phe Arg Ala Ile Glu Lys Ala Ile Leu Ala
                165                 170                 175
Leu Leu Pro Gln Gly Val Phe Tyr Gly Asp Ala Phe Asp Asp Thr Val
                180                 185                 190
Phe Ser Ala Ala Val Ala Ala Ala Lys Ala Ser Met Val Phe Glu Asn
                195                 200                 205
Asp Phe Ser Glu Phe Asp Ser Thr Gln Asn Asn Phe Ser Leu Gly Leu
    210                 215                 220
Glu Cys Ala Ile Met Glu Glu Cys Gly Met Pro Gln Trp Leu Ile Arg
225                 230                 235                 240
Leu Tyr His Leu Ile Arg Ser Ala Trp Ile Leu Gln Ala Pro Lys Glu
                245                 250                 255
Ser Leu Arg Gly Phe Trp Lys Lys His Ser Gly Glu Pro Gly Thr Leu
                260                 265                 270
Leu Trp Asn Thr Val Trp Asn Met Ala Val Ile Thr His Cys Tyr Asp
                275                 280                 285
Phe Arg Asp Phe Gln Val Ala Ala Phe Lys Gly Asp Asp Ser Ile Val
    290                 295                 300
Leu Cys Ser Glu Tyr Arg Gln Ser Pro Gly Ala Ala Val Leu Ile Ala
305                 310                 315                 320
Gly Cys Gly Leu Lys Leu Lys Val Asp Phe Arg Pro Ile Gly Leu Tyr
                325                 330                 335
Ala Gly Val Val Val Ala Pro Gly Leu Gly Ala Leu Pro Asp Val Val
                340                 345                 350
Arg Phe Ala Gly Arg Leu Thr Glu Lys Asn Trp Gly Pro Gly Pro Glu
                355                 360                 365
Arg Ala Glu Gln Leu Arg Leu Ala Val Ser Asp Phe Leu Arg Lys Leu
    370                 375                 380
Thr Asn Val Ala Gln Met Cys Val Asp Val Val Ser Arg Val Tyr Gly
385                 390                 395                 400
Val Ser Pro Gly Leu Val His Asn Leu Ile Gly Met Leu Gln Ala Val
                405                 410                 415
Ala Asp Gly Lys Ala His Phe Thr Glu Ser Val Lys Pro Val Leu
                420                 425                 430
```

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: linker - top (5') sequence (xi) SEQUENCE DESCRIPTION: SEQ ID NO:3:

GGAATTCGCG GCCGCTCG                                           18

(2) INFORMATION FOR SEQ ID NO:4:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: linker - bottom (3') sequence (xi) SEQUENCE DESCRIPTION: SEQ ID NO:4:

CGAGCGGCCG CGAATTCCTT                                                   20

(2) INFORMATION FOR SEQ ID NO:5:

(i) SEQUENCE CHARACTERISTICS:
        (A) LENGTH: 1295 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: 1.33 kb EcoRI insert of ET1.1,
            reverse sequence (xi) SEQUENCE DESCRIPTION: SEQ ID NO:5:

TCGAGCACTG GTTTTACTGA CTCAGTGAAA TGTGCCTTGC CATCAGCAAC A GCCTGTAGC      60

ATGCCAATCA GGTTATGAAC GAGTCCAGGG GAAACCCCAT AAACACGGGA A ACAACATCC    120

ACACACATCT GAGCTACATT CGTGAGCTTG CGGAGGAAAT CACTAACAGC G AGGCGGAGC    180

TGCTCCGCCC GCTCAGGGCC AGGGCCCCAA TTCTTCTCGG TAAGCCGGCC G GCGAAGCGC    240

ACAACATCAG GGAGCGCGCC AAGGCCGGGG GCCACCACAA CACCTGCATA C AAACCGATC    300

GGGCGGAAAT CTACCTTCAA CTTCAAGCCA CAGCCGGCGA TCAGGACAGC A GCTCCTGGA    360

CTCTGACGAT ACTCACTGCA AAGCACTATC GAATCATCAC CTTTAAAGGC A GCCACCTGA    420

AAATCGCGGA AGTCATAACA GTGGGTAATA ACGGCCATAT TCCAGACAGT A TTCCATAGA    480

AGAGTGCCGG GCTCACCGGA GTGTTTCTTC CAAAACCCTC GCAGAGACTC C TTCGGGGCC    540

TGCAAGATCC ACGCAGACCT TATAAGGTGA TACAGGCGGA TGAGCCACTG C GGCATCCCA    600

CACTCCTCCA TAATAGCACA CTCTAGACCC AGAGAAAAGT TATTCTGGGT G GAGTCAAAC    660

TCAGAAAAGT CATTCTCAAA CACCATGGAT GCCTTTGCTG CGGCCACAGC C GCCGAGAAG    720

ACGGTGTCAT CAAAGGCATC ACCGTAAAAC ACACCCTGAG GGAGCAGGGC C AGAATAGCC    780

TTCTCAATAG CGCGGAACCA AGGGCCAAAG AGGGCGCAGA AGGTCTTGCT C CAGGCCGAG    840

ATGCCCTGGC CCACTTTACC ATGGGCAATG GTCTCACCTG TGGTGAACTT G TTACAATCT    900

TTCTGGAAGA AGGTGATCCT GGACACGTCA CGGTTGCAAA GATCAAGCTC A AGGACGGCG    960

GAGCCATCCT GGCCCTTCTC GACCATGGCC TCCACTAGCT CGTACAATTC A CAAGTTGTA   1020

ACCTGTACGG GGCCAATGGC CGGGATAAAA CGGGCGAGAG AGTCGCGAAC A TCAGAGTGG   1080

GAAGCATTGT AGAGCTTTGT GCGACCGCCG TAGCGGCCCA CGAGTGTGGA C AGCACGGCC   1140

TTGCGCTGGC TCGGGCGGC CATGCGGCAG TGCACAATGT CTGTTAATTC A AATGTTACG   1200

```
ACACTATCAC AGGTGGTGAG CTCCTGGGGC AGGTAGAGAA GGCCCTGTTC G AGCTCGGGG    1260
CAGGGTGGTA GAACAGCTGC AACAGGGACA GGTCT                                1295
```

(2) INFORMATION FOR SEQ ID NO:6:

(i) SEQUENCE CHARACTERISTICS:
        (A) LENGTH: 7195 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: HEV - Burma strain (ix) FEATURE:
        (A) NAME/KEY: CDS
        (B) LOCATION: 28..5106

(ix) FEATURE:
        (A) NAME/KEY: CDS
        (B) LOCATION: 5147..7126

(ix) FEATURE:
        (A) NAME/KEY: CDS
        (B) LOCATION: 5106..5474

(xi) SEQUENCE DESCRIPTION: SEQ ID NO:6:

```
AGGCAGACCA CATATGTGGT CGATGCCATG GAGGCCCATC AGTTTATTAA G GCTCCTGGC     60
ATCACTACTG CTATTGAGCA GGCTGCTCTA GCAGCGGCCA ACTCTGCCCT G GCGAATGCT    120
GTGGTAGTTA GGCCTTTTCT CTCTCACCAG CAGATTGAGA TCCTCATTAA C CTAATGCAA    180
CCTCGCCAGC TTGTTTTCCG CCCCGAGGTT TTCTGGAATC ATCCCATCCA G CGTGTCATC    240
CATAACGAGC TGGAGCTTTA CTGCCGCGCC CGCTCCGGCC GCTGTCTTGA A ATTGGCGCC    300
CATCCCCGCT CAATAAATGA TAATCCTAAT GTGGTCCACC GCTGCTTCCT C CGCCCTGTT    360
GGGCGTGATG TTCAGCGCTG GTATACTGCT CCCACTCGCG GGCCGGCTGC T AATTGCCGG    420
CGTTCCGCGC TGCGCGGGCT TCCCGCTGCT GACCGCACTT ACTGCCTCGA C GGGTTTTCT    480
GGCTGTAACT TTCCCGCCGA GACTGGCATC GCCCTCTACT CCCTTCATGA T ATGTCACCA    540
TCTGATGTCG CCGAGGCCAT GTTCCGCCAT GGTATGACGC GGCTCTATGC C GCCCTCCAT    600
CTTCCGCCTG AGGTCCTGCT GCCCCCTGGC ACATATCGCA CCGCATCGTA T TTGCTAATT    660
CATGACGGTA GGCGCGTTGT GGTGACGTAT GAGGGTGATA CTAGTGCTGG T TACAACCAC    720
GATGTCTCCA ACTTGCGCTC CTGGATTAGA ACCACCAAGG TTACCGGAGA C CATCCCCTC    780
GTTATCGAGC GGGTTAGGGC CATTGGCTGC CACTTTGTTC TCTTGCTCAC G GCAGCCCCG    840
GAGCCATCAC CTATGCCTTA TGTTCCTTAC CCCCGGTCTA CCGAGGTCTA T GTCCGATCG    900
ATCTTCGGCC CGGGTGGCAC CCCTTCCTTA TTCCCAACCT CATGCTCCAC T AAGTCGACC    960
TTCCATGCTG TCCCTGCCCA TATTTGGGAC CGTCTTATGC TGTTCGGGGC C ACCTTGGAT   1020
GACCAAGCCT TTTGCTGCTC CCGTTTAATG ACCTACCTTC GCGGCATTAG C TACAAGGTC   1080
ACTGTTGGTA CCCTTGTGGC TAATGAAGGC TGGAATGCCT CTGAGGACGC C CTCACAGCT   1140
GTTATCACTG CCGCCTACCT TACCATTTGC CACCAGCGGT ATCTCCGCAC C CAGGCTATA   1200
TCCAAGGGGA TGCGTCGTCT GGAACGGGAG CATGCCCAGA AGTTTATAAC A CGCCTCTAC   1260
AGCTGGCTCT TCGAGAAGTC CGGCCGTGAT TACATCCCTG CCGTCAGTT G GAGTTCTAC   1320
```

-continued

```
GCCCAGTGCA GGCGCTGGCT CTCCGCCGGC TTTCATCTTG ATCCACGGGT G TTGGTTTTT    1380
GACGAGTCGG CCCCCTGCCA TTGTAGGACC GCGATCCGTA AGGCGCTCTC A AAGTTTTGC    1440
TGCTTCATGA AGTGGCTTGG TCAGGAGTGC ACCTGCTTCC TTCAGCCTGC A GAAGGCGCC    1500
GTCGGCGACC AGGGTCATGA TAATGAAGCC TATGAGGGGT CCGATGTTGA C CCTGCTGAG    1560
TCCGCCATTA GTGACATATC TGGGTCCTAT GTCGTCCCTG GCACTGCCCT C CAACCGCTC    1620
TACCAGGCCC TCGATCTCCC CGCTGAGATT GTGGCTCGCG CGGGCCGGCT G ACCGCCACA    1680
GTAAAGGTCT CCCAGGTCGA TGGGCGGATC GATTGCGAGA CCCTTCTTGG T AACAAAACC    1740
TTTCGCACGT CGTTCGTTGA CGGGGCGGTC TTAGAGACCA ATGGCCCAGA G CGCCACAAT    1800
CTCTCCTTCG ATGCCAGTCA GAGCACTATG GCCGCTGGCC CTTTCAGTCT C ACCTATGCC    1860
GCCTCTGCAG CTGGGCTGGA GGTGCGCTAT GTTGCTGCCG GCTTGACCA T CGGGCGGTT     1920
TTTGCCCCCG GTGTTTCACC CCGGTCAGCC CCCGGCGAGG TTACCGCCTT C TGCTCTGCC    1980
CTATACAGGT TTAACCGTGA GGCCCAGCGC CATTCGCTGA TCGGTAACTT A TGGTTCCAT    2040
CCTGAGGGAC TCATTGGCCT CTTCGCCCCG TTTTCGCCCG GCATGTTTG G GAGTCGGCT     2100
AATCCATTCT GTGGCGAGAG CACACTTTAC ACCCGTACTT GGTCGGAGGT T GATGCCGTC    2160
TCTAGTCCAG CCCGGCCTGA CTTAGGTTTT ATGTCTGAGC CTTCTATACC T AGTAGGGCC    2220
GCCACGCCTA CCCTGGCGGC CCCTCTACCC CCCCCTGCAC CGGACCCTTC C CCCCCTCCC    2280
TCTGCCCCGG CGCTTGCTGA GCCGGCTTCT GGCGCTACCG CCGGGCCCC G GCCATAACT     2340
CACCAGACGG CCCCGGCACCG CCGCCTGCTC TTCACCTACC CGGATGGCTC T AAGGTATTC   2400
GCCGGCTCGC TGTTCGAGTC GACATGCACG TGGCTCGTTA ACGCGTCTAA T GTTGACCAC    2460
CGCCCTGGCG GCGGGCTTTG CCATGCATTT TACCAAAGGT ACCCCGCCTC C TTTGATGCT    2520
GCCTCTTTTG TGATGCGCGA CGGCGCGGCC GCGTACACAC TAACCCCCCG G CCAATAATT    2580
CACGCTGTCG CCCCTGATTA TAGGTTGGAA CATAACCCAA AGAGGCTTGA G GCTGCTTAT    2640
CGGGAAACTT GCTCCCGCCT CGGCACCGCT GCATACCCGC TCCTCGGGAC C GGCATATAC    2700
CAGGTGCCGA TCGGCCCCAG TTTTGACGCC TGGGAGCGGA ACCACCGCCC C GGGGATGAG    2760
TTGTACCTTC CTGAGCTTGC TGCCAGATGG TTTGAGGCCA ATAGGCCGAC C CGCCCGACT    2820
CTCACTATAA CTGAGGATGT TGCACGGACA GCGAATCTGG CCATCGAGCT T GACTCAGCC    2880
ACAGATGTCG GCCGGGCCTG TGCCGGCTGT CGGGTCACCC CCGGCGTTGT T CAGTACCAG    2940
TTTACTGCAG GTGTGCCTGG ATCCGGCAAG TCCGCTCTA TCACCCAAGC C GATGTGGAC     3000
GTTGTCGTGG TCCCGACGCG TGAGTTGCGT AATGCCTGGC GCCGTCGCGG C TTTGCTGCT    3060
TTTACCCCGC ATACTGCCGC CAGAGTCACC CAGGGGCGCC GGGTTGTCAT T GATGAGGCT    3120
CCATCCCTCC CCCCTCACCT GCTGCTGCTC CACATGCAGC GGGCCGCCAC C GTCCACCTT    3180
CTTGGCGACC CGAACCAGAT CCCAGCCATC GACTTTGAGC ACGCTGGGCT C GTCCCCGCC    3240
ATCAGGCCCG ACTTAGGCCC CACCTCCTGG TGGCATGTTA CCCATCGCTG G CCTGCGGAT    3300
GTATGCGAGC TCATCCGTGG TGCATACCCC ATGATCCAGA CCACTAGCCG G GTTCTCCGT    3360
TCGTTGTTCT GGGGTGAGCC TGCCGTCGGG CAGAAACTAG TGTTCACCCA G GCGGCCAAG    3420
CCCGCCAACC CCGGCTCAGT GACGGTCCAC GAGGCGCAGG GCGCTACCTA C ACGGAGACC    3480
ACTATTATTG CCACAGCAGA TGCCCGGGGC CTTATTCAGT CGTCTCGGGC T CATGCCATT    3540
GTTGCTCTGA CGCGCCACAC TGAGAAGTGC GTCATCATTG ACGCACCAGG C CTGCTTCGC    3600
GAGGTGGGCA TCTCCGATGC AATCGTTAAT AACTTTTTCC TCGCTGGTGG C GAAATTGGT    3660
```

```
CACCAGCGCC CATCAGTTAT TCCCCGTGGC AACCCTGACG CCAATGTTGA C ACCCTGGCT    3720
GCCTTCCCGC CGTCTTGCCA GATTAGTGCC TTCCATCAGT TGGCTGAGGA G CTTGGCCAC    3780
AGACCTGTCC CTGTTGCAGC TGTTCTACCA CCCTGCCCCG AGCTCGAACA G GGCCTTCTC    3840
TACCTGCCCC AGGAGCTCAC CACCTGTGAT AGTGTCGTAA CATTTGAATT A ACAGACATT    3900
GTGCACTGCC GCATGGCCGC CCCGAGCCAG CGCAAGGCCG TGCTGTCCAC A CTCGTGGGC    3960
CGCTACGGCG GTCGCACAAA GCTCTACAAT GCTTCCCACT CTGATGTTCG C GACTCTCTC    4020
GCCCGTTTTA TCCCGGCCAT TGGCCCCGTA CAGGTTACAA CTTGTGAATT G TACGAGCTA    4080
GTGGAGGCCA TGGTCGAGAA GGGCCAGGAT GGCTCCGCCG TCCTTGAGCT T GATCTTTGC    4140
AACCGTGACG TGTCCAGGAT CACCTTCTTC CAGAAAGATT GTAACAAGTT C ACCACAGGT    4200
GAGACCATTG CCCATGGTAA AGTGGGCCAG GGCATCTCGG CCTGGAGCAA G ACCTTCTGC    4260
GCCCTCTTTG GCCCTTGGTT CCGCGCTATT GAGAAGGCTA TTCTGGCCCT G CTCCCTCAG    4320
GGTGTGTTTT ACGGTGATGC CTTTGATGAC ACCGTCTTCT CGGCGGCTGT G GCCGCAGCA    4380
AAGGCATCCA TGGTGTTTGA GAATGACTTT TCTGAGTTTG ACTCCACCCA G AATAACTTT    4440
TCTCTGGGTC TAGAGTGTGC TATTATGGAG GAGTGTGGGA TGCCGCAGTG G CTCATCCGC    4500
CTGTATCACC TTATAAGGTC TGCGTGGATC TTGCAGGCCC CGAAGGAGTC T CTGCGAGGG    4560
TTTTGGAAGA ACACTCCGG TGAGCCCGGC ACTCTTCTAT GGAATACTGT C TGGAATATG    4620
GCCGTTATTA CCCACTGTTA TGACTTCCGC GATTTTCAGG TGGCTGCCTT T AAAGGTGAT    4680
GATTCGATAG TGCTTTGCAG TGAGTATCGT CAGAGTCCAG GAGCTGCTGT C CTGATCGCC    4740
GGCTGTGGCT TGAAGTTGAA GGTAGATTTC CGCCCGATCG GTTTGTATGC A GGTGTTGTG    4800
GTGGCCCCCG GCCTTGGCGC GCTCCCTGAT GTTGTGCGCT TCGCCGGCCG G CTTACCGAG    4860
AAGAATTGGG GCCCTGGCCC TGAGCGGGCG GAGCAGCTCC GCCTCGCTGT T AGTGATTTC    4920
CTCCGCAAGC TCACGAATGT AGCTCAGATG TGTGTGGATG TTGTTTCCCG T GTTTATGGG    4980
GTTTCCCCTG GACTCGTTCA TAACCTGATT GGCATGCTAC AGGCTGTTGC T GATGGCAAG    5040
GCACATTTCA CTGAGTCAGT AAAACCAGTG CTCGACTTGA CAAATTCAAT C TTGTGTCGG    5100
GTGGAATGAA TAACATGTCT TTTGCTGCGC CCATGGGTTC GCGACCATGC G CCCTCGGCC    5160
TATTTTGTTG CTGCTCCTCA TGTTTTTGCC TATGCTGCCC GCGCCACCGC C CGGTCAGCC    5220
GTCTGGCCGC CGTCGTGGGC GGCGCAGCGG CGGTTCCGGC GGTGGTTTCT G GGGTGACCG    5280
GGTTGATTCT CAGCCCTTCG CAATCCCCTA TATTCATCCA ACCAACCCCT T CGCCCCCGA    5340
TGTCACCGCT GCGGCCGGGG CTGGACCTCG TGTTCGCCAA CCCGCCCGAC C ACTCGGCTC    5400
CGCTTGGCGT GACCAGGCCC AGCGCCCCGC CGTTGCCTCA CGTCGTAGAC C TACCACAGC    5460
TGGGGCCGCG CCGCTAACCG CGGTCGCTCC GGCCCATGAC ACCCCGCCAG T GCCTGATGT    5520
CGACTCCCGC GGCGCCATCT TGCGCCGGCA GTATAACCTA TCAACATCTC C CCTTACCTC    5580
TTCCGTGGCC ACCGGCACTA ACCTGGTTCT TTATGCCGCC CCTCTTAGTC C GCTTTTACC    5640
CCTTCAGGAC GGCACCAATA CCCATATAAT GGCCACGGAA GCTTCTAATT A TGCCCAGTA    5700
CCGGGTTGCC CGTGCCACAA TCCGTTACCG CCCGCTGGTC CCCAATGCTG T CGGCGGTTA    5760
CGCCATCTCC ATCTCATTCT GGCCACAGAC CACCACCACC CCGACGTCCG T TGATATGAA    5820
TTCAATAACC TCGACGGATG TTCGTATTTT AGTCCAGCCC GGCATAGCCT C TGAGCTTGT    5880
GATCCCAAGT GAGCGCCTAC ACTATCGTAA CCAAGGCTGG CGCTCCGTCG A GACCTCTGG    5940
GGTGGCTGAG GAGGAGGCTA CCTCTGGTCT TGTTATGCTT TGCATACATG G CTCACTCGT    6000
AAATTCCTAT ACTAATACAC CCTATACCGG TGCCCTCGGG CTGTTGGACT T TGCCCTTGA    6060
```

-continued

```
GCTTGAGTTT CGCAACCTTA CCCCCGGTAA CACCAATACG CGGGTCTCCC G TTATTCCAG    6120

CACTGCTCGC CACCGCCTTC GTCGCGGTGC GGACGGGACT GCCGAGCTCA C CACCACGGC    6180

TGCTACCCGC TTTATGAAGG ACCTCTATTT TACTAGTACT AATGGTGTCG G TGAGATCGG    6240

CCGCGGGATA GCCCTCACCC TGTTCAACCT TGCTGACACT CTGCTTGGCG G CCTGCCGAC    6300

AGAATTGATT TCGTCGGCTG GTGGCCAGCT GTTCTACTCC CGTCCCGTTG T CTCAGCCAA    6360

TGGCGAGCCG ACTGTTAAGT TGTATACATC TGTAGAGAAT GCTCAGCAGG A TAAGGGTAT    6420

TGCAATCCCG CATGACATTG ACCTCGGAGA ATCTCGTGTG GTTATTCAGG A TTATGATAA    6480

CCAACATGAA CAAGATCGGC CGACGCCTTC TCCAGCCCCA TCGCGCCCTT T CTCTGTCCT    6540

TCGAGCTAAT GATGTGCTTT GGCTCTCTCT CACCGCTGCC GAGTATGACC A GTCCACTTA    6600

TGGCTCTTCG ACTGGCCCAG TTTATGTTTC TGACTCTGTG ACCTTGGTTA A TGTTGCGAC    6660

CGGCGCGCAG GCCGTTGCCC GGTCGCTCGA TTGGACCAAG GTCACACTTG A CGGTCGCCC    6720

CCTCTCCACC ATCCAGCAGT ACTCGAAGAC CTTCTTTGTC CTGCCGCTCC G CGGTAAGCT    6780

CTCTTTCTGG GAGGCAGGCA CAACTAAAGC CGGGTACCCT TATAATTATA A CACCACTGC    6840

TAGCGACCAA CTGCTTGTCG AGAATGCCGC CGGGCACCGG GTCGCTATTT C CACTTACAC    6900

CACTAGCCTG GGTGCTGGTC CCGTCTCCAT TTCTGCGGTT GCCGTTTTAG C CCCCCACTC    6960

TGCGCTAGCA TTGCTTGAGG ATACCTTGGA CTACCCTGCC CGCGCCCATA C TTTTGATGA    7020

TTTCTGCCCA GAGTGCCGCC CCCTTGGCCT TCAGGGCTGC GCTTTCCAGT C TACTGTCGC    7080

TGAGCTTCAG CGCCTTAAGA TGAAGGTGGG TAAAACTCGG GAGTTGTAGT T TATTTGCTT    7140

GTGCCCCCCT TCTTTCTGTT GCTTATTTCT CATTTCTGCG TTCCGCGCTC C CTGA         7195
```

(2) INFORMATION FOR SEQ ID NO:7:

(i) SEQUENCE CHARACTERISTICS:
        (A) LENGTH: 1693 amino acids
        (B) TYPE: amino acid
        (D) TOPOLOGY: linear (ii) MOLECULE TYPE: protein (xi) SEQUENCE DESCRIPTION: SEQ ID NO:7:

```
Met Glu Ala His Gln Phe Ile Lys Ala Pro G ly Ile Thr Thr Ala Ile
 1               5                  10                  15

Glu Gln Ala Ala Leu Ala Ala Ala Asn Ser A la Leu Ala Asn Ala Val
                20                  25                  30

Val Val Arg Pro Phe Leu Ser His Gln Gln I le Glu Ile Leu Ile Asn
            35                  40                  45

Leu Met Gln Pro Arg Gln Leu Val Phe Arg P ro Glu Val Phe Trp Asn
        50                  55                  60

His Pro Ile Gln Arg Val Ile Asn Glu L eu Glu Leu Tyr Cys Arg
 65                 70                  75                  80

Ala Arg Ser Gly Arg Cys Leu Glu Ile Gly A la His Pro Arg Ser Ile
                85                  90                  95

Asn Asp Asn Pro Asn Val Val His Arg Cys P he Leu Arg Pro Val Gly
            100                 105                 110

Arg Asp Val Gln Arg Trp Tyr Thr Ala Pro T hr Arg Gly Pro Ala Ala
        115                 120                 125

Asn Cys Arg Arg Ser Ala Leu Arg Gly Leu P ro Ala Ala Asp Arg Thr
    130                 135                 140

Tyr Cys Leu Asp Gly Phe Ser Gly Cys Asn P he Pro Ala Glu Thr Gly
```

-continued

```
145                 150                 155                 160
Ile Ala Leu Tyr Ser Leu His Asp Met Ser Pro Ser Asp Val Ala Glu
                165                 170                 175

Ala Met Phe Arg His Gly Met Thr Arg Leu Tyr Ala Ala Leu His Leu
                180                 185                 190

Pro Pro Glu Val Leu Pro Pro Gly Thr Tyr Arg Thr Ala Ser Tyr
            195                 200                 205

Leu Leu Ile His Asp Gly Arg Arg Val Val Val Thr Tyr Glu Gly Asp
            210                 215                 220

Thr Ser Ala Gly Tyr Asn His Asp Val Ser Asn Leu Arg Ser Trp Ile
225                 230                 235                 240

Arg Thr Thr Lys Val Thr Gly Asp His Pro Leu Val Ile Glu Arg Val
                245                 250                 255

Arg Ala Ile Gly Cys His Phe Val Leu Leu Leu Thr Ala Ala Pro Glu
                260                 265                 270

Pro Ser Pro Met Pro Tyr Val Pro Tyr Pro Arg Ser Thr Glu Val Tyr
                275                 280                 285

Val Arg Ser Ile Phe Gly Pro Gly Gly Thr Pro Ser Leu Phe Pro Thr
                290                 295                 300

Ser Cys Ser Thr Lys Ser Thr Phe His Ala Val Pro Ala His Ile Trp
305                 310                 315                 320

Asp Arg Leu Met Leu Phe Gly Ala Thr Leu Asp Asp Gln Ala Phe Cys
                325                 330                 335

Cys Ser Arg Leu Met Thr Tyr Leu Arg Gly Ile Ser Tyr Lys Val Thr
                340                 345                 350

Val Gly Thr Leu Val Ala Asn Glu Gly Trp Asn Ala Ser Glu Asp Ala
                355                 360                 365

Leu Thr Ala Val Ile Thr Ala Ala Tyr Leu Thr Ile Cys His Gln Arg
                370                 375                 380

Tyr Leu Arg Thr Gln Ala Ile Ser Lys Gly Met Arg Arg Leu Glu Arg
385                 390                 395                 400

Glu His Ala Gln Lys Phe Ile Thr Arg Leu Tyr Ser Trp Leu Phe Glu
                405                 410                 415

Lys Ser Gly Arg Asp Tyr Ile Pro Gly Arg Gln Leu Glu Phe Tyr Ala
                420                 425                 430

Gln Cys Arg Arg Trp Leu Ser Ala Gly Phe His Leu Asp Pro Arg Val
                435                 440                 445

Leu Val Phe Asp Glu Ser Ala Pro Cys His Cys Arg Thr Ala Ile Arg
450                 455                 460

Lys Ala Leu Ser Lys Phe Cys Cys Phe Met Lys Trp Leu Gly Gln Glu
465                 470                 475                 480

Cys Thr Cys Phe Leu Gln Pro Ala Glu Gly Ala Val Gly Asp Gln Gly
                485                 490                 495

His Asp Asn Glu Ala Tyr Glu Gly Ser Asp Val Asp Pro Ala Glu Ser
                500                 505                 510

Ala Ile Ser Asp Ile Ser Gly Ser Tyr Val Val Pro Gly Thr Ala Leu
                515                 520                 525

Gln Pro Leu Tyr Gln Ala Leu Asp Leu Pro Ala Glu Ile Val Ala Arg
                530                 535                 540

Ala Gly Arg Leu Thr Ala Thr Val Lys Val Ser Gln Val Asp Gly Arg
545                 550                 555                 560

Ile Asp Cys Glu Thr Leu Leu Gly Asn Lys Thr Phe Arg Thr Ser Phe
                565                 570                 575
```

```
Val Asp Gly Ala Val Leu Glu Thr Asn Gly Pro Glu Arg His Asn Leu
            580                 585                 590

Ser Phe Asp Ala Ser Gln Ser Thr Met Ala Ala Gly Pro Phe Ser Leu
            595                 600             605

Thr Tyr Ala Ala Ser Ala Ala Gly Leu Glu Val Arg Tyr Val Ala Ala
            610                 615             620

Gly Leu Asp His Arg Ala Val Phe Ala Pro Gly Val Ser Pro Arg Ser
625                     630                 635                 640

Ala Pro Gly Glu Val Thr Ala Phe Cys Ser Ala Leu Tyr Arg Phe Asn
                    645                 650                 655

Arg Glu Ala Gln Arg His Ser Leu Ile Gly Asn Leu Trp Phe His Pro
                660                 665                 670

Glu Gly Leu Ile Gly Leu Phe Ala Pro Phe Ser Pro Gly His Val Trp
            675                 680             685

Glu Ser Ala Asn Pro Phe Cys Gly Glu Ser Thr Leu Tyr Thr Arg Thr
            690                 695                 700

Trp Ser Glu Val Asp Ala Val Ser Ser Pro Ala Arg Pro Asp Leu Gly
705                     710                 715                 720

Phe Met Ser Glu Pro Ser Ile Pro Ser Arg Ala Ala Thr Pro Thr Leu
                    725                 730                 735

Ala Ala Pro Leu Pro Pro Ala Pro Asp Pro Ser Pro Pro Pro Ser
                740                 745                 750

Ala Pro Ala Leu Ala Glu Pro Ala Ser Gly Ala Thr Ala Gly Ala Pro
            755                 760             765

Ala Ile Thr His Gln Thr Ala Arg His Arg Leu Leu Phe Thr Tyr
            770                 775             780

Pro Asp Gly Ser Lys Val Phe Ala Gly Ser Leu Phe Glu Ser Thr Cys
785                     790                 795                 800

Thr Trp Leu Val Asn Ala Ser Asn Val Asp His Arg Pro Gly Gly Gly
                    805                 810                 815

Leu Cys His Ala Phe Tyr Gln Arg Tyr Pro Ala Ser Phe Asp Ala Ala
                820                 825                 830

Ser Phe Val Met Arg Asp Gly Ala Ala Ala Tyr Thr Leu Thr Pro Arg
            835                 840             845

Pro Ile Ile His Ala Val Ala Pro Asp Tyr Arg Leu Glu His Asn Pro
850                     855                 860

Lys Arg Leu Glu Ala Ala Tyr Arg Glu Thr Cys Ser Arg Leu Gly Thr
865                     870                 875                 880

Ala Ala Tyr Pro Leu Leu Gly Thr Gly Ile Tyr Gln Val Pro Ile Gly
                    885                 890                 895

Pro Ser Phe Asp Ala Trp Glu Arg Asn His Arg Pro Gly Asp Glu Leu
                900                 905                 910

Tyr Leu Pro Glu Leu Ala Ala Arg Trp Phe Glu Ala Asn Arg Pro Thr
            915                 920             925

Arg Pro Thr Leu Thr Ile Thr Glu Asp Val Ala Arg Thr Ala Asn Leu
            930                 935             940

Ala Ile Glu Leu Asp Ser Ala Thr Asp Val Gly Arg Ala Cys Ala Gly
945                     950                 955                 960

Cys Arg Val Thr Pro Gly Val Val Gln Tyr Gln Phe Thr Ala Gly Val
                    965                 970                 975

Pro Gly Ser Gly Lys Ser Arg Ser Ile Thr Gln Ala Asp Val Asp Val
                980                 985                 990
```

-continued

Val Val Val Pro Thr Arg Glu Leu Arg Asn Ala Trp Arg Arg Gly
        995                 1000                1005

Phe Ala Ala Phe Thr Pro His Thr Ala Ala Arg Val Thr Gln Gly Arg
    1010                1015                1020

Arg Val Val Ile Asp Glu Ala Pro Ser Leu Pro Pro His Leu Leu Leu
1025                1030                1035                1040

Leu His Met Gln Arg Ala Ala Thr Val His Leu Leu Gly Asp Pro Asn
                1045                1050                1055

Gln Ile Pro Ala Ile Asp Phe Glu His Ala Gly Leu Val Pro Ala Ile
            1060                1065                1070

Arg Pro Asp Leu Gly Pro Thr Ser Trp Trp His Val Thr His Arg Trp
        1075                1080                1085

Pro Ala Asp Val Cys Glu Leu Ile Arg Gly Ala Tyr Pro Met Ile Gln
    1090                1095                1100

Thr Thr Ser Arg Val Leu Arg Ser Leu Phe Trp Gly Glu Pro Ala Val
1105                1110                1115                1120

Gly Gln Lys Leu Val Phe Thr Gln Ala Ala Lys Pro Ala Asn Pro Gly
                1125                1130                1135

Ser Val Thr Val His Glu Ala Gln Gly Ala Thr Tyr Thr Glu Thr Thr
            1140                1145                1150

Ile Ile Ala Thr Ala Asp Ala Arg Gly Leu Ile Gln Ser Ser Arg Ala
        1155                1160                1165

His Ala Ile Val Ala Leu Thr Arg His Thr Glu Lys Cys Val Ile Ile
    1170                1175                1180

Asp Ala Pro Gly Leu Leu Arg Glu Val Gly Ile Ser Asp Ala Ile Val
1185                1190                1195                1200

Asn Asn Phe Phe Leu Ala Gly Gly Glu Ile Gly His Gln Arg Pro Ser
                1205                1210                1215

Val Ile Pro Arg Gly Asn Pro Asp Ala Asn Val Asp Thr Leu Ala Ala
            1220                1225                1230

Phe Pro Pro Ser Cys Gln Ile Ser Ala Phe His Gln Leu Ala Glu Glu
        1235                1240                1245

Leu Gly His Arg Pro Val Pro Val Ala Ala Val Leu Pro Pro Cys Pro
    1250                1255                1260

Glu Leu Glu Gln Gly Leu Leu Tyr Leu Pro Gln Glu Leu Thr Thr Cys
1265                1270                1275                1280

Asp Ser Val Val Thr Phe Glu Leu Thr Asp Ile Val His Cys Arg Met
                1285                1290                1295

Ala Ala Pro Ser Gln Arg Lys Ala Val Leu Ser Thr Leu Val Gly Arg
            1300                1305                1310

Tyr Gly Gly Arg Thr Lys Leu Tyr Asn Ala Ser His Ser Asp Val Arg
        1315                1320                1325

Asp Ser Leu Ala Arg Phe Ile Pro Ala Ile Gly Pro Val Gln Val Thr
    1330                1335                1340

Thr Cys Glu Leu Tyr Glu Leu Val Glu Ala Met Val Glu Lys Gly Gln
1345                1350                1355                1360

Asp Gly Ser Ala Val Leu Glu Leu Asp Leu Cys Asn Arg Asp Val Ser
                1365                1370                1375

Arg Ile Thr Phe Phe Gln Lys Asp Cys Asn Lys Phe Thr Thr Gly Glu
        1380                1385                1390

Thr Ile Ala His Gly Lys Val Gly Gln Gly Ile Ser Ala Trp Ser Lys
    1395                1400                1405

Thr Phe Cys Ala Leu Phe Gly Pro Trp Phe Arg Ala Ile Glu Lys Ala

```
        1410                1415                1420
Ile Leu Ala Leu Leu Pro Gln Gly Val Phe Tyr Gly Asp Ala Phe Asp
1425                1430                1435                1440

Asp Thr Val Phe Ser Ala Val Ala Ala Ala Lys Ala Ser Met Val
                1445                1450                1455

Phe Glu Asn Asp Phe Ser Glu Phe Asp Ser Thr Gln Asn Asn Phe Ser
                1460                1465                1470

Leu Gly Leu Glu Cys Ala Ile Met Glu Glu Cys Gly Met Pro Gln Trp
            1475                1480                1485

Leu Ile Arg Leu Tyr His Leu Ile Arg Ser Ala Trp Ile Leu Gln Ala
            1490                1495                1500

Pro Lys Glu Ser Leu Arg Gly Phe Trp Lys Lys His Ser Gly Glu Pro
1505                1510                1515                1520

Gly Thr Leu Leu Trp Asn Thr Val Trp Asn Met Ala Val Ile Thr His
                1525                1530                1535

Cys Tyr Asp Phe Arg Asp Phe Gln Val Ala Ala Phe Lys Gly Asp Asp
                1540                1545                1550

Ser Ile Val Leu Cys Ser Glu Tyr Arg Gln Ser Pro Gly Ala Ala Val
            1555                1560                1565

Leu Ile Ala Gly Cys Gly Leu Lys Leu Lys Val Asp Phe Arg Pro Ile
            1570                1575                1580

Gly Leu Tyr Ala Gly Val Val Val Ala Pro Gly Leu Gly Ala Leu Pro
1585                1590                1595                1600

Asp Val Val Arg Phe Ala Gly Arg Leu Thr Glu Lys Asn Trp Gly Pro
                1605                1610                1615

Gly Pro Glu Arg Ala Glu Gln Leu Arg Leu Ala Val Ser Asp Phe Leu
                1620                1625                1630

Arg Lys Leu Thr Asn Val Ala Gln Met Cys Val Asp Val Val Ser Arg
            1635                1640                1645

Val Tyr Gly Val Ser Pro Gly Leu Val His Asn Leu Ile Gly Met Leu
            1650                1655                1660

Gln Ala Val Ala Asp Gly Lys Ala His Phe Thr Glu Ser Val Lys Pro
1665                1670                1675                1680

Val Leu Asp Leu Thr Asn Ser Ile Leu Cys Arg Val Glu
                1685                1690

(2) INFORMATION FOR SEQ ID NO:8:

(i) SEQUENCE CHARACTERISTICS:
        (A) LENGTH: 660 amino acids
        (B) TYPE: amino acid
        (D) TOPOLOGY: linear (ii) MOLECULE TYPE: protein (xi) SEQUENCE DESCRIPTION: SEQ ID NO:8:

Met Arg Pro Arg Pro Ile Leu Leu Leu Leu Met Phe Leu Pro Met
 1                5                10                15

Leu Pro Ala Pro Pro Gly Gln Pro Ser Gly Arg Arg Gly Arg
            20                25                30

Arg Ser Gly Gly Ser Gly Gly Gly Phe Trp Gly Asp Arg Val Asp Ser
        35                40                45

Gln Pro Phe Ala Ile Pro Tyr Ile His Pro Thr Asn Pro Phe Ala Pro
    50                55                60

Asp Val Thr Ala Ala Ala Gly Ala Gly Pro Arg Val Arg Gln Pro Ala
65              70                75                80
```

```
Arg Pro Leu Gly Ser Ala Trp Arg Asp Gln Ala Gln Arg Pro Ala Val
                    85                  90                  95
Ala Ser Arg Arg Arg Pro Thr Thr Ala Gly Ala Ala Pro Leu Thr Ala
                100                 105                 110
Val Ala Pro Ala His Asp Thr Pro Pro Val Pro Asp Val Asp Ser Arg
            115                 120                 125
Gly Ala Ile Leu Arg Arg Gln Tyr Asn Leu Ser Thr Ser Pro Leu Thr
        130                 135                 140
Ser Ser Val Ala Thr Gly Thr Asn Leu Val Leu Tyr Ala Ala Pro Leu
145                 150                 155                 160
Ser Pro Leu Leu Pro Leu Gln Asp Gly Thr Asn Thr His Ile Met Ala
                165                 170                 175
Thr Glu Ala Ser Asn Tyr Ala Gln Tyr Arg Val Ala Arg Ala Thr Ile
                180                 185                 190
Arg Tyr Arg Pro Leu Val Pro Asn Ala Val Gly Gly Tyr Ala Ile Ser
            195                 200                 205
Ile Ser Phe Trp Pro Gln Thr Thr Thr Pro Thr Ser Val Asp Met
        210                 215                 220
Asn Ser Ile Thr Ser Thr Asp Val Arg Ile Leu Val Gln Pro Gly Ile
225                 230                 235                 240
Ala Ser Glu Leu Val Ile Pro Ser Glu Arg Leu His Tyr Arg Asn Gln
                245                 250                 255
Gly Trp Arg Ser Val Glu Thr Ser Gly Val Ala Glu Glu Ala Thr
            260                 265                 270
Ser Gly Leu Val Met Leu Cys Ile His Gly Ser Leu Val Asn Ser Tyr
            275                 280                 285
Thr Asn Thr Pro Tyr Thr Gly Ala Leu Gly Leu Leu Asp Phe Ala Leu
        290                 295                 300
Glu Leu Glu Phe Arg Asn Leu Thr Pro Gly Asn Thr Asn Thr Arg Val
305                 310                 315                 320
Ser Arg Tyr Ser Ser Thr Ala Arg His Arg Leu Arg Arg Gly Ala Asp
            325                 330                 335
Gly Thr Ala Glu Leu Thr Thr Thr Ala Ala Thr Arg Phe Met Lys Asp
        340                 345                 350
Leu Tyr Phe Thr Ser Thr Asn Gly Val Gly Glu Ile Gly Arg Gly Ile
        355                 360                 365
Ala Leu Thr Leu Phe Asn Leu Ala Asp Thr Leu Leu Gly Gly Leu Pro
        370                 375                 380
Thr Glu Leu Ile Ser Ser Ala Gly Gln Leu Phe Tyr Ser Arg Pro
385                 390                 395                 400
Val Val Ser Ala Asn Gly Glu Pro Thr Val Lys Leu Tyr Thr Ser Val
            405                 410                 415
Glu Asn Ala Gln Gln Asp Lys Gly Ile Ala Ile Pro His Asp Ile Asp
                420                 425                 430
Leu Gly Glu Ser Arg Val Val Ile Gln Asp Tyr Asp Asn Gln His Glu
        435                 440                 445
Gln Asp Arg Pro Thr Pro Ser Pro Ala Pro Ser Arg Pro Phe Ser Val
        450                 455                 460
Leu Arg Ala Asn Asp Val Leu Trp Leu Ser Leu Thr Ala Ala Glu Tyr
465                 470                 475                 480
Asp Gln Ser Thr Tyr Gly Ser Ser Thr Gly Pro Val Tyr Val Ser Asp
                485                 490                 495
```

```
Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
            515                 520                 525

Ile Gln Gln Tyr Ser Lys Thr Phe Phe Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
            580                 585                 590

Val Ser Ile Ser Ala Val Ala Val Leu Ala Pro His Ser Ala Leu Ala
            595                 600                 605

Leu Leu Glu Asp Thr Leu Asp Tyr Pro Ala Arg Ala His Thr Phe Asp
            610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

(2) INFORMATION FOR SEQ ID NO:9:

(i) SEQUENCE CHARACTERISTICS:
        (A) LENGTH: 123 amino acids
        (B) TYPE: amino acid
        (D) TOPOLOGY: linear (ii) MOLECULE TYPE: protein (xi) SEQUENCE DESCRIPTION: SEQ ID NO:9:

Met Asn Asn Met Ser Phe Ala Ala Pro Met Gly Ser Arg Pro Cys Ala
  1               5                  10                  15

Leu Gly Leu Phe Cys Cys Cys Ser Ser Cys Phe Cys Leu Cys Cys Pro
                 20                  25                  30

Arg His Arg Pro Val Ser Arg Leu Ala Ala Val Val Gly Gly Ala Ala
             35                  40                  45

Ala Val Pro Ala Val Val Ser Gly Val Thr Gly Leu Ile Leu Ser Pro
 50                  55                  60

Ser Gln Ser Pro Ile Phe Ile Gln Pro Thr Pro Ser Pro Pro Met Ser
 65                  70                  75                  80

Pro Leu Arg Pro Gly Leu Asp Leu Val Phe Ala Asn Pro Pro Asp His
                 85                  90                  95

Ser Ala Pro Leu Gly Val Thr Arg Pro Ser Ala Pro Pro Leu Pro His
            100                 105                 110

Val Val Asp Leu Pro Gln Leu Gly Pro Arg Arg
            115                 120

(2) INFORMATION FOR SEQ ID NO:10:

(i) SEQUENCE CHARACTERISTICS:
        (A) LENGTH: 7171 base pairs
        (B) TYPE: nucleic acid
        (C) STRANDEDNESS: double
        (D) TOPOLOGY: linear (ii) MOLECULE TYPE: DNA
```

-continued (iii) HYPOTHETICAL: NO (iv) ANTI-SENSE: NO (vi) ORIGINAL SOURCE:
    (C) INDIVIDUAL ISOLATE: Composite Mexico strain (xi) SEQUENCE DESCRIPTION: SEQ ID NO:10:

```
GCCATGGAGG CCCACCAGTT CATTAAGGCT CCTGGCATCA CTACTGCTAT T GAGCAAGCA      60
GCTCTAGCAG CGGCCAACTC CGCCCTTGCG AATGCTGTGG TGGTCCGGCC T TTCCTTTCC     120
CATCAGCAGG TTGAGATCCT TATAAATCTC ATGCAACCTC GGCAGCTGGT G TTTCGTCCT     180
GAGGTTTTTT GGAATCACCC GATTCAACGT GTTATACATA ATGAGCTTGA G CAGTATTGC     240
CGTGCTCGCT CGGGTCGCTG CCTTGAGATT GGAGCCCACC CACGCTCCAT T AATGATAAT     300
CCTAATGTCC TCCATCGCTG CTTTCTCCAC CCCGTCGGCC GGGATGTTCA G CGCTGGTAC     360
ACAGCCCCGA CTAGGGGACC TGCGGCGAAC TGTCGCCGCT CGGCACTTCG T GGTCTGCCA     420
CCAGCCGACC GCACTTACTG TTTTGATGGC TTTGCCGGCT GCCGTTTTGC C GCCGAGACT     480
GGTGTGGCTC TCTATTCTCT CCATGACTTG CAGCCGGCTG ATGTTGCCGA G GCGATGGCT     540
CGCCACGGCA TGACCCGCCT TTATGCAGCT TTCCACTTGC CTCCAGAGGT G CTCCTGCCT     600
CCTGGCACCT ACCGGACATC ATCCTACTTG CTGATCCACG ATGGTAAGCG C GCGGTTGTC     660
ACTTATGAGG GTGACACTAG CGCCGGTTAC AATCATGATG TTGCCACCCT C CGCACATGG     720
ATCAGGACAA CTAAGGTTGT GGGTGAACAC CCTTTGGTGA TCGAGCGGGT G CGGGGTATT     780
GGCTGTCACT TTGTGTTGTT GATCACTGCG GCCCCTGAGC CCTCCCCGAT G CCCTACGTT     840
CCTTACCCGC GTTCGACGGA GGTCTATGTC CGGTCTATCT TTGGGCCCGG C GGGTCCCCG     900
TCGCTGTTCC CGACCGCTTG TGCTGTCAAG TCCACTTTTC ACGCCGTCCC C ACGCACATC     960
TGGGACCGTC TCATGCTCTT TGGGGCCACC CTCGACGACC AGGCCTTTTG C TGCTCCAGG    1020
CTTATGACGT ACCTTCGTGG CATTAGCTAT AAGGTAACTG TGGGTGCCCT G GTCGCTAAT    1080
GAAGGCTGGA ATGCCACCGA GGATGCGCTC ACTGCAGTTA TTACGGCGGC T TACCTCACA    1140
ATATGTCATC AGCGTTATTT GCGGACCCAG GCGATTTCTA AGGGCATGCG C CGGCTTGAG    1200
CTTGAACATG CTCAGAAATT TATTTCACGC CTCTACAGCT GGCTATTTGA G AAGTCAGGT    1260
CGTGATTACA TCCCAGGCCG CCAGCTGCAG TTCTACGCTC AGTGCCGCCG C TGGTTATCT    1320
GCCGGGTTCC ATCTCGACCC CCGCACCTTA GTTTTTGATG AGTCAGTGCC T TGTAGCTGC    1380
CGAACCACCA TCCGGCGGAT CGCTGGAAAA TTTTGCTGTT TTATGAAGTG G CTCGGTCAG    1440
GAGTGTTCTT GTTTCCTCCA GCCCGCCGAG GGGCTGGCGG GCGACCAAGG T CATGACAAT    1500
GAGGCCTATG AAGGCTCTGA TGTTGATACT GCTGAGCCTG CCACCCTAGA C ATTACAGGC    1560
TCATACATCG TGGATGGTCG GTCTCTGCAA ACTGTCTATC AAGCTCTCGA C CTGCCAGCT    1620
GACCTGGTAG CTCGCGCAGC CCGACTGTCT GCTACAGTTA CTGTTACTGA A ACCTCTGGC    1680
CGTCTGGATT GCCAAACAAT GATCGGCAAT AAGACTTTTC TCACTACCTT T GTTGATGGG    1740
GCACGCCTTG AGGTTAACGG GCCTGAGCAG CTTAACCTCT CTTTTGACAG C CAGCAGTGT    1800
AGTATGGCAG CCGGCCCGTT TTGCCTCACC TATGCTGCCG TAGATGGCGG G CTGGAAGTT    1860
CATTTTTCCA CCGCTGGCCT CGAGAGCCGT GTTGTTTTCC CCCCTGGTAA T GCCCCGACT    1920
GCCCCGCCGA GTGAGGTCAC CGCCTTCTGC TCAGCTCTTT ATAGGCACAA C CGGCAGAGC    1980
CAGCGCCAGT CGGTTATTGG TAGTTTGTGG CTGCACCCTG AAGGTTTGCT C GGCCTGTTC    2040
CCGCCCTTTT CACCCGGGCA TGAGTGGCGG TCTGCTAACC CATTTTGCGG C GAGAGCACG    2100
```

```
CTCTACACCC GCACTTGGTC CACAATTACA GACACACCCT TAACTGTCGG G CTAATTTCC      2160

GGTCATTTGG ATGCTGCTCC CCACTCGGGG GGGCCACCTG CTACTGCCAC A GGCCCTGCT      2220

GTAGGCTCGT CTGACTCTCC AGACCCTGAC CCGCTACCTG ATGTTACAGA T GGCTCACGC      2280

CCCTCTGGGG CCCGTCCGGC TGGCCCCAAC CCGAATGGCG TTCCGCAGCG C CGCTTACTA      2340

CACACCTACC CTGACGGCGC TAAGATCTAT GTCGGCTCCA TTTTCGAGTC T GAGTGCACC      2400

TGGCTTGTCA ACGCATCTAA CGCCGGCCAC CGCCCTGGTG GCGGGCTTTG T CATGCTTTT      2460

TTTCAGCGTT ACCCTGATTC GTTTGACGCC ACCAAGTTTG TGATGCGTGA T GGTCTTGCC      2520

GCGTATACCC TTACACCCCG GCCGATCATT CATGCGGTGG CCCCGGACTA T CGATTGGAA      2580

CATAACCCCA AGAGGCTCGA GGCTGCCTAC CGCGAGACTT GCGCCCGCCG A GGCACTGCT      2640

GCCTATCCAC TCTTAGGCGC TGGCATTTAC CAGGTGCCTG TTAGTTTGAG T TTTGATGCC      2700

TGGGAGCGGA ACCACCGCCC GTTTGACGAG CTTTACCTAA CAGAGCTGGC G GCTCGGTGG      2760

TTTGAATCCA ACCGCCCCGG TCAGCCCACG TTGAACATAA CTGAGGATAC C GCCCGTGCG      2820

GCCAACCTGG CCCTGGAGCT TGACTCCGGG AGTGAAGTAG GCCGCGCATG T GCCGGGTGT      2880

AAAGTCGAGC CTGGCGTTGT GCGGTATCAG TTTACAGCCG GTGTCCCCGG C TCTGGCAAG      2940

TCAAAGTCCG TGCAACAGGC GGATGTGGAT GTTGTTGTTG TGCCCACTCG C GAGCTTCGG      3000

AACGCTTGGC GGCGCCGGGG CTTTGCGGCA TTCACTCCGC ACACTGCGGC C CGTGTCACT      3060

AGCGGCCGTA GGGTTGTCAT TGATGAGGCC CCTTCGCTCC CCCCACACTT G CTGCTTTTA      3120

CATATGCAGC GTGCTGCATC TGTGCACCTC CTTGGGGACC CGAATCAGAT C CCCGCCATA      3180

GATTTTGAGC ACACCGGTCT GATTCCAGCA ATACGGCCGG AGTTGGTCCC G ACTTCATGG      3240

TGGCATGTCA CCCACCGTTG CCCTGCAGAT GTCTGTGAGT TAGTCCGTGG T GCTTACCCT      3300

AAAATCCAGA CTACAAGTAA GGTGCTCCGT TCCCTTTTCT GGGGAGAGCC A GCTGTCGGC      3360

CAGAAGCTAG TGTTCACACA GGCTGCTAAG GCCGCGCACC CCGGATCTAT A ACGGTCCAT      3420

GAGGCCCAGG GTGCCACTTT TACCACTACA ACTATAATTG CAACTGCAGA T GCCCGTGGC      3480

CTCATACAGT CCTCCCGGGC TCACGCTATA GTTGCTCTCA CTAGGCATAC T GAAAAATGT      3540

GTTATACTTG ACTCTCCCGG CCTGTTGCGT GAGGTGGGTA TCTCAGATGC C ATTGTTAAT      3600

AATTTCTTCC TTTCGGGTGG CGAGGTTGGT CACCAGAGAC CATCGGTCAT T CCGCGAGGC      3660

AACCCTGACC GCAATGTTGA CGTGCTTGCG GCGTTTCCAC CTTCATGCCA A ATAAGCGCC      3720

TTCCATCAGC TTGCTGAGGA GCTGGGCCAC CGGCCGGCGC CGGTGGCGGC T GTGCTACCT      3780

CCCTGCCCTG AGCTTGAGCA GGGCCTTCTC TATCTGCCAC AGGAGCTAGC C TCCTGTGAC      3840

AGTGTTGTGA CATTTGAGCT AACTGACATT GTGCACTGCC GCATGGCGGC C CCTAGCCAA      3900

AGGAAAGCTG TTTTGTCCAC GCTGGTAGGC CGGTATGGCA GACGCACAAG G CTTTATGAT      3960

GCGGGTCACA CCGATGTCCG CGCCTCCCTT GCGCGCTTTA TTCCCACTCT C GGGCGGGTT      4020

ACTGCCACCA CCTGTGAACT CTTTGAGCTT GTAGAGGCGA TGGTGGAGAA G GGCCAAGAC      4080

GGTTCAGCCG TCCTCGAGTT GGATTTGTGC AGCCGAGATG TCTCCCGCAT A ACCTTTTC      4140

CAGAAGGATT GTAACAAGTT CACGACCGGC GAGACAATTG CGCATGGCAA A GTCGGTCAG      4200

GGTATCTTCC GCTGGAGTAA GACGTTTTGT GCCCTGTTTG GCCCCTGGTT C CGTGCGATT      4260

GAGAAGGCTA TTCTATCCCT TTTACCACAA GCTGTGTTCT ACGGGGATGC T TATGACGAC      4320

TCAGTATTCT CTGCTGCCGT GGCTGGCGCC AGCCATGCCA TGGTGTTTGA A AATGATTTT      4380

TCTGAGTTTG ACTCGACTCA GAATAACTTT TCCCTAGGTC TTGAGTGCGC C ATTATGGAA      4440
```

```
GAGTGTGGTA TGCCCCAGTG GCTTGTCAGG TTGTACCATG CCGTCCGGTC G GCGTGGATC    4500

CTGCAGGCCC AAAAGAGTC TTTGAGAGGG TTCTGGAAGA AGCATTCTGG T GAGCCGGGC    4560

AGCTTGCTCT GGAATACGGT GTGGAACATG GCAATCATTG CCCATTGCTA T GAGTTCCGG   4620

GACCTCCAGG TTGCCGCCTT CAAGGGCGAC GACTCGGTCG TCCTCTGTAG T GAATACCGC   4680

CAGAGCCCAG GCGCCGGTTC GCTTATAGCA GGCTGTGGTT TGAAGTTGAA G GCTGACTTC   4740

CGGCCGATTG GGCTGTATGC CGGGGTTGTC GTCGCCCCGG GGCTCGGGGC C CTACCCGAT   4800

GTCGTTCGAT TCGCCGGACG GCTTTCGGAG AAGAACTGGG GGCCTGATCC G GAGCGGGCA   4860

GAGCAGCTCC GCCTCGCCGT GCAGGATTTC CTCCGTAGGT TAACGAATGT G GCCCAGATT   4920

TGTGTTGAGG TGGTGTCTAG AGTTTACGGG GTTTCCCCGG GTCTGGTTCA T AACCTGATA   4980

GGCATGCTCC AGACTATTGG TGATGGTAAG GCGCATTTTA CAGAGTCTGT T AAGCCTATA   5040

CTTGACCTTA CACACTCAAT TATGCACCGG TCTGAATGAA TAACATGTGG T TTGCTGCGC   5100

CCATGGGTTC GCCACCATGC GCCCTAGGCC TCTTTTGCTG TTGTTCCTCT T GTTTCTGCC   5160

TATGTTGCCC GCGCCACCGA CCGGTCAGCC GTCTGGCCGC CGTCGTGGGC G GCGCAGCGG   5220

CGGTACCGGC GGTGGTTTCT GGGGTGACCG GGTTGATTCT CAGCCCTTCG C AATCCCCTA   5280

TATTCATCCA ACCAACCCCT TGCCCCAGA CGTTGCCGCT GCGTCCGGGT C TGGACCTCG    5340

CCTTCGCCAA CCAGCCCGGC CACTTGGCTC CACTTGGCGA GATCAGGCCC A GCGCCCCTC   5400

CGCTGCCTCC CGTCGCCGAC CTGCCACAGC CGGGGCTGCG GCGCTGACGG C TGTGGCGCC   5460

TGCCCATGAC ACCTCACCCG TCCCGGACGT TGATTCTCGC GGTGCAATTC T ACGCCGCCA   5520

GTATAATTTG TCTACTTCAC CCCTGACATC CTCTGTGGCC TCTGGCACTA A TTTAGTCCT   5580

GTATGCAGCC CCCCTTAATC CGCCTCTGCC GCTGCAGGAC GGTACTAATA C TCACATTAT   5640

GGCCACAGAG GCCTCCAATT ATGCACAGTA CCGGGTTGCC CGCGCTACTA T CCGTTACCG   5700

GCCCCTAGTG CCTAATGCAG TTGGAGGCTA TGCTATATCC ATTTCTTTCT G GCCTCAAAC   5760

AACCACAACC CCTACATCTG TTGACATGAA TTCCATTACT TCCACTGATG T CAGGATTCT   5820

TGTTCAACCT GGCATAGCAT CTGAATTGGT CATCCCAAGC GAGCGCCTTC A CTACCGCAA   5880

TCAAGGTTGG CGCTCGGTTG AGACATCTGG TGTTGCTGAG GAGGAAGCCA C CTCCGGTCT   5940

TGTCATGTTA TGCATACATG GCTCTCCAGT TAACTCCTAT ACCAATACCC C TTATACCGG   6000

TGCCCTTGGC TTACTGGACT TTGCCTTAGA GCTTGAGTTT CGCAATCTCA C CACCTGTAA   6060

CACCAATACA CGTGTGTCCC GTTACTCCAG CACTGCTCGT CACTCCGCCC G AGGGGCCGA   6120

CGGGACTGCG GAGCTGACCA CAACTGCAGC CACCAGGTTC ATGAAAGATC T CCACTTTAC   6180

CGGCCTTAAT GGGGTAGGTG AAGTCGGCCG CGGGATAGCT CTAACATTAC T TAACCTTGC   6240

TGACACGCTC CTCGGCGGGC TCCCGACAGA ATTAATTTCG TCGGCTGGCG G GCAACTGTT   6300

TTATTCCCGC CCGGTTGTCT CAGCCAATGG CGAGCCAACC GTGAAGCTCT A TACATCAGT   6360

GGAGAATGCT CAGCAGGATA AGGGTGTTGC TATCCCCCAC GATATCGATC T TGGTGATTC   6420

GCGTGTGGTC ATTCAGGATT ATGACAACCA GCATGAGCAG GATCGGCCCA C CCCGTCGCC   6480

TGCGCCATCT CGGCCTTTTT CTGTTCTCCG AGCAAATGAT GTACTTTGGC T GTCCCTCAC   6540

TGCAGCCGAG TATGACCAGT CCACTTACGG GTCGTCAACT GGCCCGGTTT A TATCTCGGA   6600

CAGCGTGACT TTGGTGAATG TTGCGACTGG CGCGCAGGCC GTAGCCCGAT C GCTTGACTG   6660

GTCCAAAGTC ACCCTCGACG GGCGGCCCCT CCCGACTGTT GAGCAATATT C CAAGACATT   6720

CTTTGTGCTC CCCCTTCGTG GCAAGCTCTC CTTTTGGGAG GCCGGCACAA C AAAAGCAGG   6780

TTATCCTTAT AATTATAATA CTACTGCTAG TGACCAGATT CTGATTGAAA A TGCTGCCGG   6840
```

| | | |
|---|---|---|
| CCATCGGGTC GCCATTTCAA CCTATACCAC CAGGCTTGGG GCCGGTCCGG T CGCCATTTC | | 6900 |
| TGCGGCCGCG GTTTTGGCTC CACGCTCCGC CCTGGCTCTG CTGGAGGATA C TTTTGATTA | | 6960 |
| TCCGGGGCGG GCGCACACAT TTGATGACTT CTGCCCTGAA TGCCGCGCTT T AGGCCTCCA | | 7020 |
| GGGTTGTGCT TTCCAGTCAA CTGTCGCTGA GCTCCAGCGC CTTAAAGTTA A GGTGGGTAA | | 7080 |
| AACTCGGGAG TTGTAGTTTA TTTGGCTGTG CCCACCTACT TATATCTGCT G ATTTCCTTT | | 7140 |
| ATTTCCTTTT TCTCGGTCCC GCGCTCCCTG A | | 7171 |

(2) INFORMATION FOR SEQ ID NO:11:

(i) SEQUENCE CHARACTERISTICS:
        (A) LENGTH: 1575 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: T: Mexican strain (xi) SEQUENCE DESCRIPTION: SEQ ID NO:11:

| | | |
|---|---|---|
| GTTGCGTGAG GTGGGTATCT CAGATGCCAT TGTTAATAAT TCTTCCTTT C GGGTGGCGA | | 60 |
| GGTTGGTCAC CAGAGACCAT CGGTCATTCC GCGAGGCAAC CCTGACCGCA A TGTTGACGT | | 120 |
| GCTTGCGGCG TTTCCACCTT CATGCCAAAT AAGCGCCTTC CATCAGCTTG C TGAGGAGCT | | 180 |
| GGGCCACCGG CCGGCGCCGG TGGCGGCTGT GCTACCTCCC TGCCCTGAGC T TGAGCAGGG | | 240 |
| CCTTCTCTAT CTGCCACAGG AGCTAGCCTC CTGTGACAGT GTTGTGACAT T TGAGCTAAC | | 300 |
| TGACATTGTG CACTGCCGCA TGGCGGCCCC TAGCCAAAGG AAAGCTGTTT T GTCCACGCT | | 360 |
| GGTAGGCCGG TATGGCAGAC GCACAAGGCT TTATGATGCG GGTCACACCG A TGTCCGCGC | | 420 |
| CTCCCTTGCG CGCTTTATTC CCACTCTCGG GCGGGTTACT GCCACCACCT G TGAACTCTT | | 480 |
| TGAGCTTGTA GAGGCGATGG TGGAGAAGGG CCAAGACGGT TCAGCCGTCC T CGAGTTGGA | | 540 |
| TTTGTGCAGC CGAGATGTCT CCCGCATAAC CTTTTTCCAG AAGGATTGTA A CAAGTTCAC | | 600 |
| GACCGGCGAG ACAATTGCGC ATGGCAAAGT CGGTCAGGGT ATCTTCCGCT G GAGTAAGAC | | 660 |
| CTTTTGTGCC CTGTTTGGCC CCTGGTTCCG TGCGATTGAG AAGGCTATTC T ATCCCTTTT | | 720 |
| ACCACAAGCT GTGTTCTACG GGGATGCTTA TGACGACTCA GTATTCTCTG C TGCCGTGGC | | 780 |
| TGGCGCCAGC CATGCCATGG TGTTTGAAAA TGATTTTTCT GAGTTTGACT C GACTCAGAA | | 840 |
| TAACTTTTCC CTAGGTCTTG AGTGCGCCAT TATGGAAGAG TGTGGTATGC C CCAGTGGCT | | 900 |
| TGTCAGGTTG TACCATGCCG TCCGGTCGGC GTGGATCCTG CAGGCCCCAA A AGAGTCTTT | | 960 |
| GAGAGGGTTC TGGAAGAAGC ATTCTGGTGA GCCGGGCACG TTGCTCTGGA A TACGGTGTG | | 1020 |
| GAACATGGCA ATCATTGCCC ATTGCTATGA GTTCCGGGAC CTCCAGGTTG C CGCCTTCAA | | 1080 |
| GGGCGACGAC TCGGTCGTCC TCTGTAGTGA ATACCGCCAG AGCCCAGGCG C CGGTTCGCT | | 1140 |
| TATAGCAGGC TGTGGTTTGA AGTTGAAGGC TGACTTCCGG CCGATTGGGC T GTATGCCGG | | 1200 |
| GGTTGTCGTC GCCCCGGGGC TCGGGCCCT ACCCGATGTC GTTCGATTCG C CGGACGGCT | | 1260 |
| TTCGGAGAAG AACTGGGGGC CTGATCCGGA GCGGGCAGAG CAGCTCCGCC T CGCCGTGCA | | 1320 |
| GGATTTCCTC CGTAGGTTAA CGAATGTGGC CCAGATTTGT GTTGAGGTGG T GTCTAGAGT | | 1380 |

```
TTACGGGGTT TCCCCGGGTC TGGTTCATAA CCTGATAGGC ATGCTCCAGA C TATTGGTGA    1440

TGGTAAGGCG CATTTTACAG AGTCTGTTAA GCCTATACTT GACCTTACAC A CTCAATTAT    1500

GCACCGGTCT GAATGAATAA CATGTGGTTT GCTGCGCCCA TGGGTTCGCC A CCATGCGCC    1560

CTAGGCCTCT TTTGC                                                      1575

(2) INFORMATION FOR SEQ ID NO:12:

(i) SEQUENCE CHARACTERISTICS:
        (A) LENGTH: 874 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Tashkent strain (xi) SEQUENCE DESCRIPTION: SEQ ID NO:12:

CGGGCCCCGT ACAGGTCACA ACCTGTGAGT TGTACGAGCT AGTGGAGGCC A TGGTCGAGA      60

AAGGCCAGGA TGGCTCCGCC GTCCTTGAGC TCGATCTCTG CAACCGTGAC G TGTCCAGGA    120

TCACCTTTTT CCAGAAAGAT TGCAATAAGT TCACCACGGG AGAGACCATC G CCCATGGTA    180

AAGTGGGCCA GGGCATTTCG GCCTGGAGTA AGACCTTCTG TGCCCTTTTC G GCCCCTGGT    240

TCCGTGCTAT TGAGAAGGCT ATTCTGGCCC TGCTCCCTCA GGGTGTGTTT T ATGGGGATG    300

CCTTTGATGA CACCGTCTTC TCGGCGCGTG TGGCCGCAGC AAAGGCGTCC A TGGTGTTTG    360

AGAATGACTT TTCTGAGTTT GACTCCACCC AGAATAATTT TTCCCTGGGC C TAGAGTGTG    420

CTATTATGGA GAAGTGTGGG ATGCCGAAGT GGCTCATCCG CTTGTACCAC C TTATAAGGT    480

CTGCGTGGAT CCTGCAGGCC CCGAAGGAGT CCCTGCGAGG GTGTTGGAAG A AACACTCCG    540

GTGAGCCCGG CACTCTTCTA TGGAATACTG TCTGGAACAT GGCCGTTATC A CCCATTGTT    600

ACGATTTCCG CGATTTGCAG GTGGCTGCCT TTAAAGGTGA TGATTCGATA G TGCTTTGCA    660

GTGAGTACCG TCAGAGTCCA GGGGCTGCTG TCCTGATTGC TGGCTGTGGC T TAAAGCTGA    720

AGGTGGGTTT CCGTCCGATT GGTTTGTATG CAGGTGTTGT GGTGACCCCC G GCCTTGGCG    780

CGCTTCCCGA CGTCGTGCGC TTGTCCGGCC GGCTTACTGA AGAGAATTGG G GCCCTGGCC    840

CTGAGCGGGC GGAGCAGCTC CGCCTTGCTG TGCG                                 874

(2) INFORMATION FOR SEQ ID NO:13:

(i) SEQUENCE CHARACTERISTICS:
        (A) LENGTH: 449 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Clone 406.4-2 cDNA (ix) FEATURE:
        (A) NAME/KEY: CDS
        (B) LOCATION: 2..100
```

(xi) SEQUENCE DESCRIPTION: SEQ ID NO:13:

```
C GCC AAC CAG CCC GGC CAC TTG GCT CCA CTT  GGC GAG ATC AGG CCC       46
  Ala Asn Gln Pro Gly His Leu Ala Pro Leu  Gly Glu Ile Arg Pro
  1               5                  10                  15

AGC GCC CCT CCG CTG CCT CCC GTC GCC GAC C TG CCA CAG CCG GGG CTG     94
Ser Ala Pro Pro Leu Pro Pro Val Ala Asp L eu Pro Gln Pro Gly Leu
                20                  25                  30

CGG CGC TGACGGCTGT GGCGCCTGCC CATGACACCT CACCCGTCCC G GACGTTGAT     150
Arg Arg

TCTCGCGGTG CAATTCTACG CCGCCAGTAT AATTTGTCTA CTTCACCCCT G ACATCCTCT  210

GTGGCCTCTG GCACTAATTT AGTCCTGTAT GCAGCCCCCC TTAATCCGCC T CTGCCGCTG  270

CAGGACGGTA CTAATACTCA CATTATGGCC ACAGAGGCCT CCAATTATGC A CAGTACCGG  330

GTTGCCCGCG CTACTATCCG TTACCGGCCC CTAGTGCCTA ATGCAGTTGG A GGCTATGCT  390

ATATCCATTT CTTTCTGGCC TCAAACAACC ACAACCCCTA CATCTGTTGA C ATGAATTC   449
```

(2) INFORMATION FOR SEQ ID NO:14:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:14:

```
Ala Asn Gln Pro Gly His Leu Ala Pro Leu G ly Glu Ile Arg Pro Ser
1               5                  10                  15

Ala Pro Pro Leu Pro Pro Val Ala Asp Leu P ro Gln Pro Gly Leu Arg
            20                  25                  30

Arg
```

(2) INFORMATION FOR SEQ ID NO:15:

(i) SEQUENCE CHARACTERISTICS:
        (A) LENGTH: 130 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Clone 406.3-2

(ix) FEATURE:
        (A) NAME/KEY: CDS
        (B) LOCATION: 5..130

(xi) SEQUENCE DESCRIPTION: SEQ ID NO:15:

```
GGAT ACT TTT GAT TAT CCG GGG CGG GCG CAC ACA TTT GAT GAC TTC TGC    49
     Thr Phe Asp Tyr Pro Gly Arg Al a His Thr Phe Asp Asp Phe Cys
     1               5                  10                  15

CCT GAA TGC CGC GCT TTA GGC CTC CAG GGT T GT GCT TTC CAG TCA ACT    97
Pro Glu Cys Arg Ala Leu Gly Leu Gln Gly C ys Ala Phe Gln Ser Thr
                20                  25                  30

GTC GCT GAG CTC CAG CGC CTT AAA GTT AAG G TT                       130
Val Ala Glu Leu Gln Arg Leu Lys Val Lys V al
                35                  40
```

(2) INFORMATION FOR SEQ ID NO:16:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:16:

```
Thr Phe Asp Tyr Pro Gly Arg Ala His Thr P he Asp Asp Phe Cys Pro
 1               5                  10                  15
Glu Cys Arg Ala Leu Gly Leu Gln Gly Cys A la Phe Gln Ser Thr Val
                20                  25                  30
Ala Glu Leu Gln Arg Leu Lys Val Lys Val
                35                  40
```

(2) INFORMATION FOR SEQ ID NO:17:

(i) SEQUENCE CHARACTERISTICS:
        (A) LENGTH: 33 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: 406.4-2 epitope - Mexican strain (xi) SEQUENCE DESCRIPTION: SEQ ID NO:17:

```
Ala Asn Gln Pro Gly His Leu Ala Pro Leu G ly Glu Ile Arg Pro Ser
 1               5                  10                  15
Ala Pro Pro Leu Pro Pro Val Ala Asp Leu P ro Gln Pro Gly Leu Arg
                20                  25                  30
Arg
```

(2) INFORMATION FOR SEQ ID NO:18:

(i) SEQUENCE CHARACTERISTICS:
        (A) LENGTH: 33 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: 406.4-2 epitope - Burma strain (xi) SEQUENCE DESCRIPTION: SEQ ID NO:18:

```
Ala Asn Pro Pro Asp His Ser Ala Pro Leu G ly Val Thr Arg Pro Ser
 1               5                  10                  15
Ala Pro Pro Leu Pro His Val Val Asp Leu P ro Gln Leu Gly Pro Arg
                20                  25                  30
Arg (2) INFORMATION FOR SEQ ID NO:19:

(i) SEQUENCE CHARACTERISTICS:
        (A) LENGTH: 42 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: 406.3-2 epitope - Mexican strain (xi) SEQUENCE DESCRIPTION: SEQ ID NO:19:

```
Thr Phe Asp Tyr Pro Gly Arg Ala His Thr P he Asp Asp Phe Cys Pro
1               5                   10                  15

Glu Cys Arg Ala Leu Gly Leu Gln Gly Cys A la Phe Gln Ser Thr Val
            20                  25                  30

Ala Glu Leu Gln Arg Leu Lys Val Lys Val
        35                  40
```

(2) INFORMATION FOR SEQ ID NO:20:

(i) SEQUENCE CHARACTERISTICS:
        (A) LENGTH: 42 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: 406.3-2 epitope - Burma strain (xi) SEQUENCE DESCRIPTION: SEQ ID NO:20:

```
Thr Leu Asp Tyr Pro Ala Arg Ala His Thr P he Asp Asp Phe Cys Pro
1               5                   10                  15

Glu Cys Arg Pro Leu Gly Leu Gln Gly Cys A la Phe Gln Ser Thr Val
            20                  25                  30

Ala Glu Leu Gln Arg Leu Lys Met Lys Val
        35                  40
```